(12) United States Patent
Redcorn et al.

(10) Patent No.: US 12,269,764 B2
(45) Date of Patent: Apr. 8, 2025

(54) HYDROGELS FOR THE ENTRAPMENT OF BACTERIA

(71) Applicant: University of Washington, Seattle, WA (US)

(72) Inventors: Raymond Redcorn, Seattle, WA (US); Mari-Karoliina Henriikka Winkler, Seattle, WA (US); Bruce Godfrey, Seattle, WA (US); David A. Stahl, Seattle, WA (US)

(73) Assignee: University of Washington, Seattle, WA (US)

( * ) Notice: Subject to any disclaimer, the term of this patent is extended or adjusted under 35 U.S.C. 154(b) by 28 days.

(21) Appl. No.: 17/767,613

(22) PCT Filed: Oct. 13, 2020

(86) PCT No.: PCT/US2020/055402
§ 371 (c)(1),
(2) Date: Apr. 8, 2022

(87) PCT Pub. No.: WO2021/076508
PCT Pub. Date: Apr. 22, 2021

(65) Prior Publication Data
US 2024/0076221 A1 Mar. 7, 2024

Related U.S. Application Data

(60) Provisional application No. 62/914,884, filed on Oct. 14, 2019.

(51) Int. Cl.
*C02F 3/10* (2023.01)
*C02F 3/28* (2023.01)
(Continued)

(52) U.S. Cl.
CPC .............. *C02F 3/341* (2013.01); *C02F 3/108* (2013.01); *C02F 3/2806* (2013.01); *C12N 11/04* (2013.01);
(Continued)

(58) Field of Classification Search
CPC ........ C02F 3/341; C02F 3/108; C02F 3/2806; C02F 2103/005; C02F 1/725; C02F 3/301;
(Continued)

(56) References Cited

U.S. PATENT DOCUMENTS 6,217,859 B1  4/2001  Chang et al.
6,861,064 B1  3/2005  Laakso et al.
(Continued)

FOREIGN PATENT DOCUMENTS

CN  102864088    1/2013
CN  102864088 A  1/2013
(Continued)

OTHER PUBLICATIONS

English translation of patent publication JP-10180282A, published Jul. 7, 1998. (Year: 1998).*

(Continued)

*Primary Examiner* — Joseph W Drodge
(74) *Attorney, Agent, or Firm* — Christensen O'Connor Johnson Kindness PLLC

(57) ABSTRACT

Hydrogels for entrapment of live microorganisms and methods of their use, such as in wastewater purification, are disclosed.

18 Claims, 23 Drawing Sheets

(51) Int. Cl.
| | |
|---|---|
| C02F 3/34 | (2023.01) |
| C12N 11/04 | (2006.01) |
| C12N 11/08 | (2020.01) |
| C12N 11/084 | (2020.01) |
| C12N 11/087 | (2020.01) |
| C12N 11/12 | (2006.01) |
| C02F 103/00 | (2006.01) |

(52) U.S. Cl.
CPC .......... *C12N 11/084* (2020.01); *C12N 11/087* (2020.01); *C12N 11/12* (2013.01); *C02F 2103/005* (2013.01)

(58) Field of Classification Search
CPC ........ C02F 2303/18; C02F 3/34; C12N 11/04; C12N 11/084; C12N 11/087; C12N 11/12; C12N 11/10; C12N 11/08; C12N 11/082; Y02W 10/10
See application file for complete search history.

(56) References Cited

U.S. PATENT DOCUMENTS

| | | | |
|---|---|---|---|
| 7,597,808 B2 | 10/2009 | Shiotani | |
| 8,227,238 B2 | 7/2012 | Abe | |
| 8,293,109 B2 | 10/2012 | Kimura | |
| 9,212,358 B2 | 12/2015 | Razavi-Shirazi | |
| 10,202,567 B2 | 2/2019 | Stolaroff | |
| 10,894,732 B2 | 1/2021 | Novak | |
| 2001/0051150 A1 | 12/2001 | Ranganathan et al. | |
| 2002/0187134 A1 | 12/2002 | Ranganathan | |
| 2004/0209361 A1* | 10/2004 | Hemperly | C12N 5/0068 435/404 |
| 2004/0234962 A1 | 11/2004 | Alarcon et al. | |
| 2005/0123529 A1 | 6/2005 | O'Loughlin | |
| 2007/0205149 A1* | 9/2007 | Jones | C12N 11/04 210/601 |
| 2008/0051696 A1 | 2/2008 | Curtin | |
| 2008/0264858 A1 | 10/2008 | Stamets | |
| 2009/0143463 A1 | 6/2009 | Takenaka | |
| 2010/0114012 A1 | 5/2010 | Sandford | |
| 2010/0317085 A1* | 12/2010 | Boedicker | C12M 1/14 435/252.4 |
| 2012/0177622 A1 | 7/2012 | Suzuki | |
| 2016/0030890 A1 | 2/2016 | Lee et al. | |
| 2016/0031766 A1 | 2/2016 | Bezbaruah et al. | |
| 2016/0051600 A1 | 2/2016 | Martín Del Campo López | |
| 2016/0144094 A1 | 5/2016 | Margolin | |
| 2017/0258857 A1 | 9/2017 | Philipp | |
| 2017/0355979 A1* | 12/2017 | Bae | C02F 3/104 |
| 2018/0021386 A1 | 1/2018 | Shum et al. | |
| 2018/0021452 A1 | 1/2018 | Huang | |
| 2018/0084805 A1 | 3/2018 | Fang | |
| 2018/0289755 A1 | 10/2018 | Al-Furaih | |
| 2019/0218497 A1 | 7/2019 | Boedicker et al. | |
| 2019/0375662 A1 | 12/2019 | Novak | |
| 2020/0255818 A1 | 8/2020 | Knipe | |
| 2022/0000938 A1 | 1/2022 | Yager | |

FOREIGN PATENT DOCUMENTS

| | | | |
|---|---|---|---|
| CN | 103667124 | 3/2014 | |
| CN | 103667124 A | 3/2014 | |
| CN | 106222158 | 12/2016 | |
| CN | 106222158 A | 12/2016 | |
| CN | 106830563 A * | 6/2017 | ............... C02F 9/00 |
| CN | 107156587 | 9/2017 | |
| CN | 107156587 A | 9/2017 | |
| CN | 107324616 A * | 11/2017 | ............... C02F 9/00 |
| CN | 109464225 | 3/2019 | |
| CN | 109464225 A | 3/2019 | |
| CN | 109496234 | 3/2019 | |
| CN | 109496234 A | 3/2019 | |
| CN | 109734174 A * | 5/2019 | ............ Y02W 10/10 |
| ES | 2368401 | 11/2011 | |
| ES | 2368401 A1 | 11/2011 | |
| JP | 10180282 A * | 7/1998 | ............ Y02W 10/10 |
| JP | 3361570 B2 * | 1/2003 | ............ Y02W 10/10 |
| JP | 2004033808 A * | 2/2004 | ............ Y02W 10/10 |
| JP | 2004533442 | 11/2004 | |
| JP | 2007507526 | 3/2007 | |
| JP | 2008018153 | 1/2008 | |
| JP | 2014199432 | 10/2014 | |
| JP | 2014199432 A | 10/2014 | |
| TW | 201427673 | 7/2014 | |
| TW | 201427673 A | 7/2014 | |
| WO | 2002091833 | 11/2002 | |
| WO | 2002091833 A1 | 11/2002 | |
| WO | 2003088984 | 10/2003 | |
| WO | 2003088984 A1 | 10/2003 | |
| WO | WO-2004094625 A1 * | 11/2004 | ........... C12N 5/0068 |
| WO | 2014/033638 A2 | 3/2014 | |
| WO | 2014033638 | 3/2014 | |
| WO | 2015019307 | 2/2015 | |
| WO | 2015019307 A1 | 2/2015 | |
| WO | 2017136561 A1 | 8/2017 | |
| WO | WO-2018017845 A1 * | 1/2018 | ........... A61B 5/6806 |
| WO | 2019117645 | 6/2019 | |
| WO | 2019117645 A1 | 6/2019 | |

OTHER PUBLICATIONS

English translation of Patent Publication JP3361570 , published Jan. 7, 2003. (Year: 2003).*
English translation of patent publication JP-2004033808A, published Feb. 5, 2004. (Year: 2004).*
English translation of Patent Publication CN106830563, published Jun. 13, 2017. (Year: 2017).*
English translation of Patent Publication CN107324616, published Nov. 7, 2017. (Year: 2017).*
English translation of Patent Publication CN109734174, published May 10, 2019. (Year: 2019).*
Agarwal, T. et al. Calcium alginate-carboxymethyl cellulose beads for colon-targeteddrug delivery, International Journal of Biological Macromolecules 75 (2015) 409-417.
Amidon, S. et al. Colon-Targeted Oral Drug Delivery Systems: Design Trends and Approaches, AAPS PharmSciTech, vol. 16, No. 4, Aug. 2015, 11 pages.
Bashan, Y. et al. Alginate microbeads as inoculant carriers for plant growth-promoting bacteria, Biol Fertil Soils (2002) 35:359-368.
Chai, Y. et al. Diffusion Coefficients in Intrahollow Calcium Alginate Microcapsules, J. Chem. Eng. Data 2004, 49, 475-478.
Coussa, R.G. et al. Microencapsulated *Saccharomyces cerevisiae* Column Bioreactor for Potential Use in Renal Failure Uremia, Artificial Cells, Blood Substitutes, and Biotechnology, 40;1-2 (2012) 103-112.
Cowen, A. Boba Spherification: The Science of Juice-filled Caviar, Science Buddies, Oct. 6, 2014, https://www.sciencebuddies.org/blog/boba-spherification-the-science-of-juice-filled-caviar, 4 pages.
Davilas, A. et al. In-vitro study on the competitive binding of diflunisal and uraemic toxins to serum albumin and human plasma using a potentiometric ion-probe technique, Journal of Pharmacy and Pharmacology 2006, 58: 1467-1474.
Dealler, S.F. et al. Enzymatic Degradation of Urinary Indoxyl Sulfate by Providencia stuartii and Klebsiella pneumoniae Causes the Purple Urine Bag Syndrome, Journal of Clinical Microbiology, Oct. 1988, p. 2152-2156.
Evenepoel, P. et al. Uremic toxins originating from colonic microbial metabolism, Kidney International (2009) 76 (Suppl 114), S12-S19.
Fang, C.Y. et al. Selection of uremic toxin-reducing probiotics in vitro and in vivo, Journal of Functional Foods 7 (2014) 407-415.
Gosmann, B. et al. Oxygen uptake of microorganisms entrapped in Ca-alginate, Applied Microbiology and Biotechnology vol. 23, pp. 163-167(1986).
Gramigna, J. Probiotics may reduce urea in patients with non-dialysis CKD, Healio, Dec. 31, 2018, https://www.healio.com/news/nephrology/20181231/probiotics-may-reduce-urea-in-patients-with-nondialysis-ckd, 2 pages.

(56) References Cited

OTHER PUBLICATIONS

Hida, M. et al. Inhibition of the Accumulation of Uremic Toxins in the Blood and Their Precursors in the Feces after Oral Administration of Lebenin®, a Lactic Acid Bacteria Preparation, to Uremic Patients Undergoing Hemodialysis, Nephron, 1996;74 (2) 349-355.
Jain, P. Potentials and limitations of microorganisms as renal failure biotherapeutics, Biologics: Targets & Therapy 2009:3 233-243.
Johansen, A. et al. Immobilization of yeast cells by internal gelation of alginate, Enzyme and Microbial Technology, vol. 8 No. 3, Mar. 1986, 145-148.
Koppe, L. Probiotics and chronic kidney disease, Kidney International (2015) 88, 958-966.
Krasaekoopt, W. et al. The influence of coating materials on some properties of alginate beads and survivability of microencapsulated probiotic bacteria, International Dairy Journal 14 (2004) 737-743.
Lekawanvijit, S. et al. The Uremic Toxin Adsorbent AST-120 Abrogates Cardiorenal Injury Following Myocardial Infarction, PLoS One. 2013; 8(12): e83687.
Lin, J. et al. In Vitro and in Vivo Characterization of Alginate-Chitosan-Alginate Artificial Microcapsules for Therapeutic Oral Delivery of Live Bacterial Cells, Journal of Bioscience and Bioengineering, 105(6); Jun. 2008, 660-665.
Miranda Alatriste, P.V. et al. Effect of probiotics on human blood urea levels in patients with chronic renal failure, Nutr Hosp. 2014;29(3):582-590.
O'Loughlin, J.A. et al. Degradation of low molecular weight uremic solutes by oral delivery of encapsulated enzymes, ASAIO J. May-Jun. 2004;50(3):253-60.
O'Loughlin, J.A. et al. In Vivo and in Vitro Degradation of Urea and Uric Acid by Encapsulated Genetically Modified Microorganisms, Tissue Engineering, vol. 10, No. 9/10, 2004.
Prakash, S. et al. Microencapsulated genetically engineered live *E.coli* DHS cells administered orally to maintain normal plasma urea level in uremic rats, Nature Medicine, vol. 2, No. 8, Aug. 1996, 883-887.
Prakash, S. et al. Growth and Survival of Renal Failure Rats that Received Oral Microencapsulated Genetically Engineered *E. coli* Dh5 Cells for Urea Removal, Artificial Cells, Blood Substitutes, and Biotechnology, vol. 26, No. 1, 1998, 35-51.
Sultana, K. et al. Encapsulation of probiotic bacteria with alginate-starch and evaluation of survival in simulated gastrointestinal conditions and in yoghurt, International Journal of Food Microbiology 62 (2000) 47-55.
Takayama, F. et al. Bifidobacterium in Gastro-Resistant Seamless Capsule Reduces Serum Levels of Indoxyl Sulfate in Patients on Hemodialysis, American Journal of Kidney Diseases, vol. 41, No. 1, Suppl 1 (March), 2003: pp. S142-S145.
Tao, S. et al. Effects of probiotic supplements on the progression of chronic kidney disease: A meta-analysis, Nephrology 24 (2019) 1122-1130.
Wang, J.Y. et al. Application of hydrogel encapsulated carbonate precipitating bacteriafor approaching a realistic self-healing in concrete, Construction and Building Materials 68 (2014) 110-119.
Zheng, D.W. et al. An orally delivered microbial cocktail for the removal of nitrogenous metabolic waste in animal models of kidney failure, Nature Biomedical Engineering vol. 4, pp. 853-862(2020).
C. Tomaro-Ducesneau et al., "Microencapsulation for the Therapeutic Delivery of Drugs, Live Mammalian and Bacterial Cells, and Other Biopharmaceutics: Current Status and Future Directions", Journal of Pharmaceutics, Dec. 4, 2012, pp. 1-19.
S. Prakash et al.,"Renal Failure Rats that Received Oral Microencapsulated Genetically Engineered *E. coli* Dh5 Cells for Urea Removal", Artificial Cells, Blood Substitutes, and Immobilization Biotechnology., vol. 26, No. 1, Jan. 1, 1998, pp. 35-51.
B. Hamarat, "Alginate Beads Encapsulation Matrix for Urease and Polyethyleneglycol-Urease", Artificial Cells, Blood Substitutes, and Immobilization Biotechnology., vol. 35, No. 4, Jan. 1, 2007, pp. 457-465.
S. Abhishek et al. "Biopolymer matrix for nano-encapsulation of urease—A model protein and its application in urea detection", Journal of Colloid and Interface Science, Academic Press, Inc, US, vol. 490, Nov. 9, 2016, pp. 452-461.
Examiner's Decision of Refusal (with translation) for Japanese Patent Application No. 2021-519807, filed Oct. 14, 2019; 15 pages total.
Bulut E. et al., "Novel ionically crosslinked acrylamide-grafted poly(vinyl alcohol)/sodium 1-3, 29-32. 39-41, 45-4 7 alginate/sodium carboxymethyl cellulose pH-sensitive microspheres for delivery of Alzheimer's drug donepezil hydrochloride: Preparation and optimization of release conditions", Artificial Cells, Nanomedicine, and Biotechnology, 2016, vol. 44, issue 2, pp. 431-442, retrieved from the Internet:< DOI: 10.3109/21691401.2014.962741 >; see entire document.
Combined International Search Report and Written Opinion received in International Application No. PCT/US2020/55402, filed Oct. 13, 2020; dated Mar. 11, 2021; 8 pages total.
Desai N. P. et al., "Interpenetrating polymer networks of alginate and polyethylene glycol for 1-3, 39-41, 45-47 encapsulation of islets of Langerhans", Journal of Microencapsulation, 2000, vol. 17, issue 6, pp. 677-690, retrieved from the Internet:< DOI: 10.1080/02652040050161675 >; see entire document, especially, p. 677-679.
Cano et al.; "Review and Perspectives of the Use of Alginate as a Polymer Matrix for Microorganisms Applied in Agro-Industry"; Molecules; Jun. 30, 2022; pp. 1-20; vol. 27, No. 4248.
International Search Report received for International Application No. PCT/US/23/60180; mailed on Jun. 14, 2023; 10 pages total.
Suman et al.; "Development of Hydrogel based Bio-Inoculant Formulations and their Impact on Plant Biometric Parameters of Wheat (*Triticum aestivum* L.)"; International Journal of Current Microbiology. App. Sci.; 2016; pp. 89-901; vol. 5; No. 3.
International Search Report mailed Jan. 2, 2020, issued in corresponding International Application No. PCT/US2019/056119, filed on Oct. 14, 2019, 2 pages.
International Prelimininary Report on Patentability mailed Apr. 8, 2021, issued in corresponding International Application No. PCT/US2019/056119, filed on Oct. 14, 2019, 6 pages.
International Search Report and Written Opinion mailed Jan. 2, 2020, issued in corresponding International Application No. PCT/US2019/056119, filed on Oct. 14, 2019, 8 pages.
International Prelimininary Report on Patentability mailed Apr. 19, 2022, issued in corresponding International Application No. PCT/US2020/055402, filed on Oct. 13, 2020, 1 pages.
International Search Report and Written Opinion mailed Feb. 10, 2021, issued in corresponding International Application No. PCT/US2020/055402, filed on Oct. 13, 2020, 8 pages.
Agler, Matthew T., et al. "Waste to bioproduct conversion with undefined mixed cultures: the carboxylate platform." Trends in biotechnology 29.2 (2011): 70-78.
Ahn, Young-Ho. "Sustainable nitrogen elimination biotechnologies: a review." Process Biochemistry 41.8 (2006): 1709-1721.
Ali, Muhammad, et al. "Rapid and successful start-up of anammox process by immobilizing the minimal quantity of biomass in PVA-SA gel beads." Water research 79 (2015): 147-157.
Alisawi, Hussein Abed Obaid. "Performance of wastewater treatment during variable temperature." Applied Water Science 10.89 (2020): 1-6.
Bae, Hyokwan, et al. "Core-shell structured poly (vinyl alcohol)/sodium alginate bead for single-stage autotrophic nitrogen removal." Chemical Engineering Journal 322 (2017): 408-416.
Beyenal, H., and A. Tanyolac. "The calculation of simultaneous effective diffusion coefficients of the substrates in a fluidized bed biofilm reactor." Water Science and Technology 29.10-11 (1994): 463-470.
Blackburne, Richard, Zhiguo Yuan, and Jürg Keller. "Partial nitrification to nitrite using low dissolved oxygen concentration as the main selection factor." Biodegradation 19.2 (2008): 303-312.
Boušková, Alžběta, et al. "Three examples of nitrogen removal from industrial wastewater using Lentikats Biotechnology." Desalination 280.1-3 (2011): 191-196.
Bulut, Emine, and Oya Şanlı. "Novel ionically crosslinked acrylamide-grafted poly (vinyl alcohol)/sodium alginate/sodium carboxymethyl cellulose pH-sensitive microspheres for delivery of Alzheimer's

(56) References Cited

OTHER PUBLICATIONS drug donepezil hydrochloride: Preparation and optimization of release conditions." Artificial Cells, Nanomedicine, and Biotechnology 44.2 (2016): 431-442.
Cao, Guo-min, et al. "Characterization of nitrifying and denitrifying bacteria coimmobilized in PVA and kinetics model of biological nitrogen removal by coimmobilized cells." Enzyme and Microbial Technology 30.1 (2002): 49-55.
Cao, Yeshi, Mark van Loosdrecht, and Glen T. Daigger. "Mainstream partial nitritation-anammox in municipal wastewater treatment: status, bottlenecks, and further studies." Applied microbiology and biotechnology 101.4 (2017): 1365-1383.
Carvajal-Arroyo, José M., et al. "Granular fermentation enables high rate caproic acid production from solid-free thin stillage." Green Chemistry 21.6 (2019): 1330-1339.
Chaitali, Mandal, et al. "Productivity improvement in xanthan gum fermentation using multiple substrate optimization." Biotechnology progress 19.4 (2003): 1190-1198.
Chen, Guanghui, et al. "Anaerobic ammonium oxidation (Anammox) sludge immobilized by waterborne polyurethane and its nitrogen removal performance-a lab scale study." Rsc Advances 5.32 (2015): 25372-25381.
Chen, Yan, et al. "Preliminary study of shortcut nitrification and denitrification using immobilized of mixed activated sludge and denitrifying sludge." Procedia Environmental Sciences 11 (2011): 1171-1176.
Chiu, Z. C., et al. "Diffusivity of oxygen in aerobic granules." Biotechnology and bioengineering 94.3 (2006): 505-513.
Omonijo, Faith A., et al. "Essential oils as alternatives to antibiotics in swine production." Animal Nutrition 4.2 (2018): 126-136.
Park, Hee-Deung, and Daniel R. Noguera. "Evaluating the effect of dissolved oxygen on ammonia-oxidizing bacterial communities in activated sludge." Water research 38.14-15 (2004): 3275-3286.
Perez-Pinera, Pablo, et al. "Synthetic biology and microbioreactor platforms for programmable production of biologics at the point-of-care." Nature communications 7.12211 (2016): 1-10.
Picioreanu, Cristian, Mark CM van Loosdrecht, and Joseph J. Heijnen. "A new combined differential-discrete cellular automaton approach for biofilm modeling: Application for growth in gel beads." Biotechnology and bioengineering 57.6 (1998): 718-731.
Prosser, J.I. "Autotrophic nitrification in bacteria." Advances in microbial physiology 30 (1990): 125-181.
Qiao, Sen, et al. "Novel single-stage autotrophic nitrogen removal via co-immobilizing partial nitrifying and anammox biomass." Chemical engineering journal 230 (2013): 19-26.
Quan, Lai Minh, et al. "Reject water treatment by improvement of whole cell anammox entrapment using polyvinyl alcohol/alginate gel." Biodegradation 22.6 (2011): 1155-1167.
Rathore, Sweta, et al. "Microencapsulation of microbial cells." Journal of food engineering 116.2 (2013): 369-381.
Samarasinghe, S. A. P. L., et al. "Fabrication of bacteria environment cubes with dry lift-off fabrication process for enhanced nitrification." Plos one 11.11 (2016): e0165839.
Sarkar, Pritish, Kaushik Ghosh, and G. K. Suraishkumar. "High hydrogen peroxide concentration in the feed-zone affects bioreactor cell productivity with liquid phase oxygen supply strategy." Bioprocess and biosystems engineering 31.4 (2008): 357-367.
Schaffner, Manuel, et al. "3D printing of bacteria into functional complex materials." Science advances 3.12 (2017): eaao6804.
Sliekers, A. Olav, et al. "Canon and Anammox in a gas-lift reactor." FEMS microbiology letters 218.2 (2003): 339-344.
"Small Compressed Gas Cartridges." 2015. Transportation Security Administration. Feb. 12, 2015. https://www.tsa.gov/travel/security-screening/whatcanibring/items/small-compressed-gas-cartridges.
Soliman, Moomen, and Ahmed Eldyasti. "Ammonia-Oxidizing Bacteria (AOB): opportunities and applications—a review." Reviews in Environmental Science and Bio/Technology 17.2 (2018): 285-321.
Sriram, G., et al. "Oxygen supply without gas-liquid film resistance to Xanthomonas campestris cultivation." Biotechnology and bioengineering 59.6 (1998): 714-723.
Stahl, David A., and José R. de la Torre. "Physiology and diversity of ammonia-oxidizing archaea." Annual review of microbiology 66 (2012): 83-101.
Stenstrom, Michael K., and Richard A. Poduska. "The effect of dissolved oxygen concentration on nitrification." Water research 14.6 (1980): 643-649.
Straka, Levi, et al. "Kinetic implication of moving warm sidestream Anaerobic ammonium oxidizing bacteria to cold mainstream wastewater." Bioresource technology 288 (2019): 121534.
Straka, Levi L., et al. "Affinity informs environmental cooperation between ammonia-oxidizing archaea (AOA) and anaerobic ammonia-oxidizing (Anammox) bacteria." The ISME journal 13.8 (2019): 1997-2004.
Strous, Mare, et al. "The sequencing batch reactor as a powerful tool for the study of slowly growing anaerobic ammonium-oxidizing microorganisms." Applied microbiology and biotechnology 50.5 (1998): 589-596.
Subramanian, S. Bala, et al. "Extracellular polymeric substances (EPS) producing bacterial strains of municipal wastewater sludge: isolation, molecular identification, EPS characterization and performance for sludge settling and dewatering." Water research 44.7 (2010): 2253-2266.
Sudarno, U., J. Winter, and C. Gallert. "Effect of varying salinity, temperature, ammonia and nitrous acid concentrations on nitrification of saline wastewater in fixed-bed reactors." Bioresource Technology 102.10 (2011): 5665-5673.
Sun, Yan, et al. "Diffusivity of oxygen into carriers entrapping whole cells." Biotechnology and bioengineering 34.1 (1989): 55-58.
Tamis, J., et al. "High-rate volatile fatty acid (VFA) production by a granular sludge process at low pH." Biotechnology and bioengineering 112.11 (2015): 2248-2255.
Urban, Carolin, et al. "Production of drop-in fuels from biomass at high selectivity by combined microbial and electrochemical conversion." Energy & Environmental Science 10.10 (2017): 2231-2244.
Delgado Vela, Jeseth, et al. "Prospects for biological nitrogen removal from anaerobic effluents during mainstream wastewater treatment." Environmental Science & Technology Letters 2.9 (2015): 234-244.
Winkler, Mari KH, et al. "Segregation of biomass in cyclic anaerobic/aerobic granular sludge allows the enrichment of anaerobic ammonium oxidizing bacteria at low temperatures." Environmental Science & Technology 45.17 (2011): 7330-7337.
Winkler, M. K., et al. "Factors influencing the density of aerobic granular sludge." Applied microbiology and biotechnology 97.16 (2013): 7459-7468.
Winkler, M-KH, R. Kleerebezem, and M. C. M. Van Loosdrecht. "Integration of anammox into the aerobic granular sludge process for main stream wastewater treatment at ambient temperatures." Water research 46.1 (2012): 136-144.
Winkler, M-KH, et al. "Selective sludge removal in a segregated aerobic granular biomass system as a strategy to control PAO-GAO competition at high temperatures." Water research 45.11 (2011): 3291-3299.
Winkler, Mari KH, et al. "Unravelling the reasons for disproportion in the ratio of AOB and NOB in aerobic granular sludge." Applied Microbiology and Biotechnology 94.6 (2012): 1657-1666.
Yeung, Timothy W., et al. "Microencapsulation of probiotics in hydrogel particles: enhancing *Lactococcus lactis* subsp. cremoris LM0230 viability using calcium alginate beads." Food & function 7.4 (2016): 1797-1804.
Cheng, Rong, Lin Lin, and Yongkui Zhang. "Hydrogen peroxide (H2O2) supply significantly improves xanthan gum production mediated by Xanthomonas campestris in vitro." Journal of Industrial Microbiology and Biotechnology 39.5 (2012).
De Man, A., van der Last, A.R.M., Lettinga, G., 1988. The use of EGSB and UASB anaerobic systems for low strength soluble and complex wastewaters at temperatures ranging from 8 to 30_C. In: Hal, E.R., Hobson, P.N. (Eds.), Proceeding of the Fifth International Symposium on Anaerobic Digestion, pp. 197-209.

(56) References Cited

OTHER PUBLICATIONS

Office Action mailed Aug. 9, 2023, issued in corresponding IL Application No. 282091, filed Oct. 14, 2019, 6 pages.
International Search Report and Written Opinion mailed Jun. 14, 2023, issued in corresponding International Application No. PCT/US2023/060180, filed Jan. 5, 2023, 10 pages.
Martinez-Cano, B., et al., "Review and Perspectives of the Use of Alginate as a Polymer Matrix for Microorganisms Applied in Agro-Industry," Molecules 2022, 27, 4248, 20 pages.
Suman, A., et al., "Development of Hydrogel based Bio-Inoculant Formulations and their Impact on Plant Biometric Parameters of Wheat (Triticum aestivum L.)," Int. Journal Curr. Microbiol. App. Sci (2016) 5(3): 890-901.
Search Report mailed Jun. 6, 2023, issued in corresponding Taiwanese Application No. 108136937, filed Oct. 14, 2019, 7 pages.
Tomaro-Duchesneau, C., et al., "Microencapsulation for the therapeutic delivery of drugs, live mammalian and bacterial cells, and other biopharmaceutics: current status and future directions," Journal of Pharmaceutics 2013, Article ID 103527, 27 pages.
Notice of Reasons for Refusal mailed Aug. 4, 2023, issued in corresponding Japanese Application No. 2021-519807, filed Oct. 14, 2019, 13 pages.
Holenda, B., et al. "Dissolved oxygen control of the activated sludge wastewater treatment process using model predictive control." Computers & Chemical Engineering 32.6 (2008): 1270-1278.
Holst, Olle, Hans Lundbäck, and Bo Mattiasson. "Hydrogen peroxide as an oxygen source for immobilized Gluconobacter oxydans converting glycerol to dihydroxyacetone." Applied microbiology and biotechnology 22.6 (1985): 383-388.
Ibrahim, M., and H. G. Schlegel. "Oxygen supply to bacterial suspensions of high cell densities by hydrogen peroxide." Biotechnology and Bioengineering 22.9 (1980): 1877-1894.
Isaka, Kazuichi, et al. "Nitrogen removal performance using anaerobic ammonium oxidation at low temperatures." FEMS microbiology letters 282.1 (2008): 32-38.
Isaka, Kazuichi, Tatsuo Sumino, and Satoshi Tsuneda. "Ammonium removal performance of anaerobic ammonium-oxidizing bacteria immobilized in polyethylene glycol gel carrier." Applied microbiology and biotechnology 76.6 (2007): 1457-1465.
Isaka, Kazuichi, et al. "Complete autotrophic denitrification in a single reactor using nitritation and anammox gel carriers." Bioresource technology 147 (2013): 96-101.
Isaka, Kazuichi, et al. "First full-scale nitritation-anammox plant using gel entrapment technology for ammonia plant effluent." Biochemical engineering journal 122 (2017): 115-122.
Jianlong, Wang, and Yang Ning. "Partial nitrification under limited dissolved oxygen conditions." Process Biochemistry 39.10 (2004): 1223-1229.
Jo, Yeadam, et al. "Treatment of low-strength ammonia wastewater by single-stage partial nitritation and anammox using upflow dual-bed gel-carrier reactor (UDGR)." Bioresource technology 304 (2020): 123023.
Johnston, Trevor G., et al. "Compartmentalized microbes and co-cultures in hydrogels for on-demand bioproduction and preservation." Nature communications 11.563 (2020): 1-11.
Jones, Peter, and A. Suggett. "The catalase-hydrogen peroxide system. Kinetics of catalatic action at high substrate concentrations." Biochemical Journal 110.4 (1968): 617-620.
Kalvelage, Tim, et al. "Oxygen sensitivity of anammox and coupled N-cycle processes in oxygen minimum zones." PloS one 6.12 (2011): e29299.
Kane, William J., J. Ledlie Klosky, and C. James Martel. "Portable wastewater treatment." Water environment & technology 13.3 (2001): 44-48.
Khanh, Dophuong, et al. "Effect of temperature on low-strength wastewater treatment by UASB reactor using poly (vinyl alcohol)-gel carrier." Bioresource technology 102.24 (2011): 11147-11154.
Kim, Jeonghwan, et al. "Anaerobic fluidized bed membrane bioreactor for wastewater treatment." Environmental science & technology 45.2 (2011): 576-581.
Kimura, Yuya, Kazuichi Isaka, and Futaba Kazama. "Tolerance level of dissolved oxygen to feed into anaerobic ammonium oxidation (anammox) reactor." Journal of Water and Environment Technology 9.2 (2011): 169-178.
Kucek, Leo A., et al. "Waste conversion into n-caprylate and n-caproate: resource recovery from wine lees using anaerobic reactor microbiomes and in-line extraction." Frontiers in microbiology 7 (2016): 1892.
Landreau, Matthieu, et al. "Effective nitrogen removal from ammonium-depleted wastewater by partial nitritation and anammox immobilized in granular and thin layer gel carriers." Water Research 183 (2020): 116078.
Landreau, Matthieu, et al. "Immobilization of active ammonia-oxidizing archaea in hydrogel beads." npj Clean Water 4.43 (2021): 1-8.
Li, Huijun, Cavin Tan, and Lin Li. "Review of 3D printable hydrogels and constructs." Materials & Design 159 (2018): 20-38.
Liu, Ying, et al. "Engineering of bio-hybrid materials by electrospinning polymer-microbe fibers." Proceedings of the National Academy of Sciences 106.34 (2009): 14201-14206.
Liu, Bin, et al. "Competition between butyrate fermenters and chain-elongating bacteria limits the efficiency of medium-chain carboxylate production." Frontiers in microbiology 11 (2020): 336.
Liu, Xian-Wei, Guo-Ping Sheng, and Han-Qing Yu. "Physicochemical characteristics of microbial granules." Biotechnology advances 27.6 (2009): 1061-1070.
Lotti, T., et al. "Physiological and kinetic characterization of a suspended cell anammox culture." Water research 60 (2014): 1-14.
Lotti, T., et al. "Pilot-scale evaluation of anammox-based mainstream nitrogen removal from municipal wastewater." Environmental technology 36.9 (2015): 1167-1177.
Lu, Yifeng, et al. "Enhancing nitrogen removal performance in a bioreactor using immobilized anaerobic ammonium oxidation sludge by polyvinyl alcohol-sodium alginate (PVA-SA)." Polish Journal of Environmental Studies 27.2 (2018): 773-778.
Magri, Albert, Matias B. Vanotti, and Ariel A. Szögi. "Anammox sludge immobilized in polyvinyl alcohol (PVA) cryogel carriers." Bioresource technology 114 (2012): 231-240.
Dos Santos, Vitor Alexandre Pires Martins. Towards the integration of oxidative and reductive activities: application to nitrogen removal by co-immobilized microorganisms. Wageningen University and Research, 2001.
McKee, D. W. "Catalytic decomposition of hydrogen peroxide by metals and alloys of the platinum group." Journal of Catalysis 14.4 (1969): 355-364.
Melin, T., et al. "Membrane bioreactor technology for wastewater treatment and reuse." Desalination 187.1-3 (2006): 271-282.
Meng, Jia, et al. "Effect of temperature on nitrogen removal and biological mechanism in an up-flow microaerobic sludge reactor treating wastewater rich in ammonium and lack in carbon source." Chemosphere 216 (2019): 186-194.
Morris, Brandon EL, et al. "Microbial syntrophy: interaction for the common good." FEMS microbiology reviews 37.3 (2013): 384-406.
Schmer M.R., Vogel K.P., Mitchell R.B., Perrin R.K. (2018) Net energy of cellulosic ethanol from switchgrass. Proceedings of the National Academy of Sciences. 105:464-469.
Pannu MW, Meinhardt KA, Bertagnolli A, Fransen SC, Stahl DA, Strand SE (2019). Nitrous oxide emissions associated with ammonia-oxidizing bacteria abundance in fields of switchgrass with and without intercropped alfalfa. Environmental Microbiology Reports, 11(727-735).
Jeffries, P., & Barea, J. M. (2001). Arbuscular mycorrhiza—a key component of sustainable plant-soil ecosystems. In Fungal Associations (pp. 95-113). Springer, Berlin, Heidelberg.
Farzaneh, M., Vierheilig, H., Lössl, A., Kaul, H. P. (2011). Arbuscular mycorrhiza enhances nutrient uptake in chickpea. Plant, Soil and Environment, 57(10), 465-470.
Mosse, B. (1977). Plant growth responses to vesicular-arbuscular mycorrhiza: Responses of Stylosanthes and Maize to inoculation in unsterile soils. New phytologist, 78(2), 277-288.
Ahanger, M. A., Hashem, A., Abd-Allah, E. F., Ahmad, P. (2014). Arbuscular mycorrhiza in crop improvement under environmental

(56) References Cited

OTHER PUBLICATIONS stress. In Emerging technologies and management of crop stress tolerance (pp. 69-95). Academic Press.
Miransari, M., Bahrami, H. A., Rejali, F., Malakouti, M. J. (2008). Using arbuscular mycorrhiza to alleviate the stress of soil compaction on wheat (*Triticum aestivuml* L.) growth. Soil Biology and Biochemistry, 40(5), 1197-1206.
USDA State Overview for Washington. Website: https://www.nass.usda.gov/Quick_Stats/Ag_Overview/stateOverview.php?state=WASHIGTON.
Ballesteros, I., Negro, M. J., Oliva, J. M., Cabañas, A., Manzanares, P., Ballesteros, M. (2006). Ethanol production from steam-explosion pretreated wheat straw. In Twenty seventh symposium on biotechnology for fuels and chemicals (pp. 496-508). Humana Press.
Barros-Rios, J., Romaní, A., Garrote, G., Ordas, B. (2015). Biomass, sugar, and bioethanol potential of sweet corn. Gcb Bioenergy, 7(1), 153-160.
Persson, T., Ren, J. L., Joelsson, E., Jönsson, A. S. (2009). Fractionation of wheat and barley straw to access high-molecular-mass hemicelluloses prior to ethanol production. Bioresource Technology, 100(17), 3906-3913.
Castellano-Hinojosa, A., Correa-Galeote, D., González-López, J., Bedmar, E. J. (2020). Effect of nitrogen fertilisers on nitrous oxide emission, nitrifier and denitrifier abundance and bacterial diversity in closed ecological systems. Applied Soil Ecology, 145, 103380.
Delgado, J. A., Khosla, R., Bausch, W. C., Westfall, D. G., Inman, D. J. (2005). Nitrogen fertilizer management based on site-specific management zones reduces potential for nitrate leaching. Journal of Soil and Water Conservation, 60 (6), 402-410.
Schimel, J. (2013). Soil carbon: microbes and global carbon. Nature Climate Change, 3(10), 867.
Wilpiszeski, R. L., Aufrecht, J. A., Retterer, S. T., Sullivan, M. B., Graham, D. E., Pierce, E. M., Elias, D. A. (2019). Soil aggregate microbial communities: Towards understanding microbiome interactions at biologically relevant scales. Applied and environmental microbiology, 85(14), e00324-19.
Bolger, A. M., Lohse, M., Usadel, B. (2014). Trimmomatic: a flexible trimmer for Illumina sequence data. Bioinformatics, 30(15), 2114-2120.
Meyer, F., Paarmann, D., D'Souza, M., Olson, R., Glass, E. M., Kubal, M., Wilkening, J. (2008). The metagenomics RAST server—a public resource for the automatic phylogenetic and functional analysis of metagenomes. BMC bioinformatics, 9(1), 386.
Tang, K., Liu, K., Jiao, N., Zhang, Y., Chen, C. T. A. (2013). Functional metagenomic investigations of microbial communities in a shallow-sea hydrothermal system. PloSone, 8(8), e72958.
Romero-Olivares, A. L., Meléndrez-Carballo, G., Lago-Lestón, A., Treseder, K. K. (2019). Soil metatranscriptomes under long-term experimental warming and drying: fungi allocate resources to cell metabolic maintenance rather than decay. Frontiers in microbiology, 10(1), 1914.
R Core Team (2014). R: A language and environment for statistical computing. R Foundation for Statistical Computing, Vienna, Austria. URL http://www.R-project.org/.
Katoh, K. and Standley, D. M. (2013). MAFFT multiple sequence alignment software version 7: improvements in performance and usability. Molecular biology and evolution, 30(4), 772-780.
Stamatakis, A. (2014). RAXML version 8: a tool for phylogenetic analysis and postanalysis of large phylogenies. Bioinformatics, 30(9), 1312-1313.
Langmead, B. and Salzberg, S. L. (2013). Fast gapped-read alignment with bowtie2. Nature Methods 9(1), 357-359.
Broberg, M., Doonan, J., Mundt, F., Denman, S., and McDonald, J. E. (2018). Integrated multi-omic analysis of host-microbiota interactions in acute oak decline. Microbiome, 6(1), 21.
Haas, B. J., Papanicolaou, A., Yassour, M., Grabherr, M., Blood, P. D., Bowden, J., MacManes, M. D. (2013). De novo transcript sequence reconstruction from RNA-seq using the Trinity platform for reference generation and analysis. Nature protocols, 8(8), 1494.

Bryant, D. M., Johnson, K., DiTommaso, T., Tickle, T., Couger, M. B., Payzin-Dogru, D., Whited, J.L. (2017). A tissue-mapped axolotl de novo transcriptome enables identification of limb regeneration factors. Cell Reports., 18(1), 762-776.
Cai, Y., Zheng, Y., Bodelier, P. L., Conrad, R., Jia, Z. (2016). Conventional methanotrophs are responsible for atmospheric methane oxidation in paddy soils. Nature communications, 7(1), 11728.
Yergeau, E., Sanschagrin, S., Maynard, C., St-Arnaud, M., Greer, C. W. (2014). Microbial expression profiles in the rhizosphere of willows depend on soil contamination. The ISME journal, 8(2), 344.
Deppe, M., Knorr, K. H., McKnight, D. M., Blodau, C. (2010). Effects of short-term drying and irrigation on $CO_2$ and $CH_4$ production and emission from mesocosms of a northern bog and an alpine fen. Biogeochemistry, 100(1-3), 89-103.
Peng, B., Sun, J., Liu, J., Dai, W., Sun, L., Pei, G., Bai, E. (2019). $N_2O$ emission from a temperate forest soil during the freeze-thaw period: A mesocosm study. Science of the Total Environment, 648, 350-357.
Dobermann, Achim R., "Nitrogen Use Efficiency—State of the Art" (2005). Agronomy & Horticulture—Faculty Publications. 316. https://digitalcommons.unl.edu/agronomyfacpub/316.
Bahram, M., Mohseni, N., Moghtader, M. (2016). An introduction to hydrogels and some recent applications. In Emerging concepts in analysis and applications of hydrogels. IntechOpen.
Wichterle O., Lím D. Hydrophilic Gels for Biological Use. (1960). Nature, 185:117-118.
Wijffels R.H., Hunik J.H., Leenen E.J.T.M., Günther A., de Castro J.M.O., Tramper J, Englund G., Bakketun Å. (1995) Effects of diffusion limitation on immobilized nitrifying microorganisms at low temperatures. Biotechnology and Bioengineering, 45, 1-9.
Ali, M., Oshiki, M., Rathnayake, L., Ishii, S., Satoh, H., Okabe, S. (2015). Rapid and successful start-up of anammox process by immobilizing the minimal quantity of biomass in PVA-SA gel beads. Water research, 79, 147-157.
Costa, L. S. D., Grazziotti, P. H., Silva, A. C., Fonseca, A. J., Gomes, Â. L. F., Grazziotti, D. C. F. S., Rossi, M. J. (2019). Alginate gel entrapped ectomycorrhizal inoculum promoted growth of cuttings of Eucalyptus clones under nursery conditions. Canadian Journal of Forest Research, 48(8), 978-985.
De Jaeger, N., De la Providencia, I. E., Rouhier, H., Declerck, S. (2011). Co-entrapment of Trichoderma harzianum and *Glomus* sp. within alginate beads: impact on the arbuscular mycorrhizal fungi life cycle. Journal of Applied Microbiology, 111(1), 125-135.
Hung, L. L. L., O'Keefe, D. M., Sylvia, D. M. (1991). Use of hydrogel as a sticking agent and carrier for vesicular-arbuscular mycorrhizal fungi. Mycological Research, 95(4), 427-429.
Pitaktamrong, P., Kingkaew, J., Yooyongwech, S., Cha-um, S., Phisalaphong, M. (2018). Development of arbuscular mycorrhizal fungi-organic fertilizer pellets encapsulated with alginate film. Engineering Journal, 22(6), 65-79.
Vassilev, N., Vassileva, M., Azcon, R., Medina, A. (2001). Preparation of gel-entrapped mycorrhizal inoculum in the presence or absence of Yarowia lipolytica. Biotechnology letters, 23(11), 907-909.
Coussa, R.G. et al. Microencapsulated *Saccharomyces cerevisiae* col. Bioreactor for Potential Use in Renal Failure Uremia, Artificial Cells, Blood Substitutes, and Biotechnology, 40;1-2 (2012) 103-112.
Geiser, L., Patel-Weynand, T., Marsh, A., Mafune K., Vogt, D. Chapter 10: Challenges and Opportunities. In: Sustainable Forest Management Research—Forest and rangeland soils of the United States under changing conditions: A comprehensive science synthesis. National Soils Assessment. Anticipated release 2020.
Mafune, K., Godfrey, B., Vogt, K., and Vogt, D (2019). A rapid approach to profiling diverse fungal communities using the MinION™ nanopore sequencer. Biotechniques, 68(2), 72-78.
Service, R. (2018). Ammonia—A Renewable Fuel Made From Sun, Air, and Water—Could Power the Globe Without Carbon. Science, aau7489.
Fagodiya, R. K., Pathak, H., Kumar, A., Bhatia, A., Jain, N. (2017). Global temperature change potential of nitrogen use in agriculture: A 50-year assessment. Scientific reports, 7(44928).

(56) References Cited

OTHER PUBLICATIONS

Dodds, W. K. et al. (2009) Eutrophication of U.S. freshwaters: analysis of potential economic damages. Environmental Science and Technology, 43(12-19).
Sinha, E., Michalak, A. M., Balaji, V. (2017). Eutrophication will increase during the 21st century as a result of precipitation changes. Science, 357(6349), 405-408.
Liu, J., Ma, K., Ciais, P., Polasky, S. (2016). Reducing human nitrogen use for food production. Scientific reports, 6, 30104.
Frankow-Lindberg, B.E., A.S. Dahlin. (2013). N2 fixation, N transfer, and yield in grassland communities including a deep-rooted legume or non-legume species. Plant and Soil, 370, 567-581.
Burton, J.C. (1972). Nodulation and symbiotic nitrogen fixation. In C.H. Hanson (Ed.), Alfalfa Science and Technology (Monograph 15; pp. 229-246). Madison, WI: American Society of Agronomy.
Reed S.C., Cleveland C.C., Townsend A.R. (2011). Functional ecology of free-living nitrogen fixation: a contemporary perpective. Annu Rev Ecol Evol Syst 42: 489-512.
Norman, J. S., Friesen, M. L. (2017). Complex N acquisition by soil diazotrophs: how the ability to release exoenzymes affects N fixation by terrestrial free-living diazotrophs. The ISME journal, 11(2), 315-326.
Islam, M. R., Sultana, T., Joe, M. M., Yim, W., Cho, J. C., Sa, T. (2013). Nitrogen-fixing bacteria with multiple plant growth-promoting activities enhance growth of tomato and red pepper. Journal of basic microbiology, 53(12), 1004-1015.
Barea, J. M., Azcón, R., Azcón-Aguilar, C. (2002). Mycorrhizosphere interactions to improve plant fitness and soil quality. Antonie van leeuwenhoek, 81(1-4), 343-351.
Paul, K., Saha, C., Nag, M., Mandal, D., Naiya, H., Sen, D., . . . Naskar, N. (2020). A tripartite interaction among the basidiomycete Rhodotorula mucilaginosa, N2-fixing endobacteria, and rice improves plant nitrogen nutrition. The Plant Cell, 32(2), 486-507.
Gómez-Brandón, M., Probst, M., Siles, J. A., Peintner, U., Bardelli, T., Egli, M., Ascher-Jenull, J. (2020). fungal communities and their association with nitrogen-fixing bacteria affect early decomposition of Norway spruce deadwood. Scientific reports, 10(1), 1-11.
Könneke, Martin, et al. "Isolation of an autotrophic ammonia-oxidizing marine archaeon." Nature 437.22 (2005): 543-546.
Isaka, Kazuichi, et al. "Growth characteristic of anaerobic ammonium-oxidizing bacteria in an anaerobic biological filtrated reactor." Applied microbiology and biotechnology 70.1 (2006): 47-52.
Matsushige, K., et al. "The effects of temperature on anaerobic filter treatment for low-strength organic wastewater." Environmental Technology 11.10 (1990): 899-910.
Smith, K.A. (2017). Changing views of nitrous oxide emissions from agricultural soil: key controlling processes and assessment at different spatial scales. European Journal of Soil Science, 68(2), 137-155.
Fageria, N. K., & Baligar, V. C. (2005). Enhancing nitrogen use efficiency in crop plants. Advances in agronomy, 88, 97-185.
Ghignone, S., Salvioli, A., Anca, I., Lumini, E., Ortu, G., Petiti, L., Bonfante, P. (2012). The genome of the obligate endobacterium of an AM fungus reveals an interphylum network of nutritional interactions. The ISME journal, 6(1), 136-145.
Desai, N. P., et al. "Interpenetrating polymer networks of alginate and polyethylene glycol for encapsulation of islets of Langerhans." Journal of microencapsulation 17.6 (2000): 677-690.
Gong, Jian Ping. "Friction and lubrication of hydrogels—its richness and complexity." Soft matter 2.7 (2006): 544-552.
De Almeida Fernandes, Luyara, et al. "Effect of temperature on microbial diversity and nitrogen removal performance of an anammox reactor treating anaerobically pretreated municipal wastewater." Bioresource technology 258 (2018): 208-219.
De Kreuk, M. K., N. Kishida, and M. C. M. Van Loosdrecht. "Aerobic granular sludge-state of the art." Water Science and Technology 55.8-9 (2007): 75-81.

De Smet, Stefaan, et al. "Gut antibacterial effects of C7 and C9 carboxylic acids in the diet of piglets." Journal of Animal Science 94.suppl_3 (2016): 54-57.
Desai, N. P., et al. "Interpenetrating polymer networks of alginate and polyethylene glycol for encapsulation of islets of angerhans." Journal of microencapsulation 17.6 (2000): 677-690.
Ding, Shuang, et al. "Ecological characteristics of anaerobic ammonia oxidizing bacteria." Applied microbiology and biotechnology 97.5 (2013): 1841-1849.
Dolejs, Igor, et al. "Nitrogen removal by co-immobilized anammox and ammonia-oxidizing bacteria in wastewater treatment." Catalysts 9.523 (2019): 1-8.
French, Elizabeth, et al. "Ecophysiological characterization of ammonia-oxidizing archaea and bacteria from freshwater." Applied and Environmental Microbiology 78.16 (2012): 5773-5780.
Furukawa, Kenji, et al. "Innovative treatment system for digester liquor using anammox process." Bioresource Technology 100.22 (2009): 5437-5443.
Fux, Christian, et al. "Biological treatment of ammonium-rich wastewater by partial nitritation and subsequent anaerobic ammonium oxidation (anammox) in a pilot plant." Journal of biotechnology 99.3 (2002): 295-306.
Grant, Shannon, and Kwan-Chow Lin. "Effects of temperature and organic loading on the performance of upflow anaerobic sludge blanket reactors." Canadian journal of civil engineering 22.1 (1995): 143-149.
Guo, Jianhua, et al. "Long-term effect of dissolved oxygen on partial nitrification performance and microbial community structure." Bioresource technology 100.11 (2009): 2796-2802.
Harroff, Lauren A., et al. "Inactivation of Ascaris eggs in human fecal material through in situ production of carboxylic acids." Environmental Science & Technology 51.17 (2017): 9729-9738.
Hellinga, C. S. A. A. J. C., et al. "The Sharon process: an innovative method for nitrogen removal from ammonium-rich waste water." Water science and technology 37.9 (1998): 135-142.
Isaka, Kazuichi, et al. "Growth characteristic of anaerobic ammonium-oxidizing bacteria in an anaerobic biological iltrated reactor." Applied microbiology and biotechnology 70.1 (2006): 47-52.
Lotti, T., et al. "The effect of nitrite inhibition on the anammox process." Water research 46.8 (2012): 2559-2569.
Jo, Yun-Suk; et al; "Encapsulation of Bovine Serum Albumin in Temperature-Programmed "Shell-in-Shell" Structures" Macromolecule Rapid Communications, 24, 957-962, 2003 (Year: 2003).
Lim, Trisna; "Microcapsules immobilizing activated charcoal and metabolically induced Lactobacillus acidophilus cells as potential oral renal failure therapy formulation" Masters Thesis, McGill University, Feb. 2006 (Year: 2006).
Papadimitriou, Sofia; et al; "Chitosan-g-PEG nanoparticles ionically crosslinked with poly(glutamic acid) and tripolyphosphate as protein delivery systems" International Journal of Pharmaceutics, 430, 318-327, 2012 (Year: 2012).
Qiu, Bo; et al; "A hydrogel prepared by in situ cross-linking of a thiol-containing poly(ethylene glycol)-based copolymer: a new biomaterial for protein drug delivery" Biomaterials, 24, 11-18, 2003 (Year: 2003).
Quellec, P; et al; "Protein encapsulation within polyethylene glycol-coated nanospheres" Journal of Biomedical Materials Research, 42, 42-54, 1998 (Year: 1998).
Dolej, Igor, et al. "Nitrogen removal by co-immobilized anammox and ammonia-oxidizing bacteria in wastewater treatment." Catalysts 9.523 (2019): 1-8.
Indonesian Stage 1 Substantive Examination Report received for Indonesian Application No. P00202102530 dated Nov. 30, 2022; 6 pages total (including English Translation).
Notice of Allowance for U.S. Appl. No. 17/284,759, mailed Nov. 7, 2024.

* cited by examiner

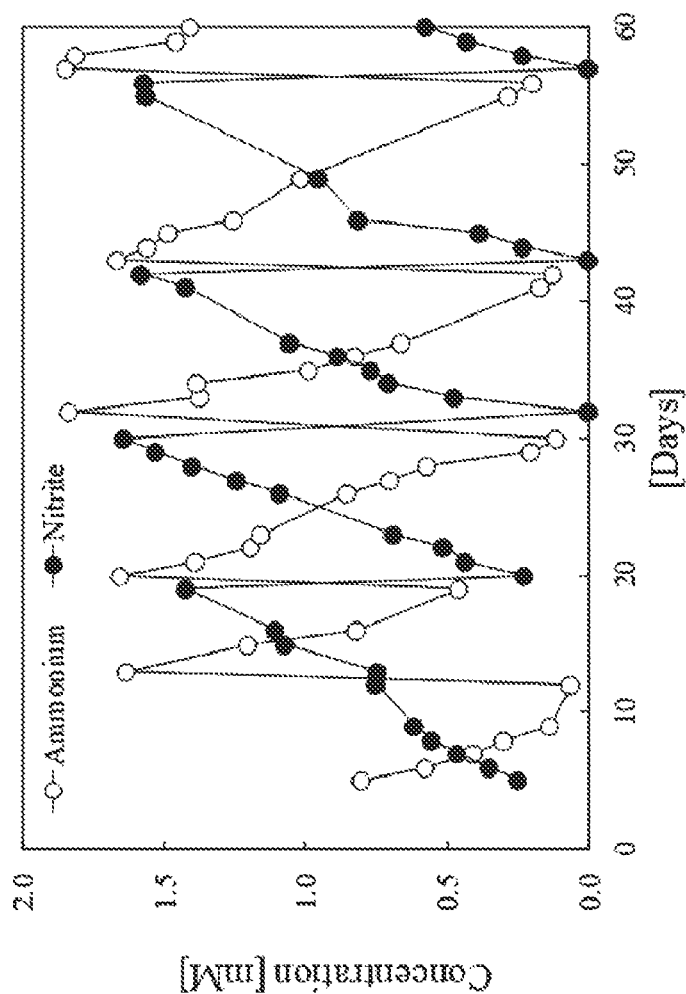
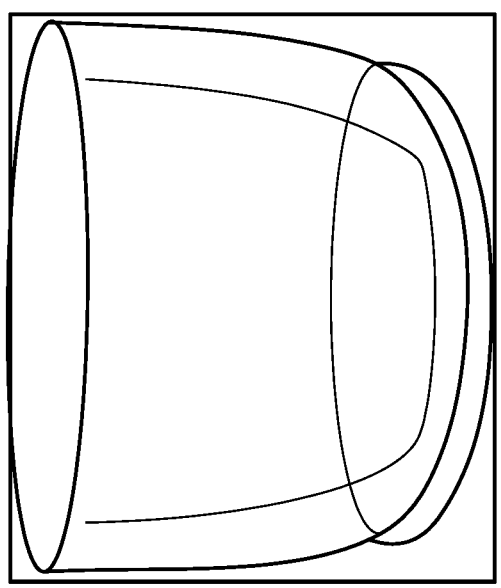
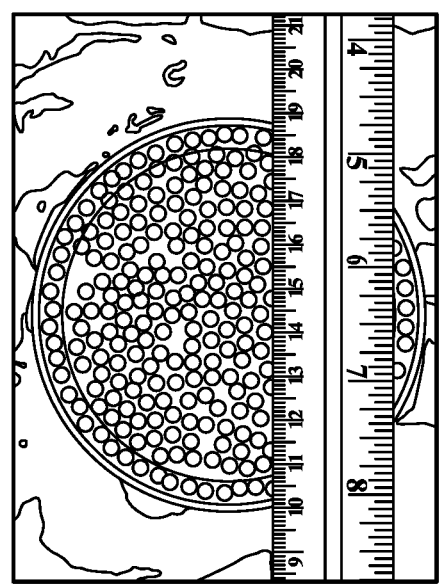
FIG. 4A
FIG. 4B
FIG. 4C

HYDROGELS FOR THE ENTRAPMENT OF BACTERIA

CROSS-REFERENCE TO RELATED APPLICATION

This application claims the benefit of U.S. Provisional Application 62/914,884, filed Oct. 14, 2019, the disclosure of which is incorporated herein by reference in its entirety.

STATEMENT OF GOVERNMENT LICENSE RIGHTS

This invention was made with government support under Grant No. HR0011-17-2-0064, awarded by the Defense Advanced Research Projects Agency. The government has certain rights in the invention.

BACKGROUND

The discharge of nitrogen-rich wastewater into receiving water bodies contributes to eutrophication, oxygen depletion, and associated degradation of environmental quality. The ammonium concentration in typical untreated domestic wastewaters fluctuates between 10 and 45 mg/L but can be as high as 600-1000 mg/L in the reject water (sidestream) of anaerobic digesters. The removal of ammonium as nitrogen gas via conventional nitrification and denitrification is an energy intensive process, but the combination of aerobic and anaerobic ammonia-oxidizing bacteria (AOB and Anammox bacteria, respectively) can reduce this aeration demand by 60%. AOB are chemolitho-autotrophic microorganisms that oxidize ammonia to nitrite which is used by Anammox along with ammonium to anaerobically form dinitrogen gas. However, in order to successfully pair AOB and Anammox, the conversion of nitrite into nitrate by nitrite-oxidizing bacteria (NOB) must be suppressed. The different strategies for suppressing nitrite oxidation in sidestream wastewater have included maintaining DO concentration at microaerophilic levels, operating at high pH values (pH 7.5-8) to take advantage of free ammonia inhibition of NOB, or operating at a high temperature (ca. 30° C.) and short hydraulic retention time. While Anammox has been successfully applied in sidestream processes, the implementation in the cold ammonium-depleted mainstream remains a bottleneck. Thus, the use of higher biomass concentrations or ammonia-oxidizing archaea (AOA) having a much higher affinity for ammonia offer new opportunities for mainstream operations. While the implementation of Anammox with AOA is not yet established, the co-localization of AOB and Anammox in dense biofilms such as granular sludge reactor is common practice in sidestream treatment. Natural granule formation in sludge reactors is promoted by operating conditions that select for the natural aggregation of slow growing microorganisms (such as Anammox bacteria and AOB) into near-spherical granules of bacteria bound together by a matrix of exopolysaccharides. In comparison to activated sludge (AS), granular sludge offers several advantages, such as better sludge settleability, higher retention time, and greater resistance to treatment fluctuations. However, autotrophic microorganisms are slow growing with a doubling time of up to 11 days, which will be lowered even further under mainstream conditions hence presenting a challenge to reactor start-up.

In the recent years, cell entrapment in polymer matrices has been used as an alternative to natural granules due to the capacity of hydrogels to retain high metabolic activity, be produced rapidly, offer good diffusion of substrates and metabolites, and retain biomass at the high concentrations required for treating high ammonia loadings at low temperature. Several strategies using carriers with different combinations of polymers and geometries have been investigated for the treatment of wastewater, including single and double-layered PVA beads, PVA discs, or PEG cubes. Overall, studies reported performances often in the range of 70-95% of total nitrogen removal efficiency with ammonium-rich wastewater. While the effect of operating parameters on performances is known for high strength wastewater, the functioning of hydrogels remains poorly described for ammonium-deplete conditions and other applications.

Thus, a need exists for alternative substrates and methods for establishing high biomass retention of bacteria, including wastewater processing microorganisms such as aerobic and anaerobic ammonia oxidizers.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides a composition for reducing the concentration of one or more contaminants in a fluid, comprising:

a plurality of particles comprising a hydrogel core and one or more colonies of microorganisms associated with the hydrogel, wherein the microorganisms are configured to remove one or more contaminants, and wherein the hydrogel core comprises (a) alginate and a polymer of one or more acrylate derivatives of polyethylene glycol (PEG); or (b) polyvinyl alcohol (PVA), alginate, and carboxymethyl cellulose (CMC).

In some embodiments, the fluid is wastewater, urine, or gut fluids. In some embodiments, the contaminant is urea, sweat, or a combination thereof.

In some embodiments, the one or more colonies of microorganisms comprise active autotrophic microorganisms, active heterotrophic microorganisms, or a combination thereof. In some embodiments, the microorganisms are bacteria or archaea. In some embodiments, the microorganisms comprise anaerobic microorganisms, aerobic microorganisms, or a combination thereof. In some embodiments, the microorganisms comprise ammonia-oxidizing bacteria. In some embodiments, the microorganisms are *Nitrosomonas europaea, Nitrososphaera vienensis*, commamox type *Nitrospira*, or a combination thereof.

In some embodiments, the hydrogel is formed by polymerization of a mixture comprising one or more acrylate derivatives of polyethylene glycol (PEG) and alginate. In some embodiments, the one or more acrylate derivatives of polyethylene glycol (PEG) is PEG acrylate, PEG methacrylate, N-PEG acrylamide, N-PEG methacrylamide, PEG diacrylate (PEGDA), PEG dimethacrylate (PEGDMA) or a combination thereof.

In some embodiments, the mixture further comprises a photoactivator. In some embodiments, the hydrogel is cross-linked. In some embodiments, the hydrogel comprises polyvinyl alcohol, sodium alginate, and carboxymethyl cellulose.

In some embodiments, the plurality of particles comprise a shell surrounding the core. In some embodiments, the shell is bound to the core by covalent bonding, ionic bonding, or a combination thereof. In some embodiments, the shell comprises SBQ-PVA. In some embodiments, the shell comprises PVA and SBQ-PVA. In some embodiments, the shell comprises SBQ-PVA. shell is formed by contacting a particle comprising the hydrogel with a composition comprising SBQ-PVA and optionally one or more fillers and/or one or more microorganisms. In some embodiments, the shell allows diffusion of the one or more contaminants into the core.

In some embodiments, the composition further comprises one or more oxygen-releasing catalysts. In some embodiments, the one or more oxygen-releasing catalysts is in the shell. In some embodiments, the one or more oxygen-releasing catalysts is a transition metal catalyst such as platinum or palladium catalyst. In some embodiments, the one or more oxygen-releasing catalysts is a catalyst that catalyzes decomposition of a peroxide into oxygen. In some embodiments, the peroxide is hydrogen peroxide.

In some embodiments, the core and shell comprise microorganisms, wherein the microorganisms in the shell and the microorganisms in the core are the same or different. In some embodiments, the microorganisms in the core are anaerobic microorganisms and the microorganisms in the shell are aerobic microorganisms.

In some embodiments, the plurality of particles has a diameter from about 0.1 mm to about 5 mm.

In another aspect, the disclosure provides a method for removal of one or more contaminants from a fluid comprising contacting the fluid comprising one or more contaminants with the composition of the disclosure.

In another aspect, the disclosure provides a system for removal of one or more contaminants from a fluid comprising the composition of the disclosure.

In another aspect, the disclosure provides a particle comprising a core and a shell, wherein the core comprises polyvinyl alcohol (PVA), alginate, and carboxymethyl cellulose (CMC) and wherein the shell comprises SBQ-PVA.

In some embodiments, the shell comprises one or more fillers. In some embodiments, the one or more fillers is silica gel particles, microfibrillated cellulose, nanocellulose rods, a fiber forming polymer such as Kevlar, carbon nanotubes, nanoparticles of high aspect ratio, or a combination thereof.

In some embodiments, the shell comprises one or more microorganisms. In some embodiments, the core comprises one or more microorganisms.

In some embodiments, the shell comprises one or more oxygen-releasing catalysts. In some embodiments, the one or more oxygen-releasing catalysts is a transition metal catalyst. In some embodiments, the one or more oxygen-releasing catalysts is platinum or palladium catalyst. In some embodiments, the one or more oxygen-releasing catalysts is a catalyst that catalyzes decomposition of a peroxide into oxygen. In some embodiments, the peroxide is hydrogen peroxide.

In another aspect, the disclosure provides a particle comprising a hydrogel core and a shell, wherein the hydrogel comprises alginate and a polymer comprising monomeric units derived from one or more acrylate derivatives of polyethylene glycol (PEG) and wherein the shell comprises SBQ-PVA.

In some embodiments, the polymer further comprises monomeric units derived from acrylic acid or methacrylic acid. In some embodiments, the polymer is crosslinked. In some embodiments, the one or more acrylate derivatives of polyethylene glycol (PEG) is PEG acrylate, PEG methacrylate (PEGMA), N-PEG acrylamide, N-PEG methacrylamide, PEG diacrylate (PEGDA), PEG dimethacrylate (PEGDMA) or a combination thereof.

In some embodiments, the shell comprises one or more fillers. In some embodiments, the one or more fillers is silica gel particles, microfibrillated cellulose, nanocellulose rods, a fiber forming polymer such as Kevlar, carbon nanotubes, nanoparticles of high aspect ratio, or a combination thereof.

In another aspect, the disclosure provides a method for forming a hydrogel particle, the method comprising:
 forming a droplet of a first solution comprising alginate and one or more acrylate derivatives of polyethylene glycol (PEG) and one or more polymerization initiators and
 dropping the droplet into a second solution comprising calcium or barium ions.

In some embodiments, the one or more acrylate derivatives of polyethylene glycol (PEG) is PEG acrylate, PEG methacrylate, N-PEG acrylamide, N-PEG methacrylamide, PEG diacrylate (PEGDA), PEG dimethacrylate (PEGDMA) or a combination thereof.

In some embodiments, the second solution is anoxic. In some embodiments, the first solution comprises about 0.5 wt % to about 5 wt % sodium alginate. In some embodiments, the first solution comprises one or more microorganisms.

In some embodiments, the one or more polymerization initiators is a photoinitiator. In some embodiments, the photoinitiator is 2-hydroxy-4'-(2-hydroxyethoxy)-2-methyl-propiophenone (Irgacure 2959) or lithium phenyl-2,4,6-trimethylbenzoylphisphinate (LAP). In some embodiments, the dropping the droplet is done under UV light. In some embodiments, the first solution comprises ammonium persulfate (APS) and tetramethyl ethylene diamine (TEMED).

In some embodiments, the first solution comprises 10 wt % to 60 wt % of PEG diacrylate (PEGDA) or PEG dimethacrylate (PEGDMA).

In some embodiments, the particle has a diameter from about 0.1 mm to about 5 mm, from about 0.1 mm to about 3 mm, from about 1 mm to about 5 mm, or from about 0.5 mm to about 2 mm.

In some embodiments, the first solution comprises acrylic acid, methacrylic acid, or a combination thereof.

In some embodiments, the method further comprising contacting the hydrogel particle with a solution of SBQ-PVA coating the particle with a shell comprising SBQ-PVA.

In another aspect, the disclosure provides a particle formed by the methods disclosed herein.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 4A-4C demonstrate consumption and production of ammonium and nitrite in batch culture inoculated by immobilized enriched AOA culture, AC-2 at 30° C.

FIG. 14A shows SBQ-PVA/fillers mixture with blue pigment. FIG. 14B shows hydrogel beads added to the SBQ-PVA mixture, t=0. FIG. 14C shows hydrogel beads added to the SBQ-PVA mixture, t=1 min. FIG. 14D shows hydrogel beads added to the SBQ-PVA mixture, t=3 min. FIG. 14E shows hydrogel beads added to the SBQ-PVA mixture, t=4 min. FIG. 14F shows hydrogel beads added to the SBQ-PVA mixture, t=4+ min.

DETAILED DESCRIPTION

Figure 1A:
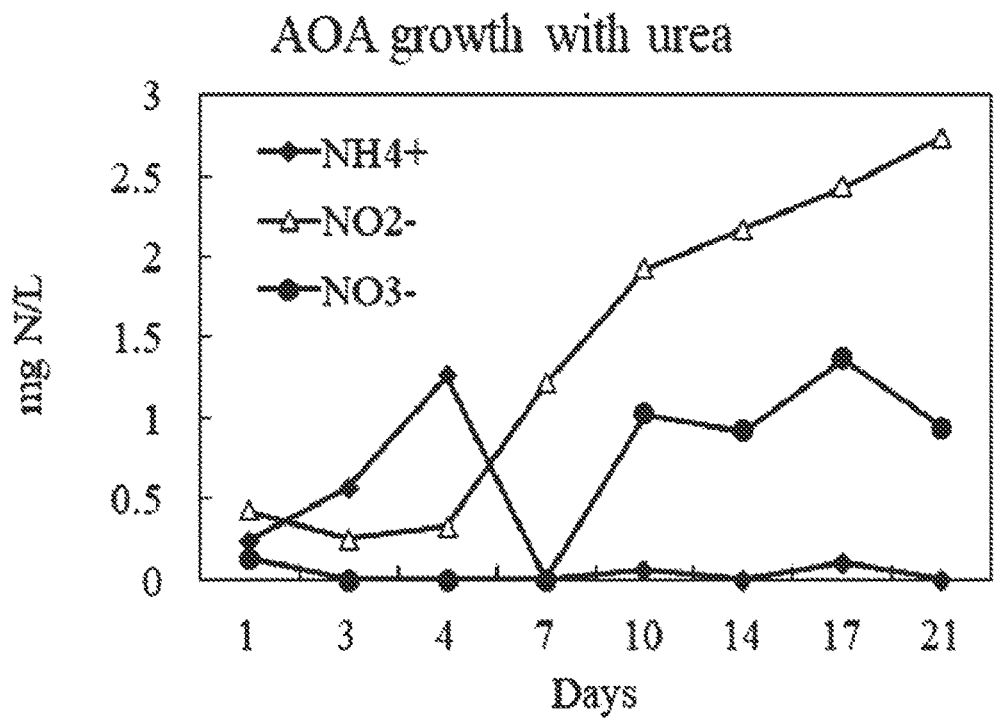
FIG. 1 demonstrates ammonia oxidation followed by urea hydrolysis by AOA (1A) and AOB (1B) microorganisms.

The present disclosure describes the fabrication and use of compositions, such as hydrogel beads, for entrapment of microorganisms useful in processing wastewater streams and other applications.

This, in one aspect, the disclosure provides a composition for reducing the concentration of one or more contaminants in a fluid, comprising a plurality of particles comprising a hydrogel core and one or more colonies of microorganisms associated with the hydrogel, wherein the microorganisms are configured to remove one or more contaminants. The hydrogels included in the particles/compositions of the disclosure comprise alginate and (a) a polymer of one or more acrylate derivatives of polyethylene glycol (PEG); or (b) polyvinyl alcohol (PVA) and a polymer comprising negatively charged groups, such as carboxymethyl cellulose (CMC).

The colonies of microorganisms entrapped in or associated with the composition of the disclosure typically comprise active autotrophic microorganisms, active heterotrophic microorganisms, or a combination thereof. In some embodiments, the microorganisms are bacteria or archaea. The microorganisms useful for inclusion in the compositions of the disclosure can comprise anaerobic microorganisms, aerobic microorganisms, or a combination thereof. In some embodiments, the microorganisms comprise ammonia-oxidizing bacteria. Non-limiting examples of the microorganisms useful for inclusion in the compositions disclosed herein include *Nitrosomonas europaea, Nitrososphaera vienensis*, commamox type *Nitrospira*, or a combination thereof.

The compositions disclosed herein are configured to decontaminate a fluid by removing or reducing the concentration of one or more contaminants from a fluid by contacting the fluid to be decontaminated with a composition of the disclosure for a sufficient period of time. Suitable fluids that can be decontaminated using the methods of the disclosure include wastewater, urine, and gut fluids. Contaminants that can be removed or reduced using the compositions include urea, sweat, proteins, and combinations thereof.

In some embodiments, the hydrogel is formed by polymerization of a mixture comprising one or more acrylate derivatives of polyethylene glycol (PEG) and alginate, such as sodium alginate (SA). Any suitable polymerizable derivatives of PEG, such as acrylate derivatives of polyethylene glycol, can be used to generate the hydrogels of the disclosed compositions. Polymerizable derivatives of PEG also include multi-arm PEG acrylates and PEG acrylamides, for example, 4-Arm PEG-Acrylamide and 4-Arm PEG-Acrylate such as those available from Creative PEGWorks. In some embodiments, the one or more acrylate derivatives of polyethylene glycol (PEG) is PEG acrylate, PEG methacrylate, N-PEG acrylamide, N-PEG methacrylamide, PEG diacrylate (PEGDA), PEG dimethacrylate (PEGDMA), or a combination thereof. Any suitable size PEG can be used; for example, in some embodiments, the PEG of the polymerizable PEG derivative is PEG 400, PEG 500, PEG 1000, PEG 2000, PEG 6000, PEG 8000, and the like. Other monomers that can be co-polymerized with the acrylate derivatives of polyethylene glycol can be included in the mixture. In some embodiments, the mixture can comprise a combination of one or more acrylate derivatives of polyethylene glycol, such as PEG acrylate, and acrylamide and/or methacrylamide, allowing creation of a tougher, more flexible gel. In some embodiments, acrylic acid can be added to the mixture and co-polymerized with the one or more acrylate derivatives of polyethylene glycol, resulting in a hydrogel comprising negatively charged groups (—COOH). Inclusion of the negatively charged groups in the hydrogel can enhance the interaction of the hydrogel with a coating or shell comprising a positively charged polymer, such as SBQ-PVA, as described below.

In some embodiments, the mixtures used to form the hydrogels of the disclosure can further comprise one or more activators of polymerization/crosslinking. In some embodiments, the activator of polymerization is a photoinitiator. Suitable photoinitiators include 2-hydroxy-4'-(2-hydroxyethoxy)-2-methylpropiophenone (Irgacure 2959), lithium phenyl-2,4,6-trimethylbenzoylphisphinate (LAP), and the like. In some embodiments, the one or more activators of polymerization is a chemical catalyst, such as ammonium persulfate (APS) and tetramethyl ethylene diamine (TEMED). In some embodiments, one or more chemical catalysts can be combined with one or more photoinitiators to accomplish the formation of the hydrogels. Thus, in some embodiments, where the mixture comprises one or more crosslinking monomers, such as PEG diacrylate (PEGDA) or PEG dimethacrylate (PEGDMA), the hydrogels can be crosslinked.

In some embodiments, the hydrogel of the particles of the disclosure comprises polyvinyl alcohol, alginate, and a negatively charged component, such as carboxymethyl cellulose (CMC).

In some embodiments, the hydrogel of the compositions of the disclosure comprises calcium or barium alginate, for example, formed by contacting a precursor mixture comprising sodium alginate with a solution comprising calcium, magnesium, or barium ions.

The particles of the composition of the disclosure can further comprise a shell surrounding the hydrogel core. In some embodiments, the shell is bound to the core by covalent bonding, ionic bonding, or a combination thereof. In some embodiments, the shell comprises a positively charged derivative of poly(vinyl alcohol), such as poly(vinyl alcohol) (PVA) substituted with styrylpyridinium (SBQ) (SBQ-PVA). In some embodiments, the shell is formed by contacting a particle comprising the hydrogel with a composition comprising SBQ-PVA, such as a mixture of PVA and SBQ-PVA.

In some embodiments, the shell can optionally comprise one or more fillers. Fillers can be added to the SBQ-PVA-containing composition prior to forming the shell and/or can be associated with the shell after the shell formation. In some embodiments, it is advantageous to including a filler, such as a particulate substance, in the shell layer. Because the diameter of the hydrogel particles can define a minimum thickness of the layer being formed, addition of the fillers can regulate the thickness of the shell. If the particulate substance is fibrous, such as a cellulose, addition of such particulate substance can also increase the strength of the shell. In some embodiments, wherein the filler is silica particles, such filler can chemically bond to the PVA, for example, through borate crosslinks, when borate is present in the core. In some embodiments, the filler can be diatomaceous earth, such as food grade diatomaceous earth comprised of the shells of diatoms, that include wide and flat particles with pores or needle-like rods with an average particle size of about 20 microns. Other fillers suitable for inclusion in the shell of the particles disclosed herein include microfibrillated celluose, nanocellulose rods, microfibrillated synthetic fiber-forming polymers like Kevlar, carbon nanotubes, such as surface-modified carbon nanotubes (CNT), or any number of nanoparticles of high aspect ratio (e.g., particles having whisker-like shape).

In some embodiments, the compositions disclosed herein further comprise one or more oxygen-releasing catalysts. The oxygen-releasing catalysts can reside in the core of the hydrogel particle, the shell of the hydrogel particle, or can be associated with a second particle. In some embodiments, the one or more oxygen-releasing catalysts is in the shell. Any suitable oxygen-releasing catalysts can be used in the compositions of the disclosure. In some embodiments, the one or more oxygen-releasing catalysts is a catalyst that catalyzes decomposition of a peroxide into oxygen. Suitable peroxides can include organic and/or inorganic peroxides. In some embodiments, the peroxide is hydrogen peroxide. In some embodiments, the one or more oxygen-releasing catalysts is a transition metal catalyst, such as platinum or palladium catalyst.

In some embodiments, the shell can optionally comprise one or more microorganisms, which can be the same or different from the microorganisms present in the core of the particle. In some embodiments, the shell allows diffusion of the one or more contaminants into the core, where it can be metabolized by one or more colonies of microorganisms residing in the core. In some embodiments, the core and shell comprise microorganisms, wherein the microorganisms in the shell and the microorganisms in the core are the same or different. In some embodiments, the microorganisms in the shell and the microorganisms in the core are different. In some embodiments, the microorganisms in the core are anaerobic microorganisms and the microorganisms in the shell are aerobic microorganisms.

In some embodiments, the microorganisms, e.g., anaerobic microorganisms and aerobic microorganisms, can be allowed to colonize the particles of the compositions of the disclosure after the particle formation. In some embodiments, the anaerobic microorganisms will predominantly colonize the core of the particle, and the aerobic microorganisms will reside predominantly closer to the surface of the particle, i.e., in the shell. In some embodiments, the microorganisms can be present in the precursor mixture used to form the hydrogel of the particle, such as a mixture comprising alginate and one or more acrylate derivatives of polyethylene glycol (PEG); or a mixture comprising alginate, polyvinyl alcohol (PVA) and a polymer comprising negatively charged groups, such as carboxymethyl cellulose (CMC). In some embodiments, In some embodiments, the particles have a diameter from about 0.1 mm to about 5 mm, from about 0.1 mm to about 4 mm, from about 0.1 mm to about 3 mm, from about 0.1 mm to about 2 mm. In some embodiments, the core of the particles has a diameter from about 0.1 mm to about 5 mm, from about 0.1 mm to about 4 mm, from about 0.1 mm to about 3 mm, from about 0.1 mm to about 2 mm.

In another aspect, the disclosure provides a method for removal of one or more contaminants from a fluid comprising one or more contaminants, the method comprising contacting the fluid with a composition in the disclosure.

In another aspect, the disclosure provides a system for removal of one or more contaminants from a fluid comprising the composition of the disclosure.

In another aspect, the disclosure provides a particle comprising a core and a shell, wherein the core comprises polyvinyl alcohol (PVA), alginate, and carboxymethyl cellulose (CMC), and wherein the shell comprises a positively charged polymer, such as SBQ-PVA. In some embodiments, the shell is crosslinked. In some embodiments, the core is crosslinked. In some embodiments, the core comprises insoluble salt of alginic acid, such as calcium alginate, magnesium alginate, or barium alginate.

In some embodiments, the shell comprises one or more fillers such as the fillers described above. Suitable fillers include silica gel particles, diatomaceous earth, microfibrillated cellulose, nanocellulose rods, a fiber-forming polymer such as Kevlar, carbon nanotubes (CNT), nanoparticles with a high aspect ratio, or a combination thereof.

In some embodiments, the shell comprises one or more oxygen-releasing catalysts. In some embodiments, the one or more oxygen-releasing catalysts is a catalyst that catalyzes decomposition of a peroxide, such as hydrogen peroxide, into oxygen. In some embodiments, the one or more oxygen-releasing catalysts is a transition metal catalyst, such as platinum or palladium catalyst.

In some embodiments of the methods, the particle can comprise one or more microorganisms. In some embodiments, the shell of the particle comprises one or more microorganisms. In some embodiments, the core comprises one or more microorganisms.

In some embodiments of the methods, the core and the shell comprise one or more microorganisms, which can be the same or different. Microorganisms suitable for inclusion into the particles include those described above.

In another aspect, the disclosure provides a particle comprising a hydrogel core and a shell, wherein the hydrogel core comprises alginate and a polymer comprising monomeric units derived from one or more polymerizable PEG derivatives, such as acrylate derivatives of polyethylene glycol (PEG), and the shell comprises SBQ-PVA. In some embodiments, the one or more acrylate derivatives of polyethylene glycol (PEG) is PEG acrylate, PEG methacrylate (PEGMA), N-PEG acrylamide, N-PEG methacrylamide, PEG diacrylate (PEGDA), PEG dimethacrylate (PEGDMA), or a combination thereof. In some embodiments, the polymer of the core further comprises monomeric units derived from acrylic acid or methacrylic acid.

In some embodiments, the polymer is crosslinked. In some embodiments, the shell is crosslinked. In some embodiments, the core is crosslinked. In some embodiments, the core comprises insoluble salt of alginic acid, such as calcium alginate, magnesium alginate, or barium alginate.

In some embodiments, the shell comprises one or more fillers such as the fillers described above. Exemplary fillers include silica gel particles, diatomaceous earth, microfibrillated cellulose, nanocellulose rods, fiber-forming polymers such as Kevlar, carbon nanotubes (CNT), nanoparticles with a high aspect ratio, and combinations thereof.

In some embodiments, the shell comprises one or more oxygen-releasing catalysts. In some embodiments, the one or more oxygen-releasing catalysts is a catalyst that catalyzes decomposition of a peroxide, such as hydrogen peroxide, into oxygen. In some embodiments, the one or more oxygen-releasing catalysts is a transition metal catalyst, such as platinum or palladium catalyst.

In some embodiments, the particle can comprise one or more microorganisms. In some embodiments, the shell of the particle comprises one or more microorganisms. In some embodiments, the core comprises one or more microorganisms. In some embodiments, the shell and the core of the particle comprise one or more microorganisms, which can be the same or different. Microorganisms suitable for inclusion into the particles include those microorganisms described above, such as denitrification microorganisms.

In another aspect, the disclosure provided a method for forming a hydrogel particle, the method comprising:
  forming a droplet of a first solution comprising alginate and one or more polymerizable derivatives of polyethylene glycol (PEG) and one or more polymerization initiators, and
  dropping the droplet into a second solution comprising calcium, magnesium, or barium ions.

In some embodiments, the one or more acrylate derivatives of polyethylene glycol (PEG) is PEG acrylate, PEG methacrylate (PEGMA), N-PEG acrylamide, N-PEG methacrylamide, PEG diacrylate (PEGDA), PEG dimethacrylate (PEGDMA), or a combination thereof. In some embodiments, the polymer of the core further comprises monomeric units derived from acrylic acid or methacrylic acid.

In some embodiments, the droplets of the first solution are formed by dropping the first solution from one or more needles. In some embodiments, an electric field is applied between the one or more needles and the second solution. Application of the electric field, such as an electric field having a strength of about 500 to 2500 volts/cm, can advantageously lead to formation smaller droplets and in turn form smaller particles, such as particles with diameters of about 0.1 mm to about 5 mm. In some embodiments, the particle has a diameter from about 0.1 mm to about 5 mm, from about 0.1 mm to about 4 mm, from about 0.1 mm to about 3 mm, from about 0.1 mm to about 2 mm, or from about 0.5 mm to about 2 mm.

In some embodiments, the first solution comprises about 0.5 wt % to about 5 wt % alginic acid or sodium alginate. In some embodiments, the first solution comprises 10 wt % to 60 wt % of PEG diacrylate (PEGDA) and/or PEG dimethacrylate (PEGDMA).

In some embodiments, contacting the droplet with the second solution leads to formation of ionically crosslinked calcium, magnesium, or barium alginate that precipitates out of solution thereby providing a particle or a bead comprising ionically crosslinked alginate. Further polymerization/ chemical crosslinking of the one or more acrylate derivatives of polyethylene glycol (PEG) within the ionically crosslinked particle provides a particle resistant to conditions that lead to leaching of calcium, magnesium, or barium ions (e.g., high pH or presence of complexing agents such as EDTA).

In some embodiments, the second solution is anoxic. In some embodiments, the first solution comprises one or more activators of polymerization/crosslinking. In some embodiments, the activator of polymerization is a photoinitiator. Suitable photoinitiators include 2-hydroxy-4'-(2-hydroxyethoxy)-2-methylpropiophenone (Irgacure 2959), lithium phenyl-2,4,6-trimethyl-benzoylphisphinate (LAP), and the like. In some embodiments, the one or more activators of polymerization is a chemical catalyst, such as ammonium persulfate (APS) and tetramethyl ethylene diamine (TEMED). In some embodiments, one or more chemical catalysts can be combined with one or more photoinitiators to accomplish the formation of the hydrogels.

In some embodiments, the hydrogel particle comprises covalently crosslinked hydrogel. In some embodiments, the hydrogel particle comprises covalently crosslinked hydrogel and/or ionically crosslinked hydrogel.

In some embodiments, the first solution comprises one or more microorganisms, such as the microorganisms described above. In some embodiments, the conditions used to form the hydrogel particle, e.g., polymerization of the one or more acrylate derivatives of PEG, are compatible with maintaining the one or more microorganisms alive throughout the particle formation process.

In some embodiments, in addition to the one or more acrylate derivatives of PEG, the first solution can comprise additional polymerizable compound, such as acrylic acid, methacrylic acid, or a combination thereof.

In some embodiments, the method further comprising contacting the hydrogel particle with a third solution thereby forming a shell surrounding the hydrogel core. In some embodiments, the method comprising contacting the hydrogel particle with a third solution comprising SBQ-PVA, thereby forming a shell surrounding the hydrogel core, wherein the shell comprises SBQ-PVA. In some embodiments, the polymer in the shell can be further crosslinked. In some embodiments, the third solution and/or shell can comprise one or more fillers and/or one or more catalysts as those described above.

In another aspect, provided herein is a particle formed by the methods disclosed herein.

Unless specifically defined herein, all terms used herein have the same meaning as they would to one skilled in the art of the present invention. The use of the term "or" in the claims is used to mean "and/or" unless explicitly indicated to refer to alternatives only or the alternatives are mutually exclusive, although the disclosure supports a definition that refers to only alternatives and "and/or." The words "a" and "an," when used in conjunction with the word "comprising" in the claims or specification, denote one or more, unless specifically noted.

Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element. Additionally, the words "herein," "above," and "below," and words of similar import, when used in this application, shall refer to this application as a whole and not to any particular portions of the application. The word "about" indicates a number within range of minor variation above or below the stated reference number. For example, in some embodiments "about" can refer to a number within a range of 10%, 9%, 8%, 7%, 6%, 5%, 4%, 3%, 2%, or 1% above or below the indicated reference number.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these components etc. may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

All publications cited herein and the subject matter for which they are cited are hereby specifically incorporated by reference in their entireties.

The following examples are provided to illustrate certain particular features and/or embodiments of the disclosure. The examples should not be construed to limit the disclosure to the particular features or embodiments described.

EXAMPLES

The following examples illustrate preparation of exemplary hydrogel compositions and methods for immobilizing active autotrophic bacteria in hydrogel particles to be able to conveniently take advantage of their metabolic abilities for important practical purposes. These purposes include enhancing the efficiency of wastewater treatment to save space and energy while minimizing water pollution and reducing greenhouse gas emissions, and purifying sweat and urine on a small scale to allow recycling of these fluids into potable water in desert survival conditions. The same hydrogel immobilization methods developed here for nitrogen processing by autotrophic bacteria and archaea can be used with further specific optimizations for many other types of microbes and applications. This can be done for various purposes, including medical applications, where the gel materials would need to be FDA approved for human consumption and the microbes would supply specific metabolic functions, for instance in the gut, that would be useful in treating diseases or genetic disorders in humans or animals, as well as in applications that promote health and resistance to disease.

1. Growth of Cultures on Urea and Ammonia

1.1. Batch Culture Experiments with Monocultures

Figure 1B:
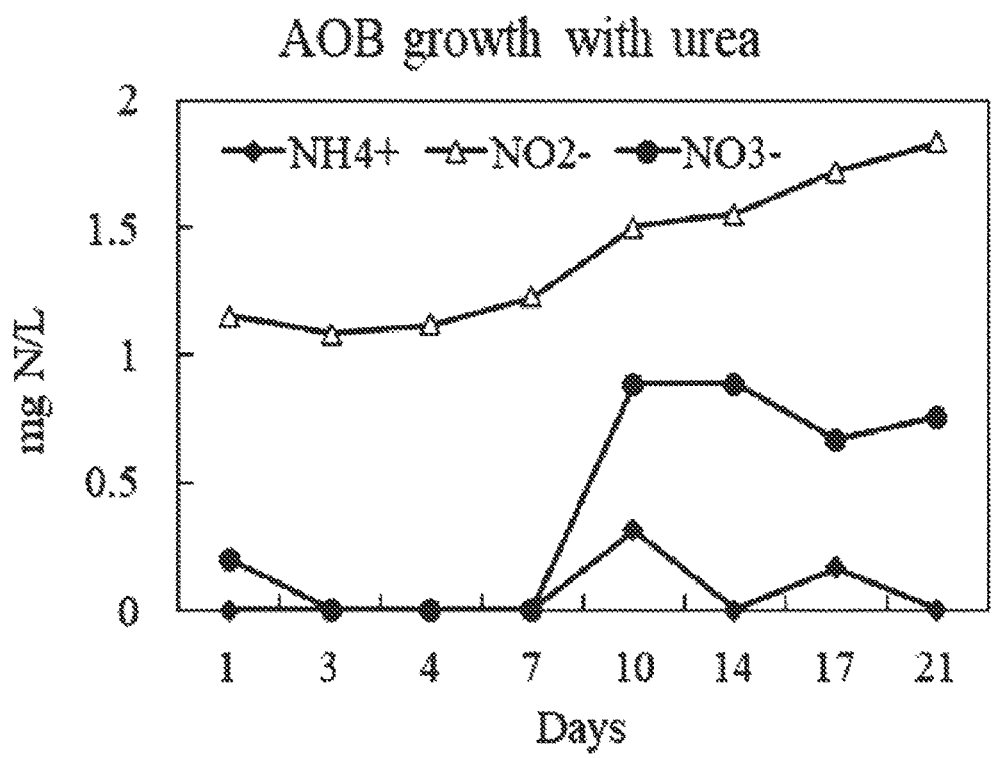
Figure 2:
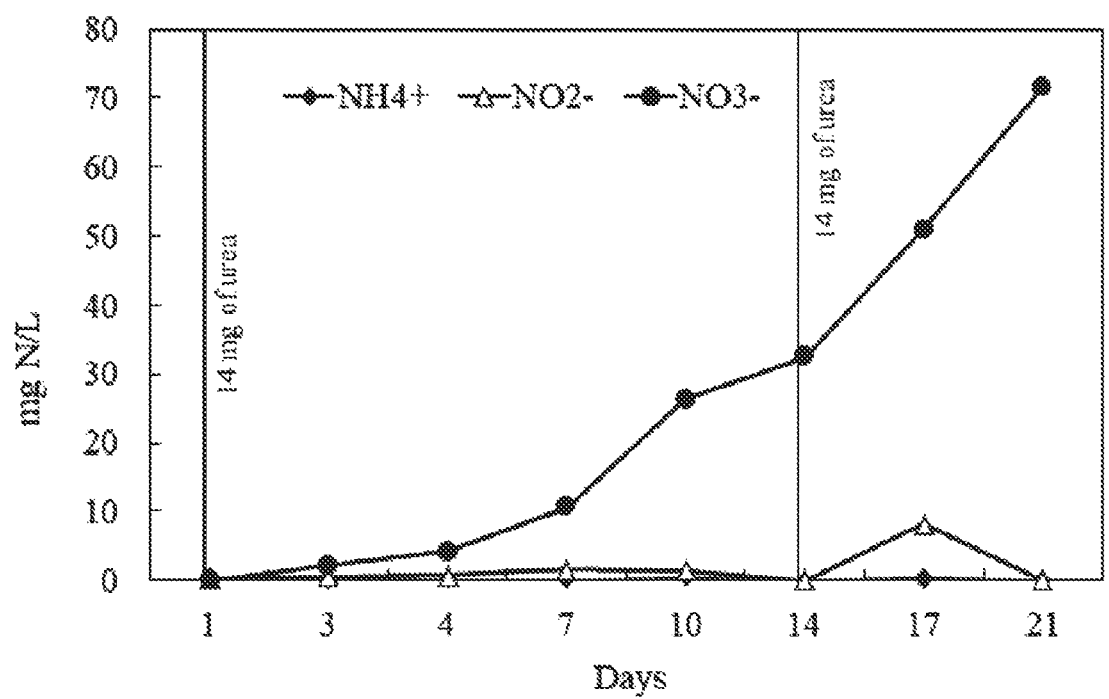
FIG. 2 demonstrates ammonia oxidation followed by urea hydrolysis by Comammox.
Figure 3A:
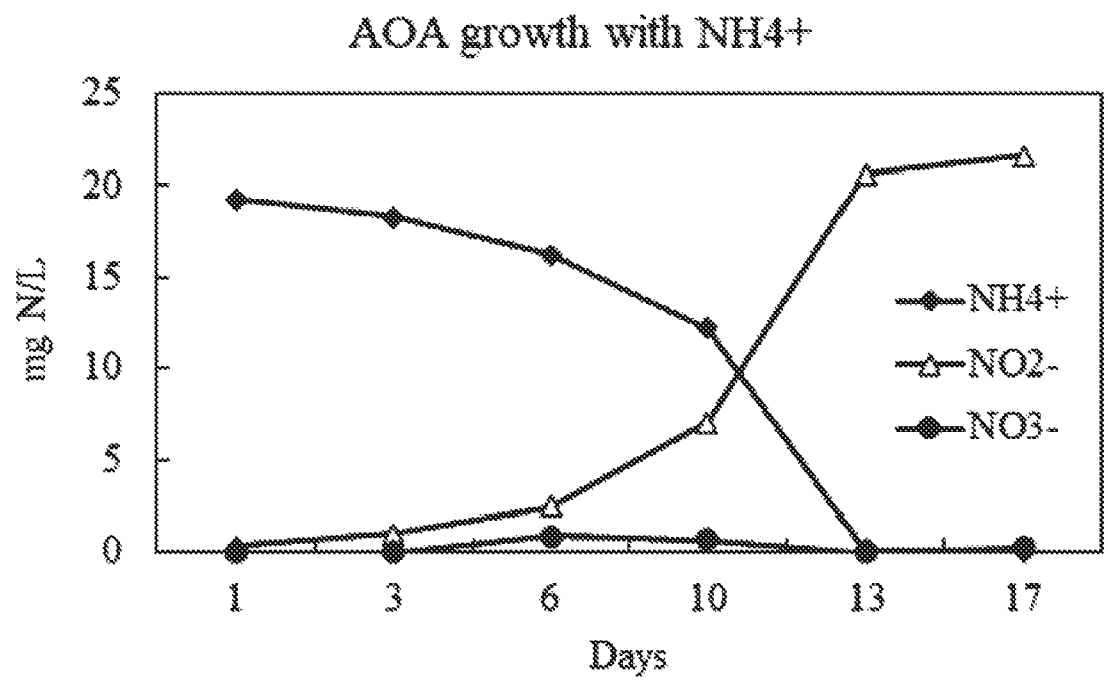
FIGS. 3A-3D show microbial activity of autotrophic organisms demonstrated via ammonia oxidation.
Figure 3B:
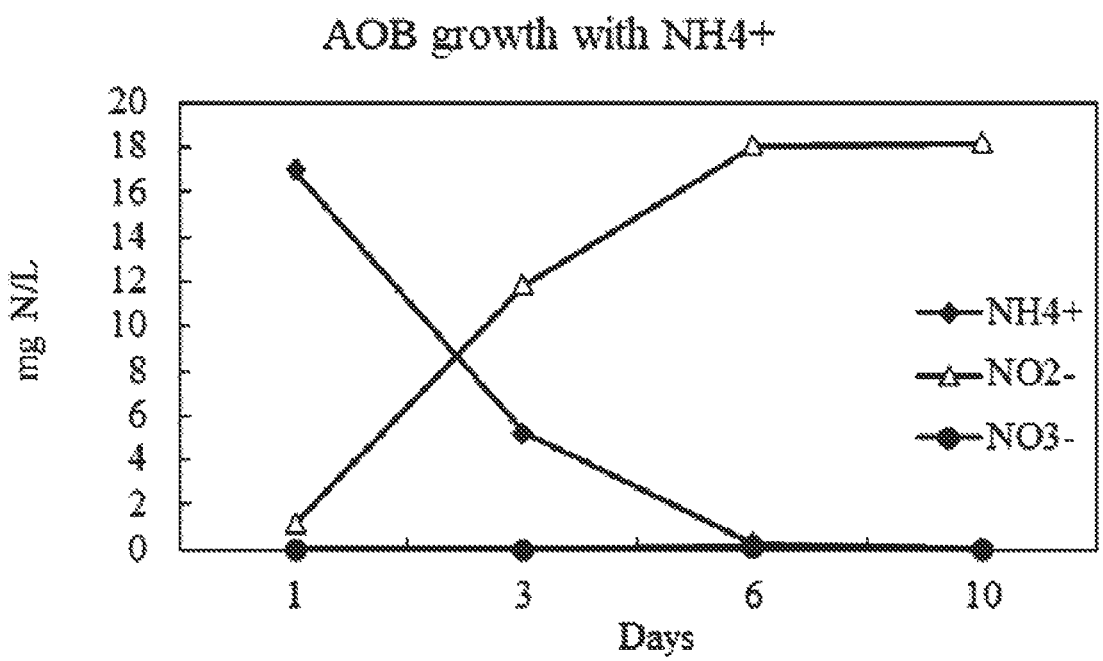
Figure 3C:
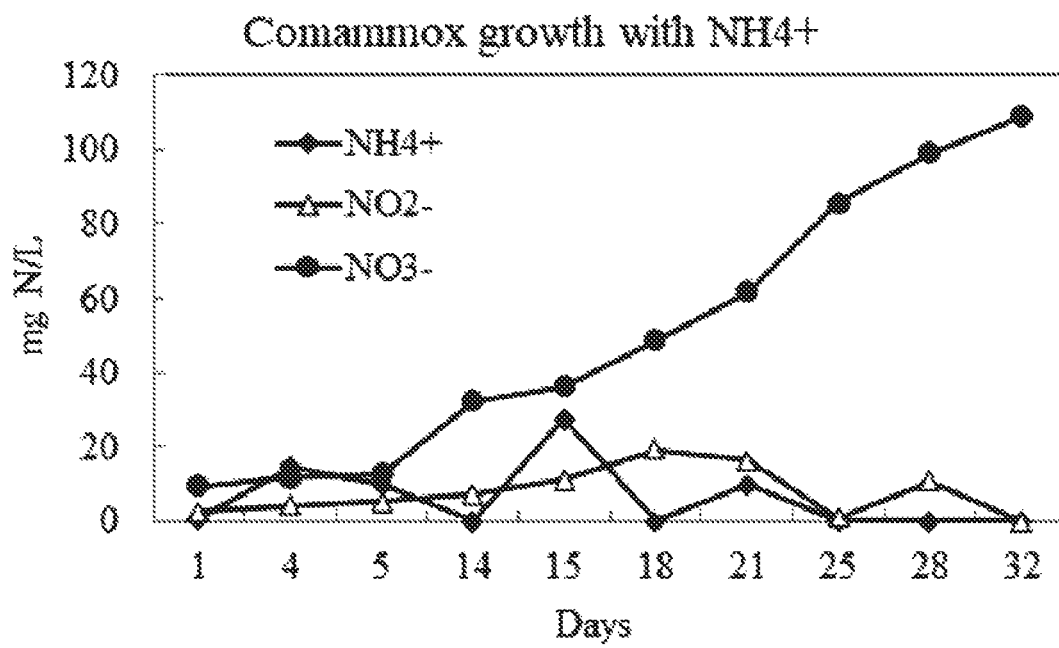
Figure 3D:
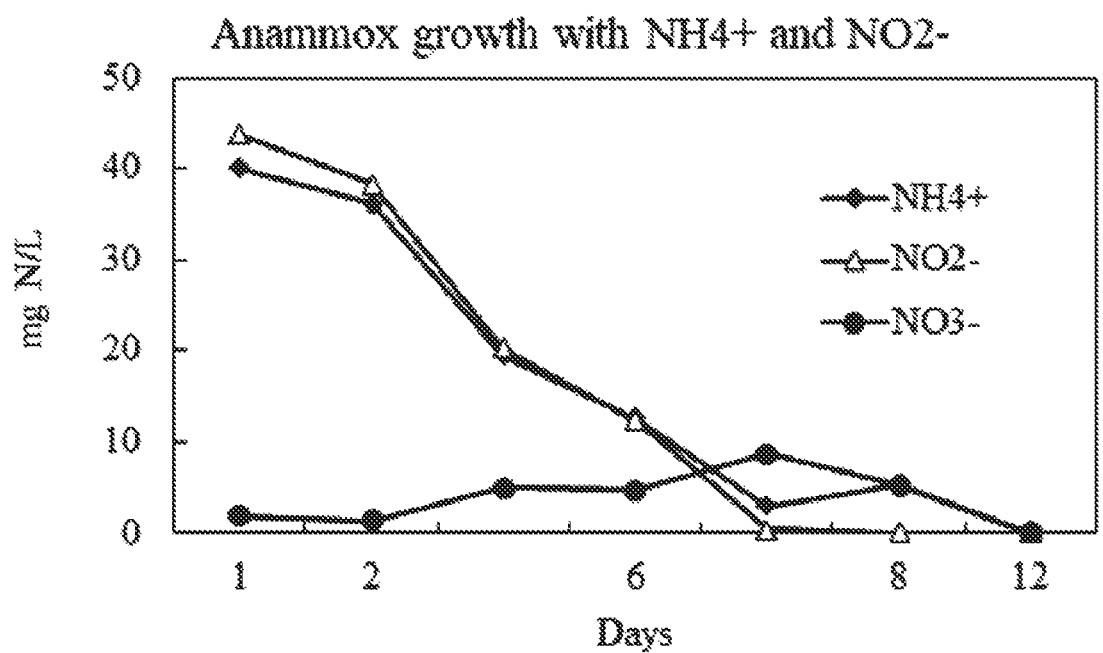

Several microbial strains were investigated for expression of the urease activity needed to hydrolyze urea to ammonia for growth Ammonium oxidizing bacteria (AOB) and Archaea (AOA) as well as Complete Ammonia Oxidizer (Comammox) demonstrated urea hydrolysis. In particular, AOB *Nitrosomonas europaea*, AOA enrichment cultures DW1 and AC2 as well as *Nitrososphaera vienensis*, Comammox *Nitrospira* were capable of degrading urea. AOA and AOB showed slow urea hydrolysis (FIG. 1) whereas Comammox was capable of rapid urea hydrolysis and utilization of produced ammonia (FIG. 2).

Urea was converted to ammonia by the microbial enzyme urease, and the ammonia is then used for microbial growth. Therefore, all tested strains were investigated for ammonia oxidation. All aerobic ammonium oxidizers and anaerobic ammonium oxidizer (Anammox) were capable of growing on ammonia (FIG. 3).

1.2 Growth of Urease Active Monocultures in Hydrogel Beads

Figure 5A:
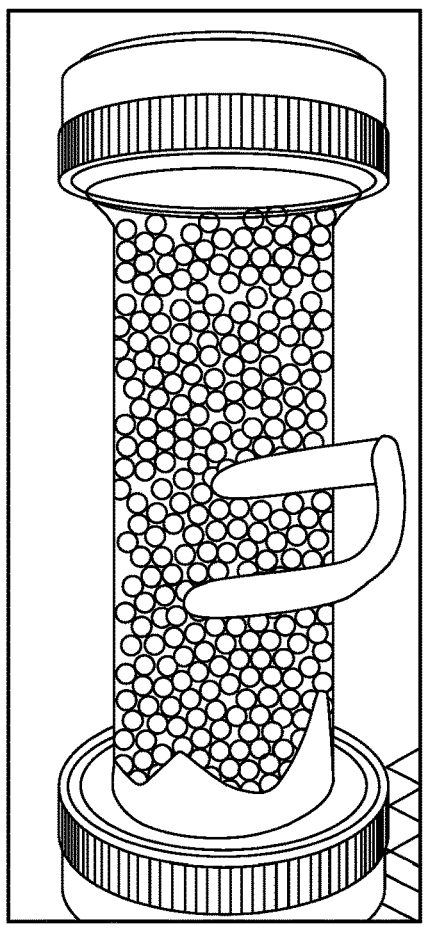
FIGS. 5A-5C demonstrate immobilized Anammox biomass cultivated in an upflow column reactor. Influent ammonium and nitrite was increased gradually to induce the growth and to activate the immobilized Anammox biomass.
Figure 5B:
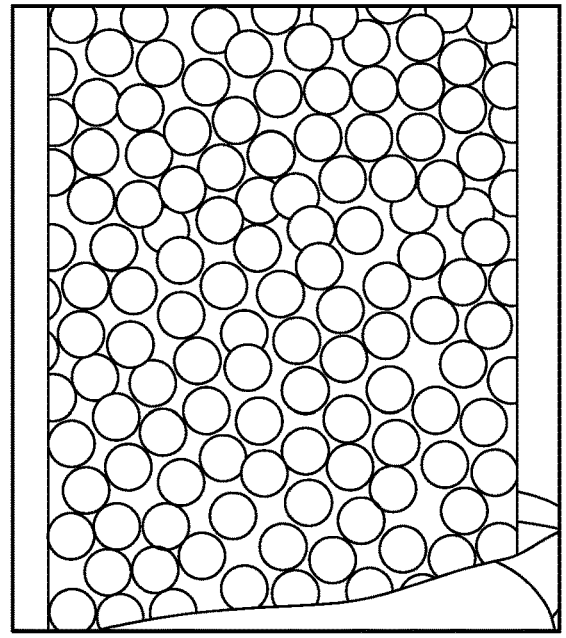
Figure 5C:
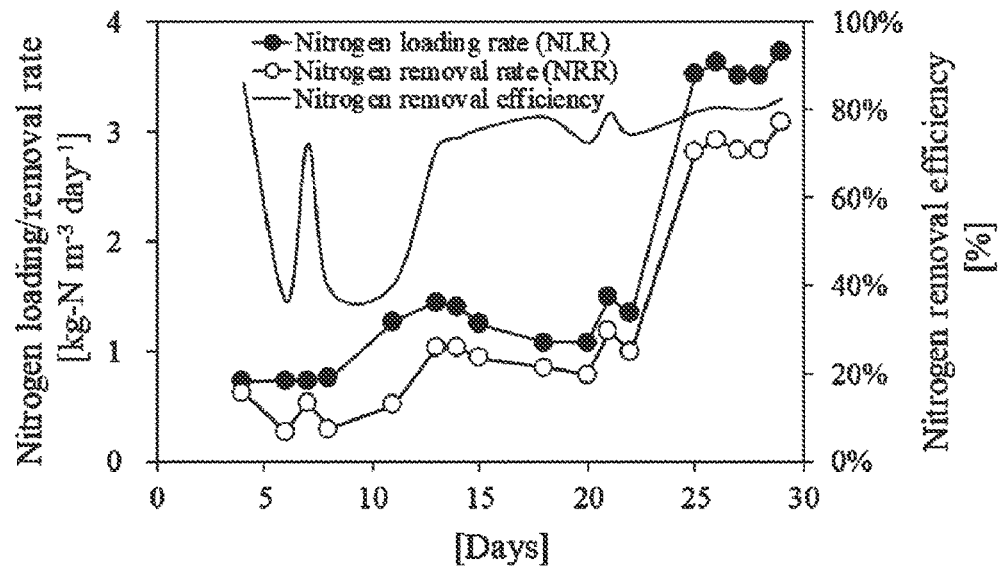

After testing the ammonia- and urea-degrading capacity of the suspended cultures, some strains were encapsulated in hydrogels to investigate their performance in this format. Both aerobic strains (FIG. 4) and anerobic strains (FIG. 5) were capable of catalyzing a high process rate in hydrogel particles. As shown in FIG. 2, hydrogel-immobilized AOA strain AC-2 cultivated in batch mode retained high activity for more than two months. Concentration dynamics of ammonium and nitrite confirmed stable activity of immobilized AC-2 cells. Dispersed Anammox biomass was immobilized in PVA-SA gel beads and operated in continuous upflow column reactor at 30° C. Ammonia removal improved over one month of reactor operation, achieving removal of more than 80% total nitrogen at 3.5 kg-N m$^{-3}$ day$^{-3}$ (FIG. 5).

2. Optimization of Hydrogels

2.1 Overview of Hydrogel Materials and Their Use for Cell Immobilization

There are numerous gel-forming materials that can be used to make hydrogel particles and to immobilize bacteria within hydrogel particles. In the fields of wastewater treatment and environmental remediation, the gels commonly used are made from inexpensive commodity materials which are non-toxic, primarily Alginate (Sodium Alginate or SA) and Polyvinyl Alcohol (PVA), and Acrylate derivatives of Polyethylene Glycol (PEG diacrylate or dimethacrylate, aka PEGDA or PEGDMA). The more costly thiol and norbornene derivatives of PEG have been also used for some small-scale experiments as these provide very efficient and convenient photo-activatable cross-linking chemistry. Of these possibilities, the simplest and most gentle method of immobilizing bacteria is to mix a bacterial cell suspension with a sodium alginate solution and drip this into a calcium chloride bath, where the calcium ions instantaneously form ionic crosslinks between the alginic acid chains and cause the solution droplets to gel into beads. The same ionic cross-linking method works with mixtures of alginate and PVA (PVA/SA), which makes beads that are somewhat more resilient than pure alginate beads. The PVA/SA gel has become one of the most widely used alginate-based hydrogel bead formulations.

The drawback of the simple SA and PVA/SA ionically cross-linked hydrogel beads is that when they are exposed over time to high salt concentrations or to ions like phosphate, citrate, or chelators like EDTA, all of which have a higher affinity for calcium than the alginate does. As a consequence, the calcium is removed from the gel network, and the gel eventually dissolves. Independently cross-linking the PVA in a PVA/SA mixture can overcome this problem. The PVA can be crosslinked by reaction with boric acid at low pH. It has been found that boric acid crosslinked PVA/SA beads can be further strengthened by soaking in concentrated sodium sulfate solution for several hours. This PVA-based formulation has been previously reported to be advantageous in various applications, though none of these reports concerned gas lift or bubbled column reactors specifically. Hydrogel beads produced by dripping PVA/SA mixtures into a bath of calcium chloride and boric acid, and then post-hardened by soaking in sulfate were found to be stable in the turbulent high-shear conditions of a gas lift bioreactor for months to over a year. Many bacteria and other microbes have been successfully immobilized in this type of hydrogel bead, which have the advantage of being made using a simple process that employs low cost non-hazardous chemicals. However, some organisms are damaged by the exposure to the low pH of the boric acid and cannot tolerate this process. Most microbes will require a recovery period of at least a few days to regain full activity. Herein, the inventors have therefore tested alternative ways of forming PVA/SA beads that do not include exposure to low pH. It has been reported that using barium in place of calcium forms a more stable ionic alginate gel, and a photo-crosslinkable PVA derivative, SBQ-PVA, affords a way of crosslinking the PVA without the use of boric acid.

A typical preparation of PVA/SA boric acid sulfate beads is as follows. A solution of the gel-forming polymers is prepared by suspending PVA of MW ~90 kDa and sodium alginate in water to make the solution 15% PVA and 1.5% SA and in addition a 0.1-0.2% carboxymethyl cellulose may also be included. Percentages may vary per application. A viscous solution is formed by autoclaving these components suspended in water. Two parts of the above solution is mixed with one part concentrated bacterial suspension, producing a solution containing 10% PVA and 1% SA with a high concentration of the chosen bacteria. This viscous solution with suspended bacterial cells is then pumped through an array of 24-gauge needles at a rate that allows the formation and release of individual droplets. The droplets fall into a stirred solution of 3-5% boric acid and 2-4% calcium chloride with a pH of 3 to 4.5. The volume of the receiving solution should be at least 10 times the volume of polymer solution being dropped because boric acid is consumed in the process and a sufficient amount should be present to avoid depletion of this reactant. An electric field with a strength in the range of 500 to 2500 volts/cm may be applied between the needles and the receiving solution in order to form smaller droplets and make smaller beads.

The beads are allowed to stir in the boric acid calcium chloride solution for 30 to 90 minutes and are then strained out, rinsed, and placed in about 5 volumes of 0.5 M-1.0 M sodium sulfate for 6-12 hours with gentle stirring. The beads are then strained out of the sodium sulfate solution and placed in about 5 volumes of water for an hour, the water is poured off and replaced with fresh water or bioreactor medium and the beads allowed to soak for another hour to remove any excess sodium sulfate. Next, the beads are strained out, rinsed briefly with water and are then ready for usage.

The next most widely used type of hydrogel for immobilizing bacteria for wastewater treatment purposes are the PEG acrylates, most commonly PEG dimethacrylate (PEGDMA). These hydrophilic pre-polymers can be cross-linked into gels by any convenient free radical initiator, including water soluble photo-activators such as Irgacure (2-Hydroxy-4'-(2-hydroxyethoxy)-2-methylpropiophenone, aka Irgacure 2959) and LAP (lithium phenyl-2,4,6-trimethylbenzoylphisphinate). Being made from a fully synthetic polymer, the PEG gels are stable and resistant to biodegradation, and forming these gels does not expose bacteria to especially harsh conditions. The cross-linking process is not as fast as for the ionic gels, so in order to form beads either a stable aqueous-oil emulsion must be formed in a fluidic device or an SA-assisted droplet-forming process must be used. In either case the cross-linking reaction must be protected from air as the free radical reaction is quenched by oxygen. The fluidic method allows the most control over the size of the droplets, and thus the gel beads. This is not easy to scale up to treatment plant scale, so most large-scale examples of bacterial immobilization in PEG hydrogels have used a sheet casting approach where the sheets are subsequently cut into small cubes.

The approach disclosed herein differs from the previous attempts in that the inventors have developed a method for forming PEGDMA-based beads by including 0.5 to 1% sodium alginate (SA) in the solution of one or more PEG acrylate or methacrylate derivatives (e.g., PEGDMA) and dropping this solution into a calcium salt or barium salt (e.g., chloride) solution that is sparged with nitrogen gas. This method makes the PEGDMA bead formation process as convenient as a known PVA/SA bead formation and allows the use of an electric field to make smaller beads. The cross-linking reaction can be initiated by including a polymerization initiator, such as LAP in the PEGDMA/SA solution and shining a 365 or 405 nm light source on the needles and forming droplets in a nitrogen atmosphere. Other ways of initiation of polymerization can also be employed.

The size of the hydrogel beads used to immobilize bacteria is another important factor to consider. The presence of the gel may present some degree of resistance to diffusion of oxygen and small ions or carbon source molecules that the immobilized microbes require (e.g., contaminants that are being removed by the microbes), so much of the microbial activity in hydrogel beads could ultimately be found near the surface. If both an aerobic and anaerobic microbe are immobilized in a gel bead, the aerobes colonize primarily near the surface, and they intercept most or all of the available oxygen in solution. This can help to maintain an anaerobic environment in the core of the gel particle where the anaerobic organism can grow. The same stratification phenomenon is observed in naturally formed biofilm particles. A large bead, having a diameter greater than about 2 mm, can contain a large anaerobic volume, while a bead that is small (e.g, having a dimeter of 1 mm or less, 0.5 mm or less, or 0.1 mm or less) may not be able to support an anaerobic zone depending on the oxygen concertation in the water. The surface-to-volume ratio (S/V) will to some extent determine the ratio of aerobic to anaerobic organisms that is possible, and the S/V ratio depends on the size of the bead, with smaller beads having higher S/V ratios.

Beads of varying sizes can be formed in a T-channel fluidic or microfluidic device by varying the flow rates of the oil and aqueous phases. This method allows precise control of particle sizes. In the case of PVA/SA beads, the polymer solutions are quite viscous, and there is a practical limit of about 3 mm diameter for beads produced by dripping the polymer solution through a fine needle orifice. The inventors generated a method allowing for production of smaller breads, down to about 0.5 mm, by applying a strong electrostatic field between the needle and the receiving calcium chloride/boric acid solution. Control of bead size is less precise with this electrostatic dropping method and the size range of beads produced is not as tight as that obtained by the fluidic method, but electrostatic dropping can be scaled up. The hydrogel methods outlined above are summarized in Table 1.

TABLE 1

Conditions for preparation of hydrogels

| # | Base Gel Chemistry | Crosslinking | Diameter | Advantages | Disadvantages |
|---|---|---|---|---|---|
| 1 | PVA + Alginate (PVA/SA) | $Ca^{+2}$ | 3-5 mm | Inexpensive, simple, gentle immobilization conditions. Starting point for optimization | Gel breaks down easily when exposed to phosphate containing solutions, organic acids, etc. PVA component not cross-linked |
| 2 | PVA/SA | $Ba^{+2}$ | 3-5 mm | Simple, relatively gentle immobilization conditions. Somewhat more robust gels formed. | Barium may be toxic to some microbes. PVA component not crosslinked |
| 3 | PVA/SBQ-PVA/SA | $Ca^{+2}$ and SBQ-PVA dimerization by light | 3-5 mm | Simple, gentle immobilization conditions. PVA component at least partially crosslinked | Light wavelength needed is 365 nm UV. May not be well tolerated by some sensitive microbes. |
| 4 | PVA/SA Different PVA concentrations tested, from 6% to 10%. | $Ca^{+2}$ and boric acid | 3-5 mm | Simple. PVA component is well cross-linked, gel network is open | Conditions may be harsh for some microbes |
| 5 | PVA/SA by gravity dropping | $Ca^{+2}$ and boric acid | 3-5 mm | More bacteria may survive in the core | Conditions may be harsh for some microbes |
| 6 | PVA/SA by electrostatic dropping | $Ca^{+2}$ and boric acid | 0.5-2 mm | Smaller beads have good S/V ratio | Moderately technical apparatus |

TABLE 1-continued

Conditions for preparation of hydrogels

| # | Base Gel Chemistry | Crosslinking | Diameter | Advantages | Disadvantages |
|---|---|---|---|---|---|
| 7 | Polyethylene glycols (PEGs) | 2 types of radically initiated polymerization | Depends on method | Crosslinking chemistry is benign | More expensive Gel network is fine |
| 8 | PEG w/click chemistry | SH-Norbornene, light catalyzed | Depends on method | Very efficient x-link chemistry | Relatively expensive |
| 9 | PEG w/std acrylate chemistry | Acrylate x-link, light catalyzed | Depends on method | Range of gel stiffness and porosity possible | Moderate costs |
| 10 | PEGs w/micro or macro fluidic bead formation using oil | Choice of Condition 8 or 9 | ~100 um to 2 mm | Good control of size and distribution | More technical apparatus, oil to be removed |
| 11 | PEGs + Alginate with gravity dropping | Choice of Condition 8 or 9 | 3-5 mm | Simple. Gel network may be somewhat more open. No oil | Alginate may be lost over time from beads |
| 12 | PEGs + Alginate with electrostatic dropping | Choice of Condition 8 or 9 | 0.2 to 2 mm | Simple. Gel network may be somewhat more open. No oil. | Alginate may be lost over time, Moderately technical apparatus |

3. Impact of Different Protocols on Microbial Activity

The size and shape of hydrogel carriers can greatly influence the accessibility of microorganisms to nutrients and therefore impact microbial growth within the polymer matrix. A direct observation of small and large beads (using 25G needles and L/S 16 tubing respectively) crosslinked with different agents (calcium, barium, sulfate, light) was carried out to give a first insight into their diffusion behavior (FIG. 5). At 6% PVA, beads crosslinked with barium, calcium, and under blue light (Condition $Ba^{2+}$, $Ca^{2+}$, and SBQ respectively) appeared round, smooth, and clear in color. Beads crosslinked with sulfate (condition $SO_4^{2-}$ 6%) were white and softer in structure.

Figure 6:
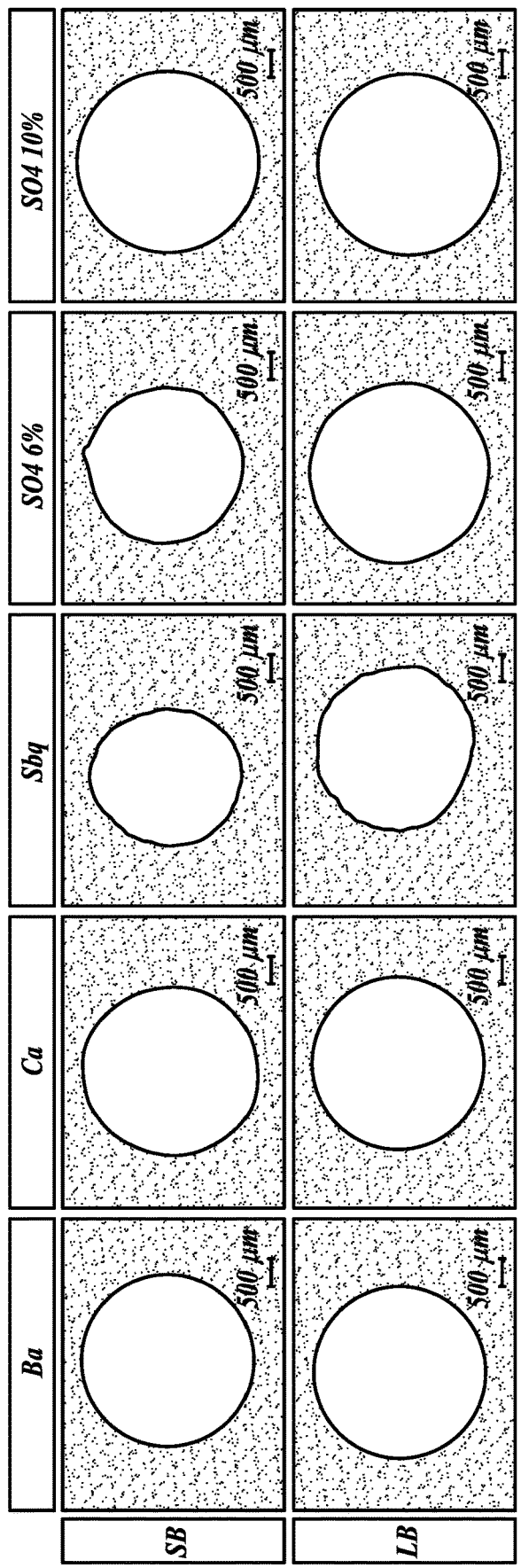
FIG. 6 shows initial morphology of small (SB) and large (LB) hydrogel beads crosslinked with barium (Ba), calcium (Ca), blue light (Sbq) and either sulfate 6% (SO4 6%) or 10% (SO4 10%).

The increase of PVA concentration up to 10% with sulfate resulted in the formation of spherical beads similar to other conditions ($Ba^{2+}$, $Ca^{2+}$, and SBQ), and thus was selected over $SO_4^{2-}$ 6% for the following experiments. After 5 weeks of incubation, no significant changes were observed regarding beads' morphology suggesting that beads structure remained unchanged over time (FIG. 6).

Figure 7A:
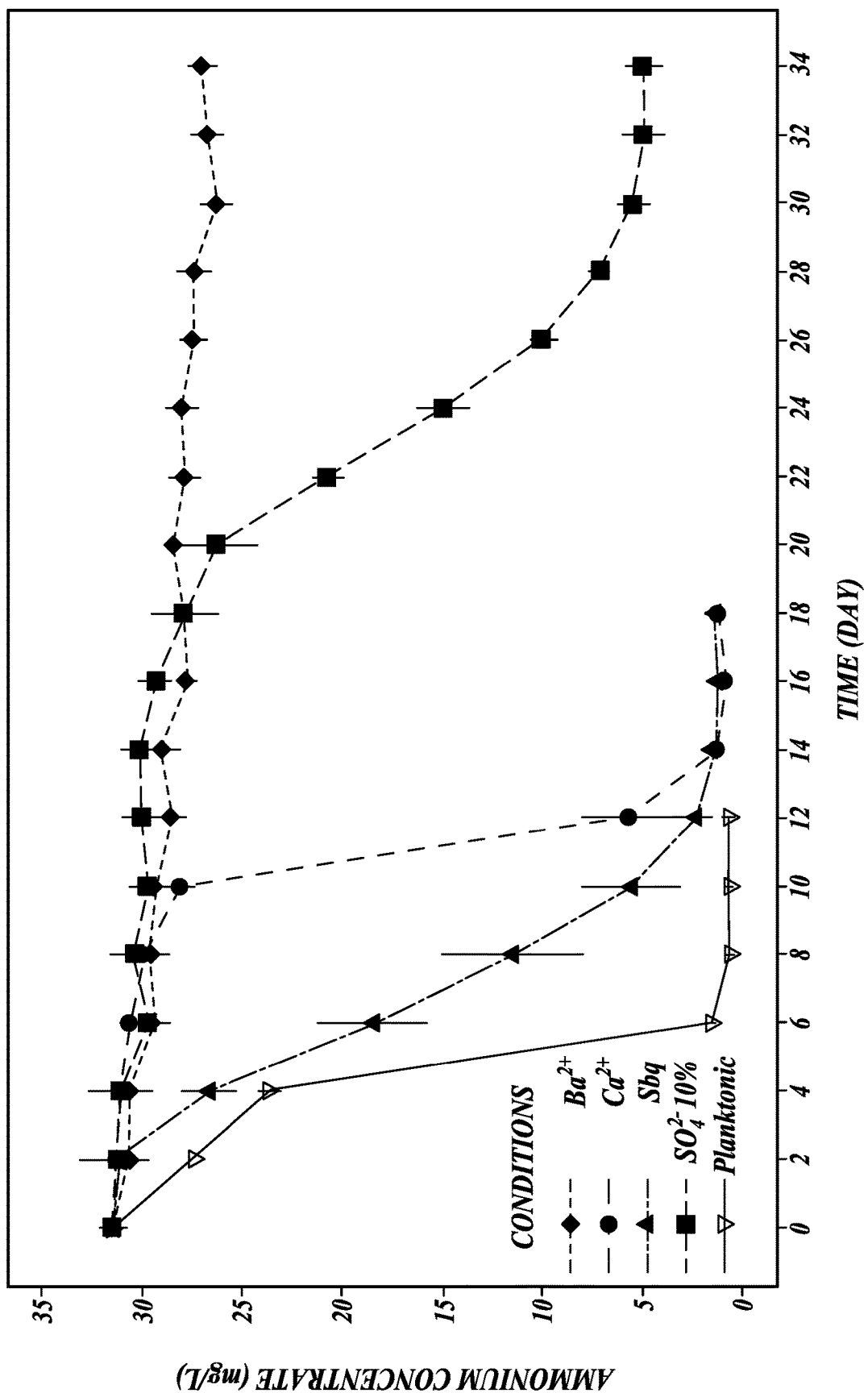
FIGS. 7A and 7B show ammonium removal by immobilized AOA in small (7A) and large beads (7B) Immobilization occurred with 4 different hydrogel types and were compared to planktonic growth.
Figure 7B:
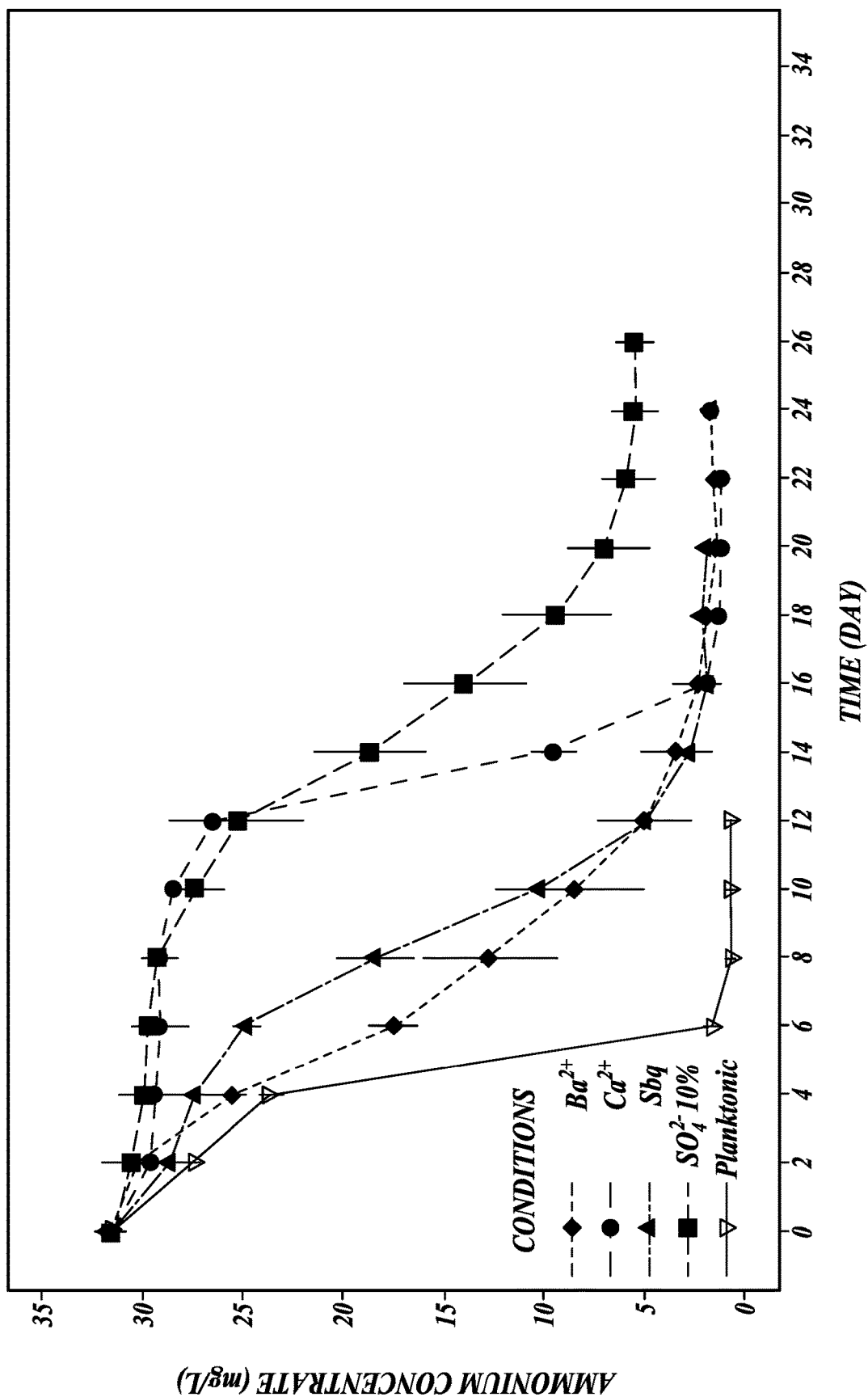

The study of the metabolic activity of entrapped AOA allowed for a better characterization of their behavior in each hydrogel. Results showed that cell immobilization induced a lag phase in growth rates in comparison to planktonic culture (FIG. 7). This delay can be explained by stressful conditions imposed during the crosslinking step. Next, the inventors tested how different sized beads impact substrate diffusion and associated cell viability. The underlying motivation for testing different bead sizes was that in theory larger beads are expected to be more diffusion limited and can hence shield off microorganisms from stressful chemicals in the inner core of the bead, limiting exposure of cells to the chemical stress imposed by the entrapment procedure. This was confirmed by the results. Specifically, ammonium oxidation by entrapped AOA in small and large hydrogel beads crosslinked with calcium, barium, light, or boric acid/sulfate were measured. In small beads, the lag phase was the shortest with PVA-Sbq hydrogels, where ammonium oxidation started after 2 days with an approximate consumption of 3.4 mg $NH_4^+$—N/L/d and a complete consumption on day 14. In contrast, ammonium was only consumed after 10 and 16 days for condition $Ca^{2+}$ and $SO_4^{2-}$ 10% respectively, at an average rate of 6.8 mg and 1.4 mg $NH_4^+$—N/L/d (over the next 4 and 18 days respectively). No significant ammonium removal was observed in barium-crosslinked hydrogel. In large beads, no lag phase was observed for condition $Ba^{2+}$ and Sbq and approximately 1.5 mg $NH_4^+$—N/L/d was removed over 20 days for both conditions. On the other hand, ammonium oxidation was only detected after 10 days for conditions $Ca^{2+}$ and $SO_4^{2-}$ 10% at an average rate of 3.39 mg and 1.49 mg $NH_4^+$—N/L/d over 8 and 16 days respectively. In comparison, ammonium was completely oxidized within the first 6 days (rate=5 mg/L/d) with planktonic AOA. The sharp difference observed between free-cell and entrapped AOA is not surprising as immobilization often induces a lag phase due to the stress and cell morbidity generated by the polymerization process. The effect of barium-crosslinked hydrogels on microbial activity observed with small beads might be explained by the low but significant inhibitory effect of this metal on cell growth combined with a locally high concentration in the hydrogel. This hypothesis was confirmed by the absence of effect observed with large beads, certainly due to the limited contact time of the core during polymerization process. In addition, AOA entrapped in sulfate-crosslinked beads also displayed a longer lag phase than other conditions that can be attributed to the intense stress caused to cells by boric acid soaking step. Smaller beads had a longer lag phase for measurable activity than bigger beads. Sulfate beads had the longest lag phase which may be a result of exposure to boric acid during cell immobilization. However, after this lag phase all cultures had similar ammonium removal efficiency suggesting all bead diameters and chemical procedures are viable for fabrication (FIG. 7).

Figure 8:
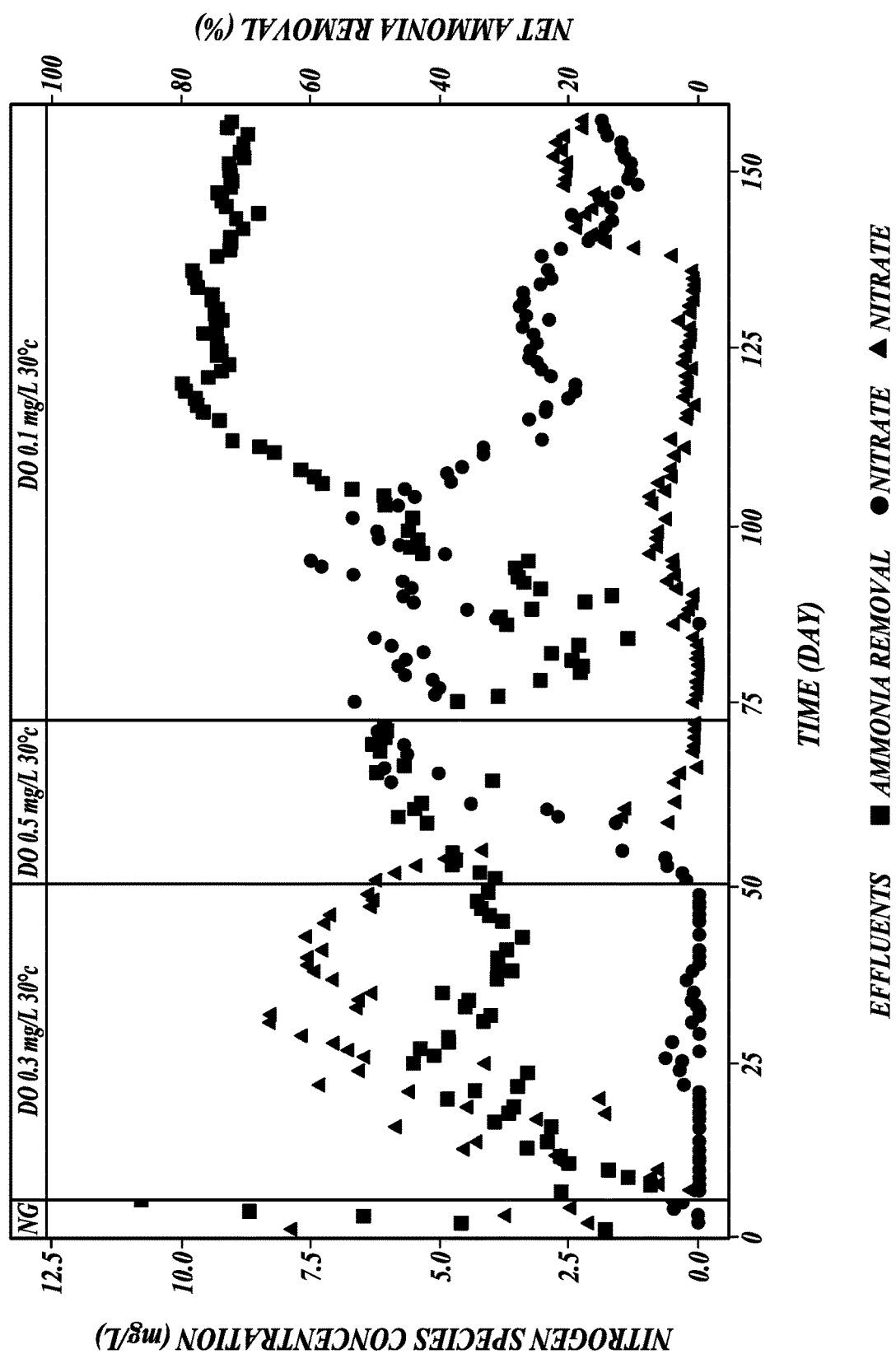
FIG. 8 shows net ammonia removal by entrapped AOB-Anammox in natural granules (NG) (Period 1) and PVA-SA hydrogel beads at 30° C. and 0.3 mg O2/L (Period 2), 0.5 mg O2/L (Period 3), 0.1 mg O2/L (Period 4).

A reactor was operated with hydrogel beads loaded with a mixture of AOB and Anammox at different dissolved oxygen concentrations (FIG. 8). The results highlight the importance of fine-tuning dissolved oxygen (DO) concentration to inhibit nitrate accumulation by nitrite oxidizing bacteria (NOB) within the beads and foster Anammox activity. High DO (0.5 mg $O_2$/L) lead to a reduction in net nitrogen removal whereas low DO (0.1 mg $O_2$/L) resulted in a net nitrogen removal of up to 80%. The experiment also confirmed the resilience of Anammox when the bioreactor is run at suboptimal conditions, recovering activity as reactor conditions again become favorable.

4. Determination of Diffusion Constants of Hydrogels

Figure 9:
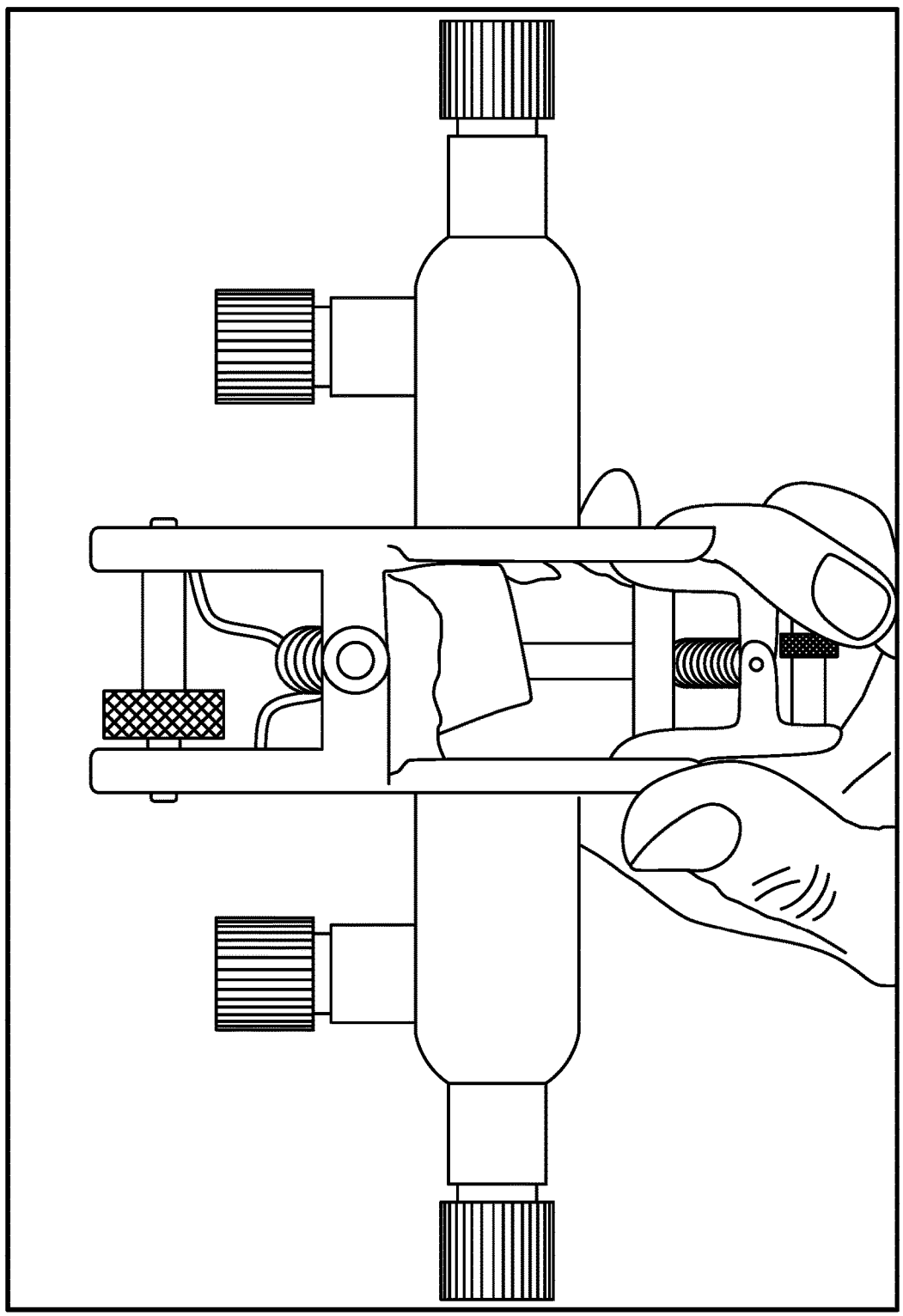
FIG. 9 is a photograph of the diffusion setup.
Figure 10:
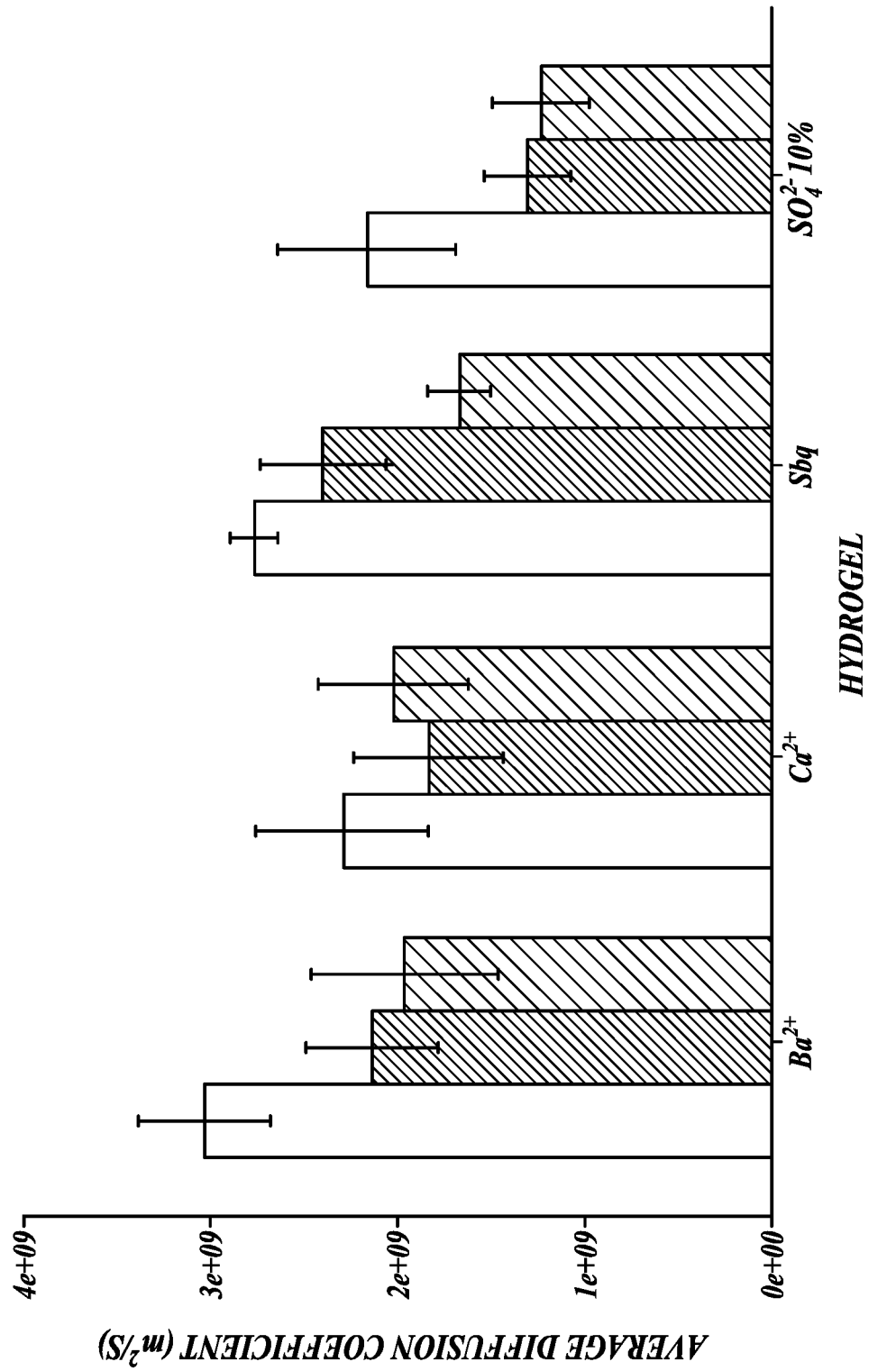
FIG. 10 shows diffusion coefficients of Ammonium (white), Nitrite (dark grey) and Nitrate (grey) in hydrogels crosslinked with Barium (Ba), Calcium (Ca), Light (Sbq) and Sulfate (SO4 10%).
Figure 11:
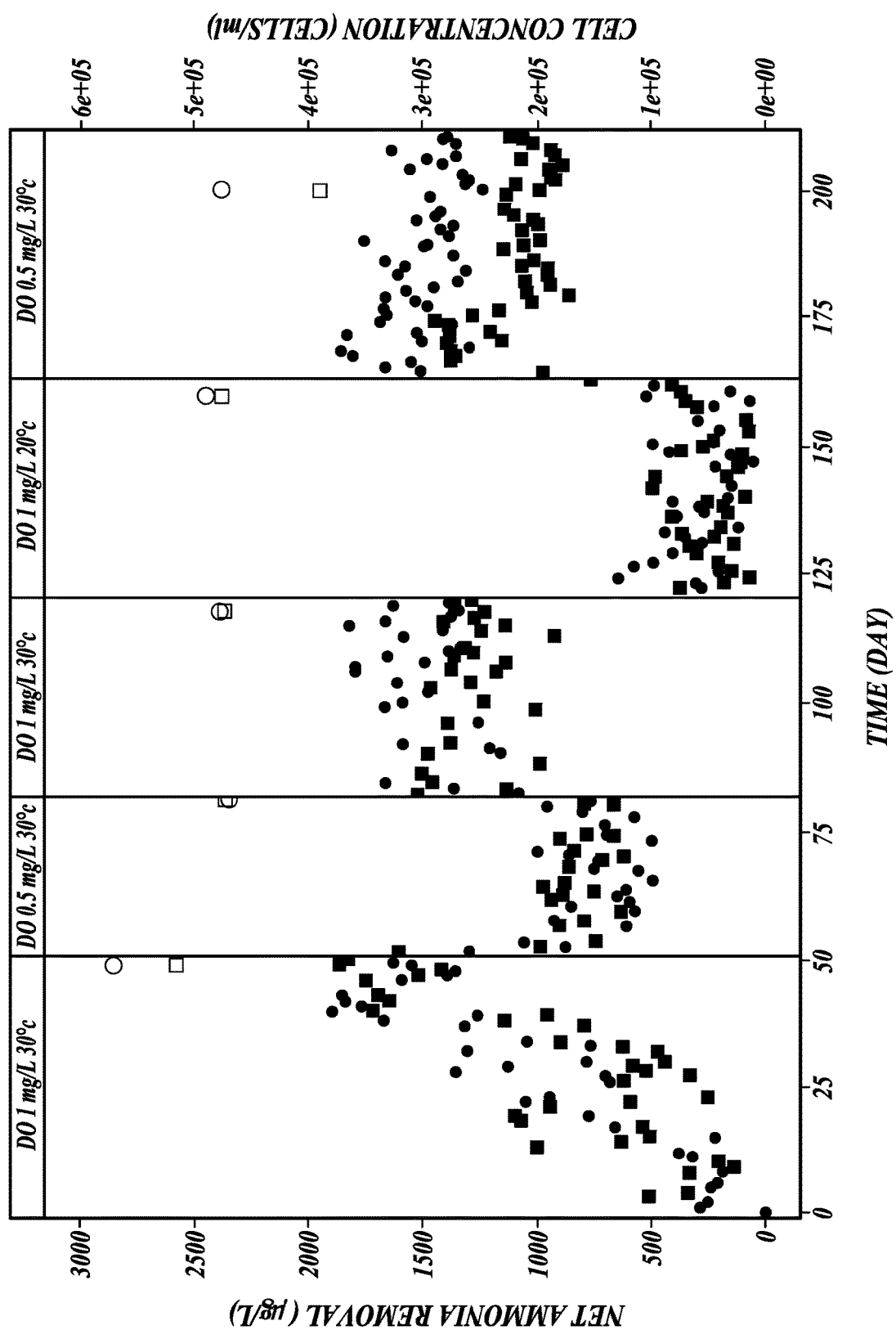
FIG. 11 demonstrates evolution of net ammonia removal (filled) and cell concentration (empty) measured in the effluent of a front plug flow fed (squares) and side baffle-type fed (circles) flow cell.
Figure 12:
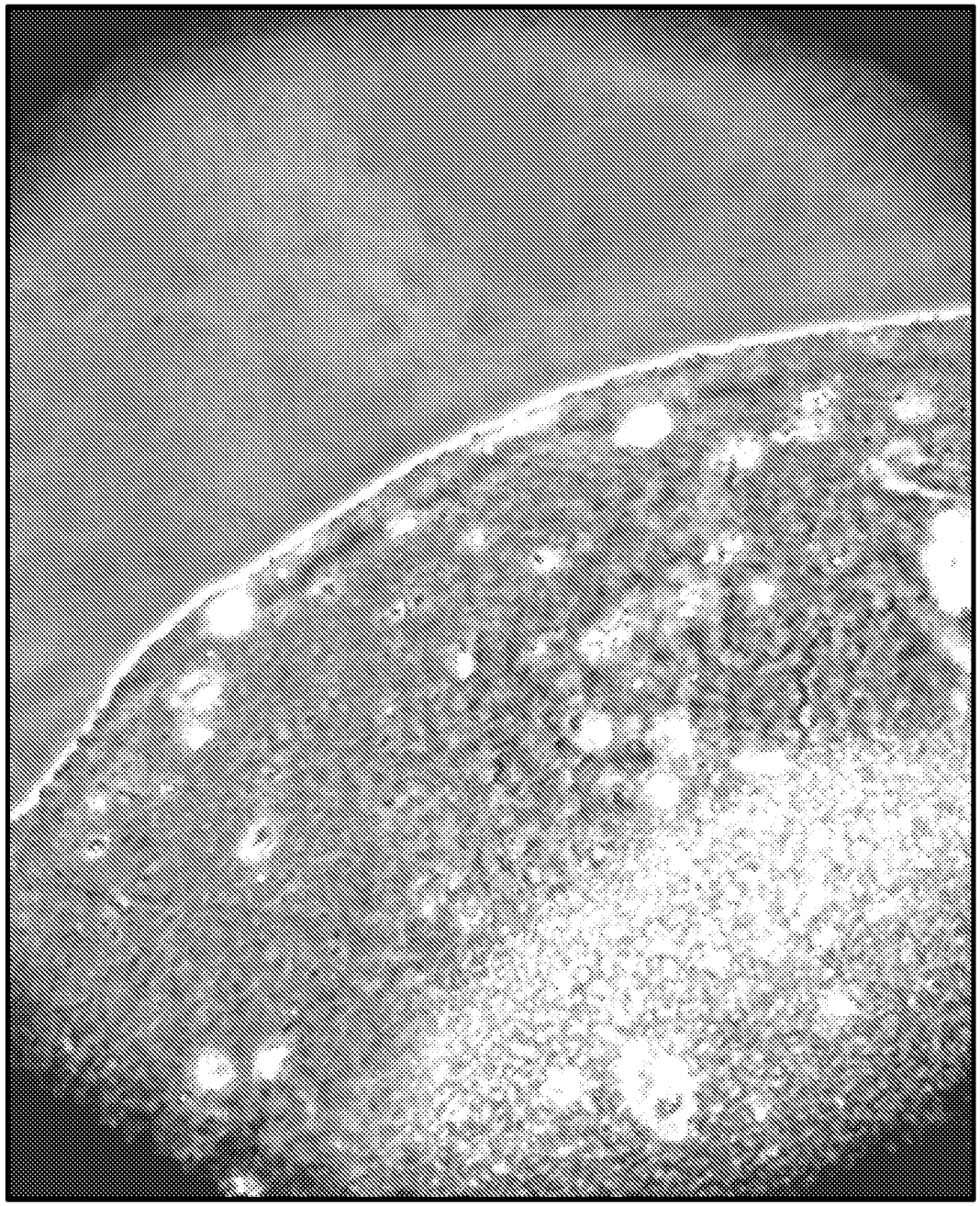
FIG. 12 is a photograph of a thin section of an exemplary PVA/SA boric acid hydrogel bead made with silica and given a thin coating of SBQ-PVA gel.
Figure 13A:
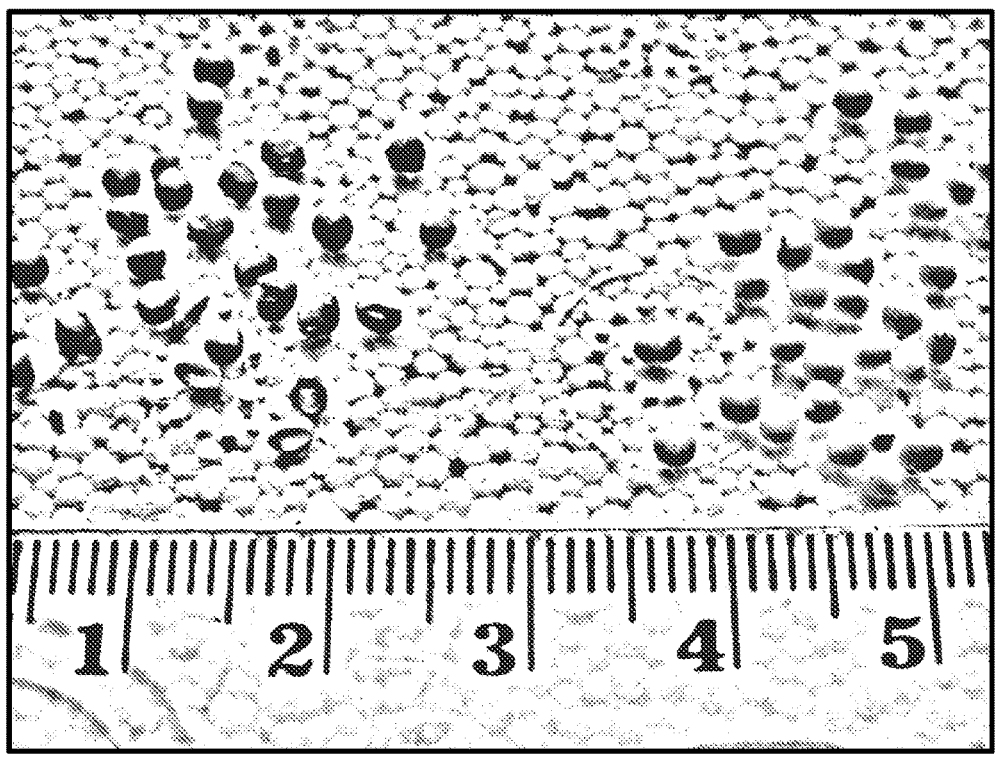
FIGS. 13A and 13B are photographs of beads prepared by testing of an exemplary method of adding an outer shell layer (dark) to PVA/SA beads (white).
Figure 13B:
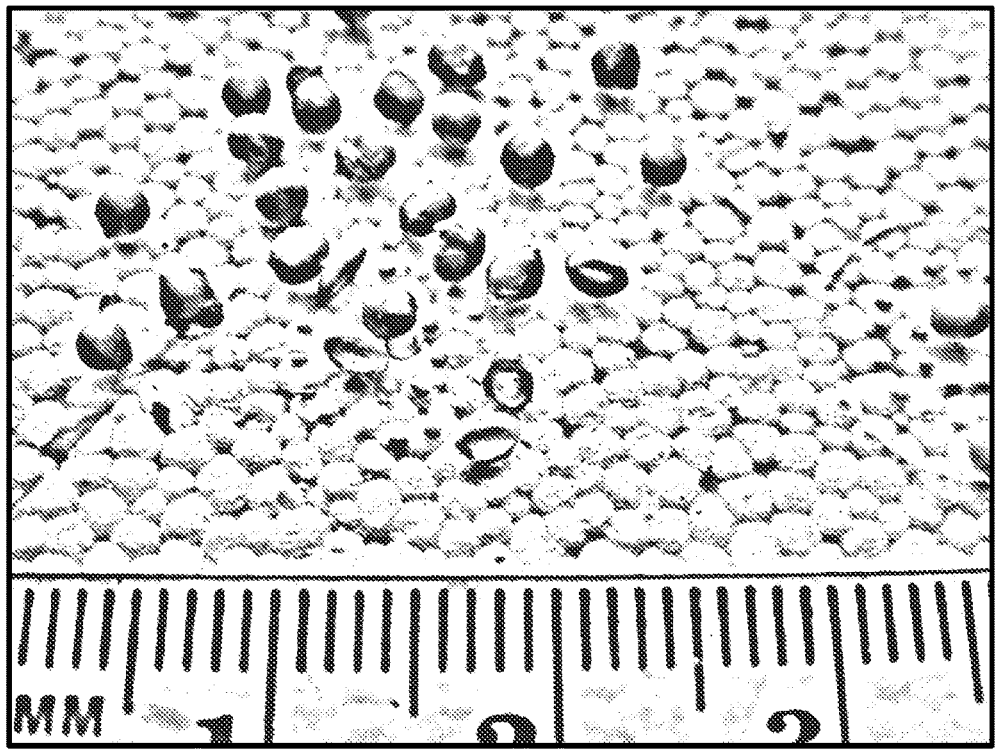
Figure 14C:
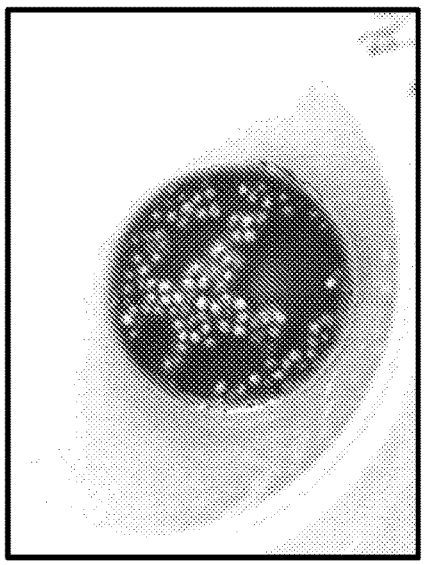
FIGS. 14A-14F are photographs showing progression of an exemplary shell formation. A blue dye was added to the shell-forming layer (SBQ-PVA containing fillers), and formation of the shell was observed.
Figure 14B:
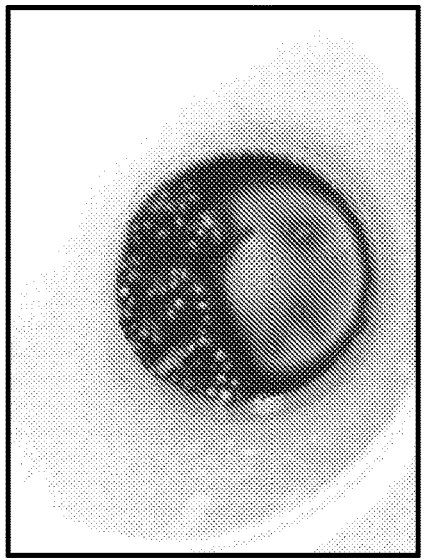
Figure 14A:
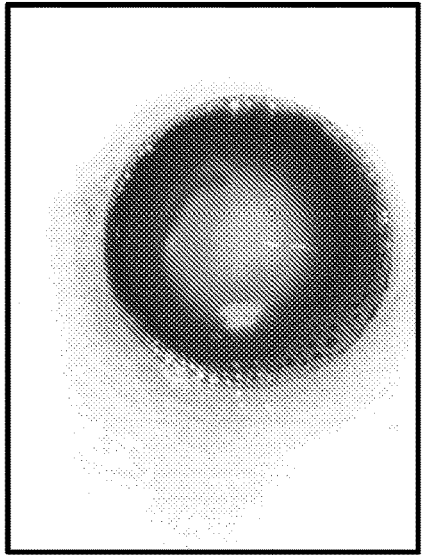
Figure 14F:
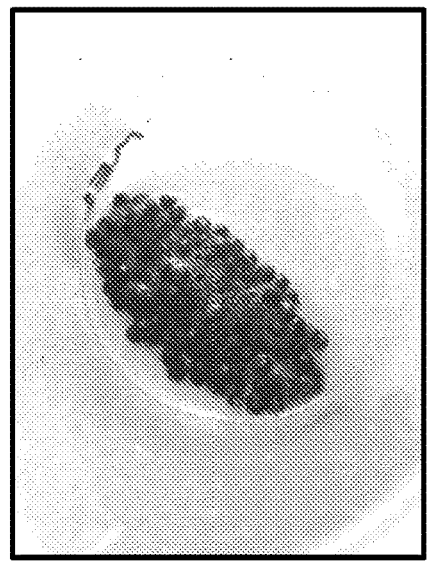
Figure 14E:
Figure 14D:
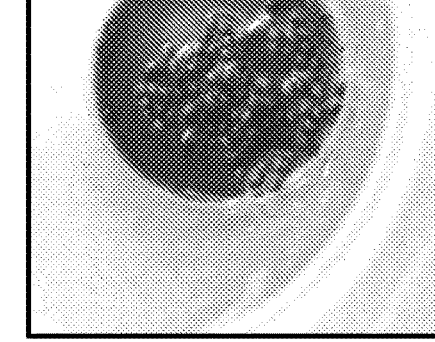

In addition, the diffusion coefficient of key nitrogen species (ammonium, nitrite, and nitrate) was measured for the different hydrogels to determine the impact of cross-linkers on mass transfer (FIGS. 9 and 10). Results showed a better diffusion of nitrogen species in hydrogel beads (between 1 and $3*10^{-9}$ m$^2$/s) compared to natural granules ($0.8*10^{-9}$ m$^2$/s, data not shown) Ammonium had the highest diffusion rate in most cases, probably due to the presence of functional groups negatively charged in PVA that may facilitate the adsorption of ammonium to the hydrogel. In addition, a slight difference was observed between barium- and sulfate-crosslinked hydrogel most likely due to the higher PVA concentration required for the latter (10% vs 6% PVA for other conditions).

5. Flat Bi-Layered Gels

Prior to the formation of a layered hydrogels, 8 mL of a polymer solution composed of 3% polyethylene glycol dithiol (PEG-SH2), 3% 8 arm polyethylene glycol norbornene (PEG-NB8), and 0.6% lithium phenyl-2,4,6-trimethylbenzoylphosphinate (LPT) were seeded with 2 ml of reactivated RGS. The mixture was casted under anaerobic conditions between 2 microscope slides that were spaced 750 μm apart and subjected to UV light (365 nm) for 10 seconds. After removing the cover slide, the slide that was now coated with hydrogel was placed in a customized front-fed flow cell. (not shown).

The operation was repeated to prepare a customized side-fed flow cell. Both flow cells were then fed (1.2 mL/h) with SW medium and incubated at 30° C. and 1 mg O$_2$/L for 50 days (days 0-50, Period 1), then 30° C. and 0.5 mg/L for 30 days (days 51-81, Period 2), again at 30° C. and 1 mg/L for 38 days (days 82-120, Period 3), followed by 20° C. and 1 mg/L for 42 days (days 121-163, Period 4) and finally 30° C. and 1 mg/L for 47 days (days 164-211, Period 5). Every day 1 ml of effluent was sampled to measure ammonium, nitrite and nitrate concentrations using Gallery™ Plus Discrete Analyzer (Thermo Fisher Scientific, USA). In addition, 1 ml of effluent was sampled on days 49, 81, 118, 160 and 200, fixed with paraformaldehyde (1% final concentration) and stored at 4° C. for cell counting. Results (Period 1 to 3; day 1 to 118) showed that decreasing oxygen concentration by half would result in a correlated decrease of net ammonium removal by half as well. In the second part of the experiment, the impact of temperature on aerobic ammonium oxidizers/Anammox metabolic activity was studied by reducing the temperature to 20° C. for 41 days (Period 4). Afterwards, temperature was returned to 30° C. (Period 5) in order to investigate cells' resilience under suboptimal culture conditions. Results from period 4 (day 119 to 160) showed that temperature had a major impact on ammonium removal, mainly affecting Anammox bacteria activity (not shown), resulting in a sharp decrease in ammonium removal capacity down to only ca 0.25 g NH4-N/L removed. However, early results from the last period (starting day 120) at 30° C. highlighted a good resilience of hydrogel immobilized aerobic ammonium oxidizers/Anammox and a rapid recovery of their metabolic activity within 3 days.

A layer of PVA/SA was added to previously made boric acid-sulfate PVA/SA beads (as in row 4 of Table 1) by soaking the previously formed beads in Ca$^{+2}$/boric acid solution, rinsing them briefly, and then placing them into some PVA/SA mixture containing blue pigment. The Ca$^{+2}$ and boric acid that diffuses out of the white core bead then causes the surrounding PVA/SA to gel around the surface. This easy to make shell layer can be broken by rolling the beads between one's fingers and it was not sufficiently robust to persist during extended bubbled column bioreactor operation. However, as detailed below, fabrication of a more robust shell layer has been developed herein and was successfully achieved.

Further work on the basic PVA-SA gel formulation for making beads has proceeded on two fronts. One goal has been to improve the density, strength, and porosity of the beads by incorporating low cost silica into the polymer formulation. The other goal has been to find a practical way to create a robust surface shell layer of hydrogel around the core bead. Beads with a more complex structure where different bacteria or gel compositions can be arranged in ways similar to that present in natural biofilms may be necessary in order to achieve the highest possible processing activity per unit volume. This capability may be key in developing efficient personal scale reactors. The inventors have developed a simple method to attach a shell layer using similar chemistry to the core bead, based on PVA, but with a positively charged PVA mixture in the outer layer. Thus far this has worked best when the core bead is given a stronger negative charge, which can be achieved by incorporating a small amount of negatively charged moieties, sch as carboxymethyl cellulose (CMC). The photo-crosslinkable form of PVA widely used in screen printing resists, SBQ-PVA, carries a positive charge and interacts well with the negatively charged core beads.

A layer containing SBQ-PVA can be bonded to the core bead by the boric acid cross-linking reaction used to make the core beads. However, since AOA are sensitive to the low pH of the boric acid solution, the inventors developed a method based on photo-crosslinked SBQ-PVA for fabrication of beads that maintain high AOA activity. In some instances, the photo-crosslinking reaction alone can provide enough bonding strength between core and the thin SBQ-PVA shell layer such that boric acid exposure can be minimized or avoided entirely. This method of forming a shell layer on a hydrogel bead is simple and inexpensive. It is the fastest method of building a more complex layered PVA/SA boric acid crosslinked bead that the inventors have tried to date.

A significant advantage of the SBQ-PVA shell layer method is that flocculation of the suspended particles, which includes the bacteria that are to be added to the surface layer of the beads, can concentrate the particles or bacteria on the bead surface. This makes more efficient use of the bacterial culture, which may consist of organisms which are difficult and time consuming to grow. With the previously reported simple ionic gelling method described above, the bacteria in the shell layer are applied at the same concentration at which they exist in the bulk solution of PVA and SA that the core beads are soaked in. The majority of the bacteria remain in that solution once the shelled beads are removed. In contrast, in the method using SBQ-PVA disclosed herein, the majority of suspended particles adhered to the bead surface due to flocculation of suspended particulates which occurs as the SBQ-PVA begins to crosslink. This effect is demonstrated below. This type of shell layer application is also perfectly suited to placing other functionalities, such an oxygen-releasing catalyst on the surface of the bead right where the aerobic organisms are found. Herein, the inventors have used 3-micron platinum particles to release the oxygen from hydrogen peroxide in the development of the Liquid Phase Oxygen Supply system described below. Fine platinum particles thus can be placed right where they are needed and with minimal waste using the flocculation method.

An important parameter to consider when applying a shell layer to a bead is the thickness of this layer. In a plain bead, the majority of the immobilized bacteria will grow near the surface because this is where the highest concentration of nutrients, and oxygen in the case of aerobic organisms, are available. As the bacteria metabolize the nutrients and oxygen supplied from the liquid medium that the beads are suspended in, they proliferate most rapidly near the surface where the nutrient concentration is greatest. As their numbers increase in the surface layer, they intercept a greater proportion of the nutrients that diffuse into the bead from the liquid medium and steepen the nutrient gradient further. The result is that the microbes can concentrate near the surface of the hydrogel particle. This effect is often referred to as stratification. It typically is observable by microscopy in the outer 20-100 microns of the bead surface. A surface shell layer applied to the core bead would ideally not be much thicker than this or it may result in significantly reduced diffusion of nutrients to the bacteria in the core bead.

6. Demonstration of the Flocculation Effect from the SBQ-PVA Shell Layer Process SBQ-PVA polymer mix: 1 part SBQ-PVA was supplied (13% PVA with 4 mole % SBQ substitution ratio, from Polysciences Inc., Warrington, PA), in addition to one part 7% 95 kDa MW PVA (Sigma-Aldrich), and 3% 3500 Da MW PVA (Sigma-Aldrich). This SBQ-PVA polymer mix solution is 11.5% PVA of varying MWs, ~half having a 4% mole ratio of SBQ groups (N-methyl-4-(4'formyl styryl) pyridinium).

Fillers: Suspension of 100 mg/ml each of 20 um Sigmacell microcrystalline cellulose (MCC) and 20 um food-grade diatomaceous earth (DE) in water. The presence of some fine filler enhances the flocculation effect and makes a stronger layer. A fine pigment powder such as Prussian Blue can be included to make the layer more visible.

Preparation of the beads: The previously made 10% PVA, 1% SA, 0.1% carboxymethylcellulose (CMC) boric acid/sulfate beads are soaked in 3% boric acid, 2% calcium chloride, pH 4, for ~15 minutes. This will cause the bead diameter to shrink. The beads are collected in a strainer, rinsed briefly with water, and drained well by pressing a paper towel against the underside of the strainer screen. The damp beads may be kept in a beaker for up to an hour until used.

Application of the coating layer: 1 volume of pre-soaked damp beads are placed into 1 volume of SBQ-PVA mix in a container sized so that the viscous liquid suspension can be stirred effectively. The mixture is stirred to coat the beads evenly and then allowed to rest for a few minutes. The added SBQ-PVA and fillers will begin to visibly accumulate on the beads' surfaces after 2 or 3 minutes and flocculation will occur which will cause most of the suspended filler particles and pigment, and bacteria if present, to adhere the bead surfaces. The mixture should be swirled gently to keep the beads from sticking together in a clump. The time course of the interaction of the SBQ polymer mix with the beads and the flocculation of the suspended particulates onto the beads is depicted in the figure below When the suspended particles have mostly adhered to the bead surfaces and the beads are beginning to clump ~2 volumes of water were added and swirled with the beads to separate them. Some of the particles would resuspend in this water. Then 3% boric acid at a pH of 4 was added in small aliquots of ~¼ of the original volume, swirled again and allowed to stand for ~5 minutes. This was repeated several times, with 5 minutes of reaction time between each boric acid addition until the surface layer is sufficiently gelled to allow the liquid containing excess polymers and filler to be drained off and replaced with fresh water twice. Then ~10 volumes of 3% boric acid was poured onto the beads with gentle swirling to fully gel the shell layer and bond it well to the underlying core bead. After 15 minutes the beads were collected in a strainer, rinsed briefly with water, and transferred into about 10 volumes 0.5 M sodium sulfate to fully harden the shell layer.

There are several parameters that can be adjusted to optimize the protocol. The concentration of boric acid and calcium chloride in which the starting beads are pre-soaked can be increased or decreased. The concentration of CMC in the core bead formulation can also be increased or decreased. The relative proportions of SBQ-PVA and plain PVA in the SBQ-PVA polymer mix can be changed. The materials that are used as fillers in the SBQ-PVA polymer mix can be changed or a filler can be omitted. The length of time that the beads are soaked in the polymer mix can be changed. A photoinitiator can be added so that violet or UV-A light exposure can be used to better gel the shell layer before excess polymer is rinsed off and the final boric acid and sulfate treatments are performed. A small amount of a crosslinker with extended length, such at the 1000 Da MW PEGDMA, can be added so that more of the SBQ groups will be in reach of each other in the forming gel and can cross-link both directly with each other and through this extended linker.

Figure 15:
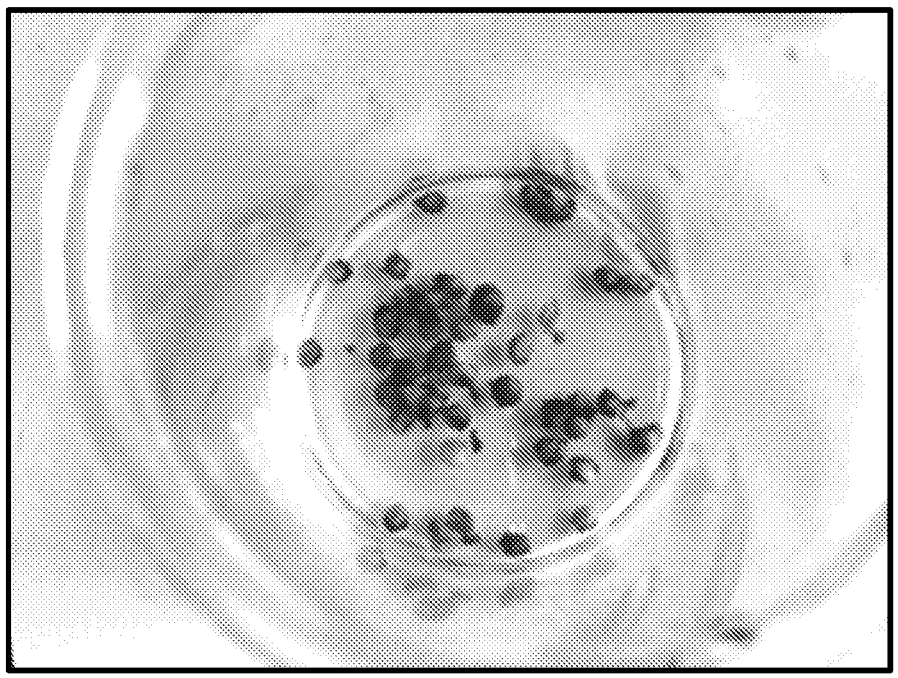
FIG. 15 is a photograph of the final PVA/SA boric acid beads heavily coated in the above flocculation process shown in FIGS. 14A-F.
Figure 16:
FIG. 16 is a photograph of PVA/SA boric acid beads coated using photoinitiated crosslinking with LAP and PEGDMA as extra crosslinker, followed by boric acid and sulfate treatments. This process resulted in a more even thin coating.
Figure 18:
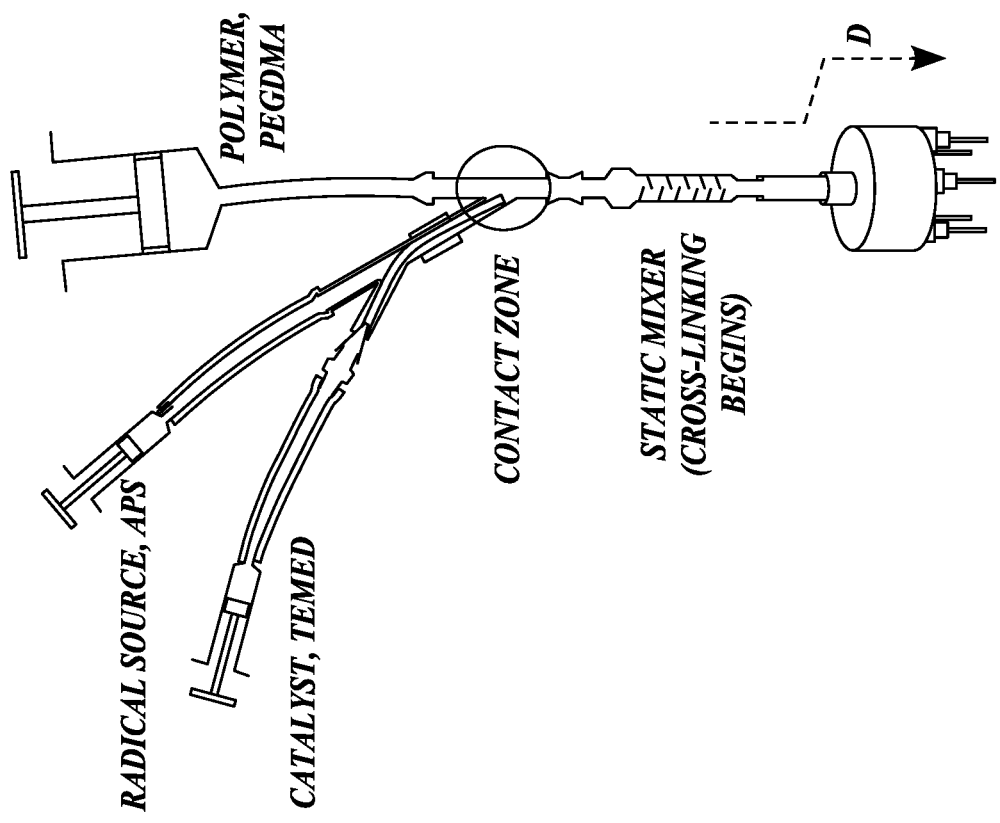
FIG. 18 is a drawing of an apparatus used for producing PEGDMA/alginate beads by chemical initiation. This setup can be used where the biomass to be immobilized is opaque or very light-sensitive. The length "D" can be varied to allow more or less time for polymerization before droplets fall into the CaCl2 bath. If APS is mixed with bacterial suspension, then this can be done with just 2 syringes as only TEMED solution needs to be added before dropping.
Figure 17:
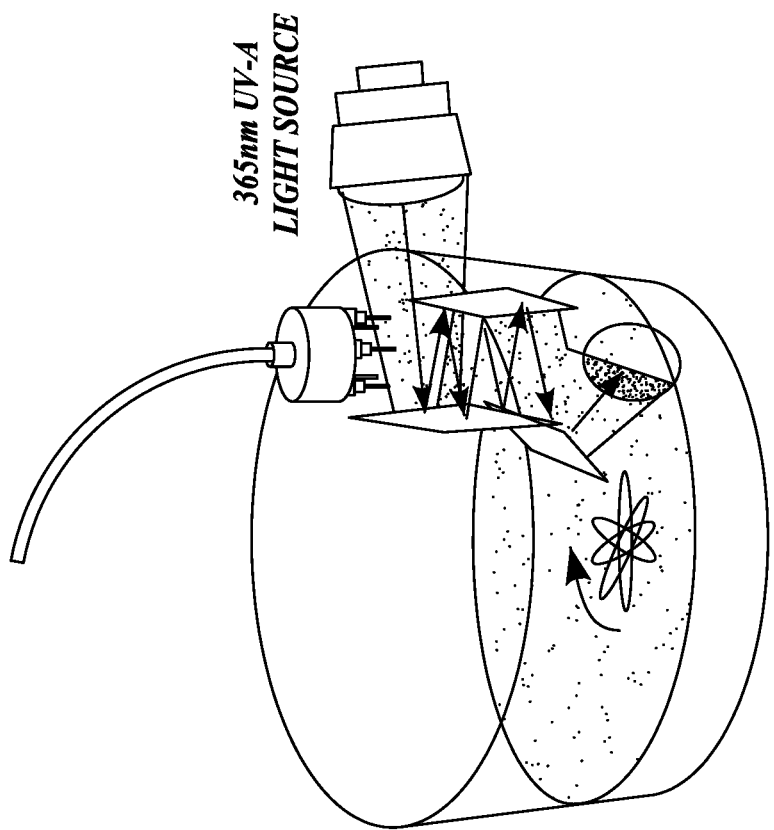
FIG. 17 demonstrates production of PEGDMA/SA beads using photoinitiation. Photoinitiation with the intense violet light from three 3 W LEDs, with focusing lenses, caused very rapid polymerization and a smaller portion of the monomers was lost by diffusion into the $CaCl_2$ bath.
Figures 19A, 19B, 19C:
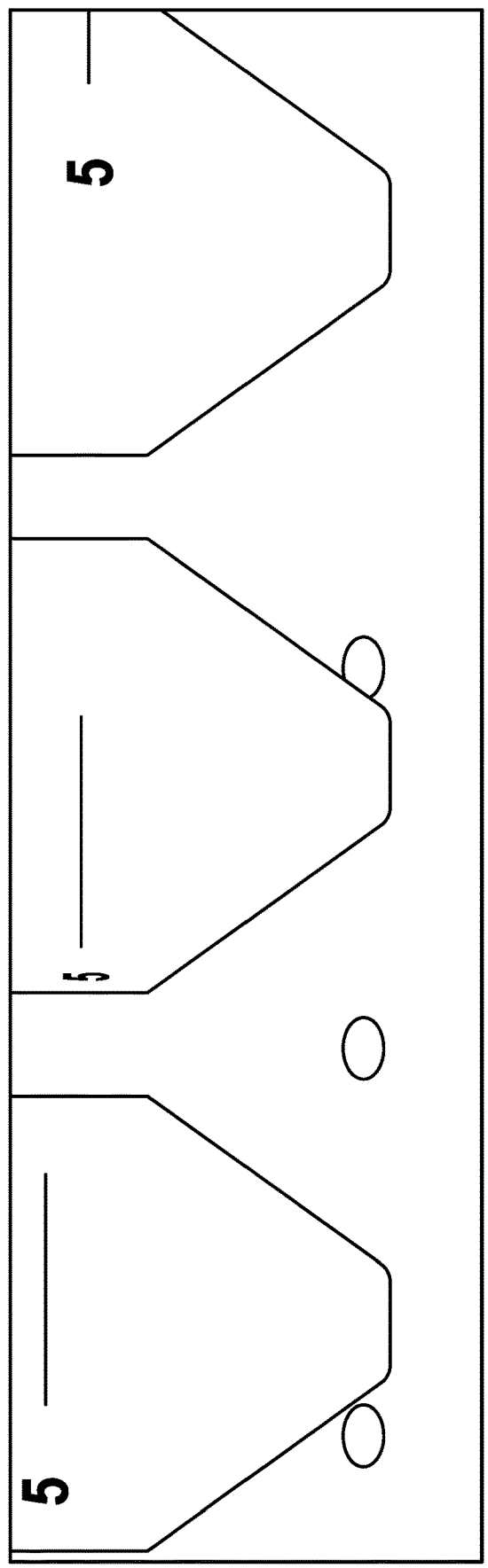
FIGS. 19A-19C show comparison of the density of hydrogels made with and without acrylamide. All beads were made by photoinitiation with violet (405 nm) light. The beads in the tube shown in FIG. 19A contain 12.5% PEGDMA and 0.5% SA and were made by chemical initiation. These beads were most transparent in water, which indicated a relatively lower degree of cross-linking compared to samples shown in FIGS. 19B and 19C. The beads in tube shown in FIG. 19B contain 8% PEGDMA, 2% methacrylamide, and 0.5% SA. The exemplary beads in tube shown in FIG. 19C contain 10% PEGDMA, 2% methacrylamide, and 0.5% SA.

FIGS. 15 and 16 pictures of some finished beads from 2 different SBQ-PVA coating protocols. FIG. 15 shows the dark blue beads from the batch that was thickly coated for the flocculation demonstration above. This layer is much thicker than what we would normally intend to use for bacteria. Such thick layers tend to be uneven. FIG. 16 shows beads from a batch made with photoactivator (LAP) and PEGDMA as accessory cross linker and which were exposed to UV-A light before the first rinsing step. This method produces more even thin layers. This method can be ideal for attaching fine platinum to the bead surface, adding a layer over the core bead that would minimize escape of cells from the bead, or for adding a layer containing an aerobic organism to the surface.

6. PEG-Based Hydrogel Beads

The PVA-based hydrogel particles described above are especially appropriate for municipal scale wastewater treatment because of their low cost. However, for personal scale treatment system, more expensive, photo-crosslinked PEG-based hydrogels can also be considered. The hydrogel fabrication methods can be more involved than for the PVA based gels; however, the low toxicity of the PEG hydrogel crosslinking chemistry is an advantage that has to be weighed against simplicity of the PVA gel fabrication. Some of the methods described herein are listed in rows 11 and 12 of Table 1. The inventors demonstrate herein that a photo crosslinking method that is analogous to the one described above for PVA beads is feasible for PEG beads and offers the same benefits of speed and simplicity.

Disclosed herein is a hybrid approach for making PEGDMA beads that makes use of the ionic alginate dropping method to initially form the bead structure while simultaneously starting the free radical initiation process to cross-link the PEG acrylate precursor component before it diffuses out of the alginate gel. This method uses SA/PEG acrylate polymer mix which is being added dropwise into a $CaCl_2$ bath. A 405 nm violet light or 365 nm UV-A light and a photoinitiator added into the solution being dropped can be used to accomplish polymerization/hydrogel formation. Chemical initiation by mixing APS and TEMED into the flowing stream of polymer mix shortly before passing the gelling solution to the dropping needles has also been used.

6.1 Preparation of PEG/SA Beads by Dropping

An example for a preparation of PEG/SA beads is that a 2% SA solution is prepared by dissolving SA in water with application of heat and then autoclaved. 50% PEGDMA is prepared by dissolving PEGDMA in water with gentle stirring for several hours. This solution is sterilized by filtration through a 0.2-micron filter. One part 2% SA, one part 50% PEGDMA, and two parts water or bacterial suspension are mixed to make a solution that is 12.5% PEGDMA and 0.5% SA. LAP is added to a final concentration of 0.05 to 0.1 mg/ml.

A solution of 2% calcium chloride was placed in a transparent lidded container with a stir bar, the container was placed on a magnetic stirring plate, and nitrogen gas was bubbled through the solution from a tube that passes through the lid with a tight fit and allowed to displace air from the space above the solution. Then the needles used to form droplets were inserted through small holes in the lid and the violet (405 nm) or UV-A (365 nm) light source was placed near the needles to illuminate the forming drops. The PEG/SA solution containing photoinitiator (e.g. LAP) and the chosen bacteria were sparged with nitrogen for ~15 minutes and then pumped through the needles past the light and into the anoxic calcium chloride solution. The beads were left soaking in the anoxic calcium chloride solution for 30-60 minutes, then strained out and rinsed briefly with water or bioreactor medium and then placed in the reactor or other culture vessel.

Figure 20B:
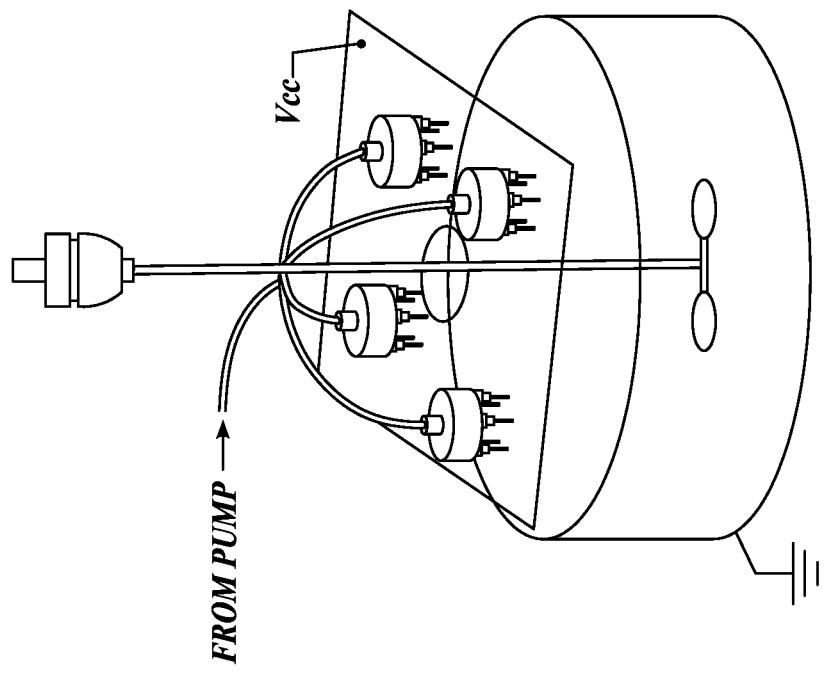
FIGS. 20A and 20B depict small scale electrostatic droplet generator (20A) and schematic drawing of a 24× scale-up of the electrostatic droplet device (20B).
Figure 20A:
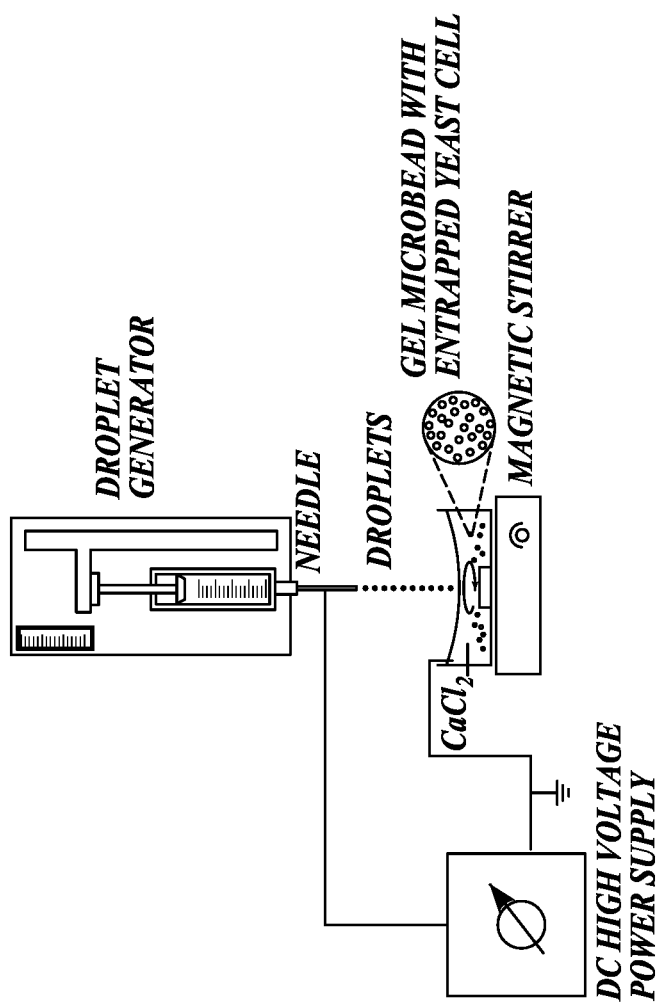
Figure 21B:
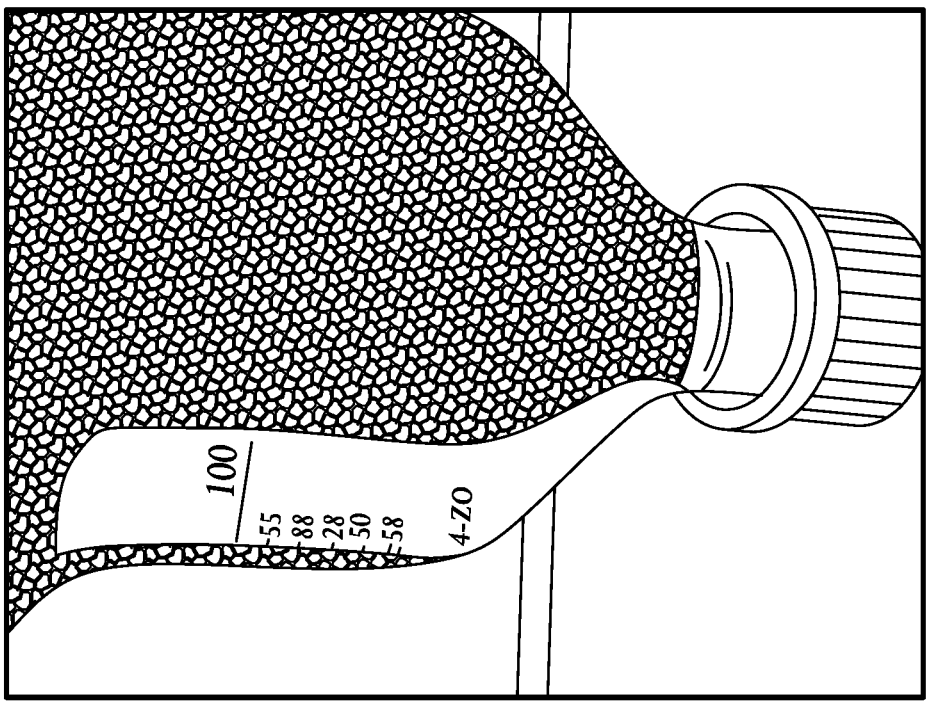
FIGS. 21A and 21B are photographs showing large (21A) and small (21B) exemplary PVA/SA boric acid hydrogel particles in bubbled column reactors.
Figure 21A:
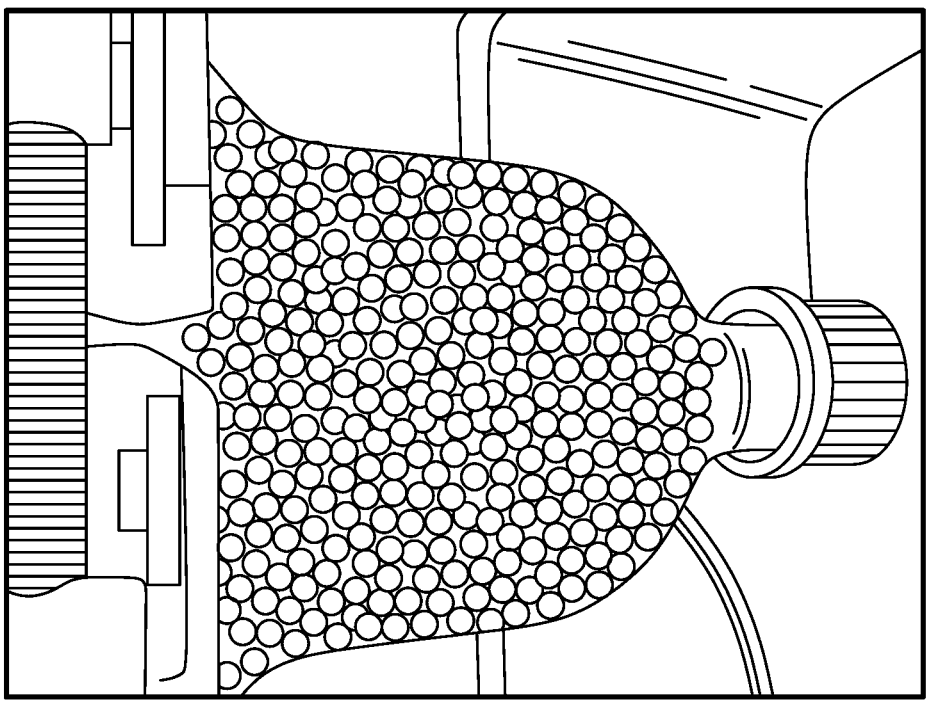

Since this PEG/SA gel formulation contains alginate, one can take advantage of the strong interaction between alginate and acrylamide to produce very tough gels. One can also make use of alginate-polycation complexes such as the complex formed with chitosan to form layers on the surface of the PEG/SA gel beads. It is possible to form a skin layer on the beads by dropping the PEGDMA/SA mix into a $CaCl_2$ bath containing high MW, e.g., over 400 kDa, chitosan, and the layer can be thickened by alternating alginate and chitosan soaks if that is desired for a particular application. The inventors have used the chitosan skin layer to help slow the diffusion of monomers from the beads as they solidify in the $CaCl_2$ bath. This allows the use of less radical initiator, thus reducing stress on the bacteria being immobilized 7. Scaling up the Hydrogel Bead Production Process The inventors have built a multi-orifice device for dripping the viscous PVA/SA solution into the bead-forming boric acid/$CaCl_2$ solution at a high enough rate to make producing large batches of beads more practical (FIG. 20B). This device has 24 stainless steel needles that can be of any chosen gauge; needles are placed around the circumference of a large round container which will hold the boric acid solution. The solution is stirred by an overhead mechanical stirrer as magnetic stirrers become impractical for large bead batches. The needles are in groups of six in ~2" diameter plastic "dripping heads" and the 4 dripping heads are then placed above the buffer container arranged around the circumference of the container so that the gelling beads will be able to traverse ¼ of the circumference before encountering the droplets from the next dripping head. This 24-needle dropping device includes the features necessary to add a strong electric field in order to produce smaller droplets (FIG. 20A).

7.1 Optimization of Particle Size

It is not possible to make PVA/SA boric acid hydrogel beads smaller than about 2-3 mm diameter by gravity dripping due to the viscosity of the PVA/SA solution. Applying a strong electric field between the drop forming orifice and the receiving vessel is known to produce much smaller droplets. The electrostatic method provides a way to reduce the size of the droplets, and thus the hydrogel beads, towards the ultimate goal of ~0.5 mm diameter (FIGS. 14A-F). A metal plate has been added which contacts the metal needles to charge the droplets and to create a uniform electric field between the droplet orifices and the receiving container (FIG. 15).

8. Development and Applications of Dispersed Catalyzed Liquid Phase Oxygen Supply (LPOS)

Portable bioreactors have the potential to enable humanitarian, military, and remote exploration operations to meet basic health and sanitation needs under challenging conditions. A common challenge in these applications is the supply of oxygen to support aerobic organisms. Electric grids are either unavailable or unreliable for powering aerators where portable bioreactors are needed, and portable power supplies add significant logistical hurdles. Compressed oxygen is not considered viable because the risk of combustion and restrictions on transporting compressed gas cylinders by air travel. This has been solved prior with passive diffusion through gas exchange membranes on a laboratory scale, but passive diffusion becomes process limiting as greater reaction rates are desired per unit volume. Therefore, active methods to deliver oxygen for bioprocessing are needed for portable bioreactors to better serve human health and sanitation.

Liquid Phase Oxygen Supply (LPOS) has typically been used to enhance oxygen supply where the product of interest is viscous and limits the diffusion of oxygen gas in large scale bioreactors. The well-established risk of the LPOS strategy is reduced bacterial activity due to toxicity of the $H_2O_2$. This risk is especially of concern in a portable bioreactor because a highly concentrated and active biomass is needed to maintain high activity in a small volume, and any attenuation in cell activity would have to be compensated with a larger, less portable reactor. Prior researchers addressed the issue of toxicity with controlled feeding of hydrogen peroxide based on a dissolved oxygen (DO) setpoint and Proportional-Integrative-Derivate (PID) control loops showed to be particularly effective at preventing toxic effects. Other works established a maximum flow rate of hydrogen peroxide based on cell concentration and expected $H_2O_2$ utilization rate. These approaches were constrained by reliance on catalase positive organisms to convert $H_2O_2$ to oxygen.

Herein, the inventors have demonstrated a PID control strategy and a catalase positive nitrifier, but the catalase capacity was supplemented with platinum powder to enable a consistent predictive breakdown of hydrogen peroxide to oxygen. Platinum was chosen because it was found to be the most rapid catalyst of $H_2O_2$ decomposition among transition group metals, and unlike catalase the catalyst does not appear to denature and lose activity over time. Initially, trials with platinum powder entrapped in abiotic beads was conducted; however, the time between addition of $H_2O_2$ and the observance of full conversion to DO was too long (45 minutes). The configuration immobilized the platinum near the bacteria for consistent protection but resulted in a delayed DO signal, which was problematic for tight control of $H_2O_2$ based on DO feedback. The immobilized platinum configuration could be useful when hydrogen peroxide is diffusing from a reservoir inside the hydrogel bead, with organisms similarly immobilized outside the reservoirs. In such cases, oxygen concentrations are not controlled by active monitoring of DO, but instead by material properties which regulate the diffusion of hydrogen peroxide from within the hydrogel. The delayed signal is also expected to be an issue when catalase positive organisms are immobilized in hydrogels without the addition of an external catalyst.

Figure 22:
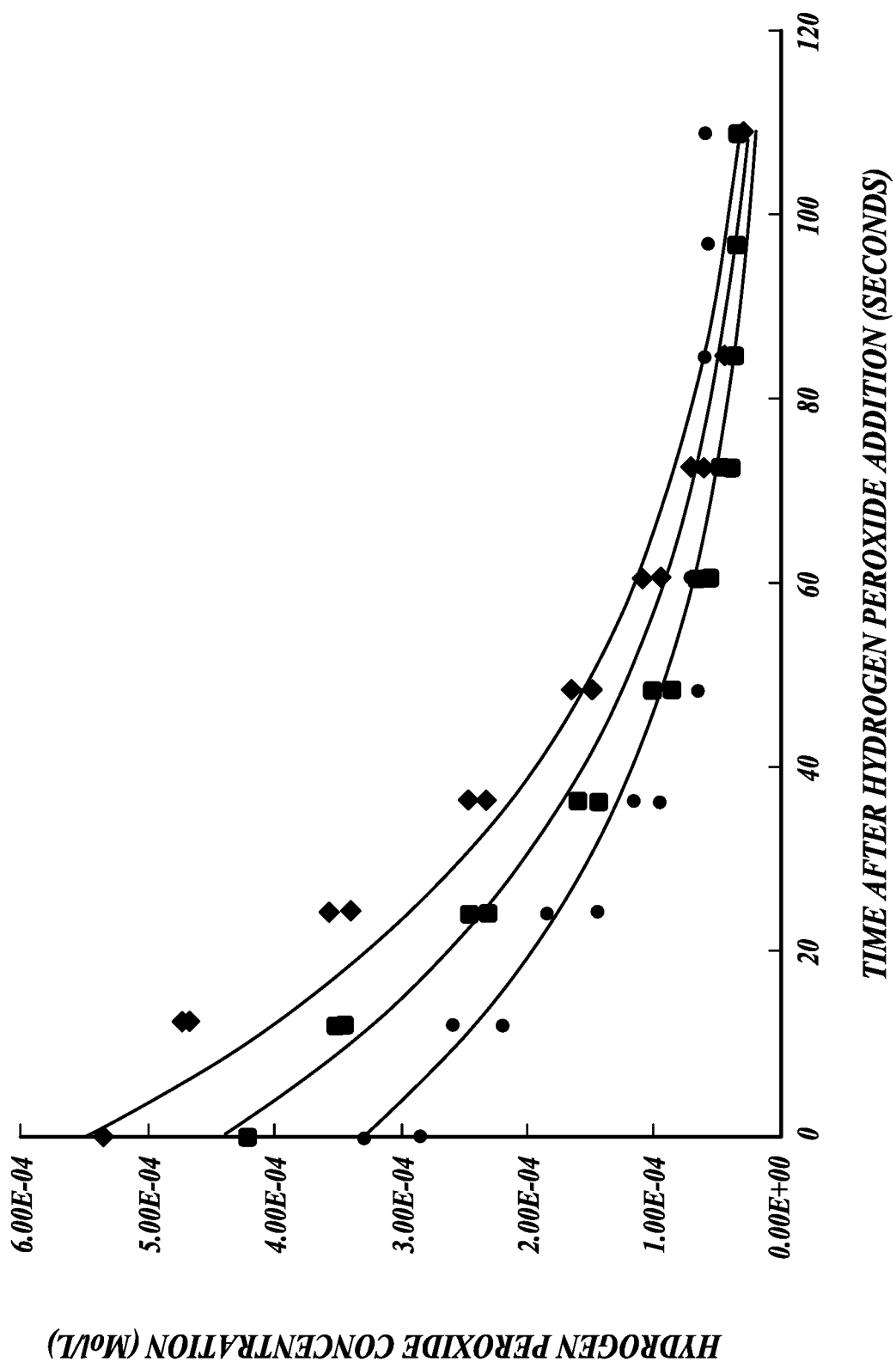
FIG. 22 shows a model to predict concentration of hydrogen peroxide in the reactor compared to actual concentrations of hydrogen peroxide. The concentration of hydrogen peroxide is shown following additions of (●) 0.075 (■) 0.1 (♦) 0.125 ml of 3% $H_2O_2$, while the predicted ($[C_{H2O2}]= [C_{H2O2}]o*e-0.027t$) is represented by a solid line of the corresponding color. The reactor had a volume of 225 ml and 50% of that volume was filled with beads and included 0.55 g/L of >3 μm platinum powder that were suspended outside the beads. $R^2=0.96$

As an alternative to embedding platinum inside the hydrogels, dispersing platinum in the liquid media (outside the hydrogel beads) enabled the rapid conversion of $H_2O_2$ to DO; a dose of $H_2O_2$ needed to fully saturate the reactor DO (6.8 mg $O_2$ $L^{-1}$) was 95% converted to oxygen within 110 seconds (0.125 g of powdered platinum in 225 ml reactor volume). This is significantly faster than reaction rates observed with immobilized platinum and hence is a preferred option for rapid conversion at high conversion efficiency. The platinum also enabled $H_2O_2$ degradation to reliably follow first order kinetics (FIG. 22), which in turn enabled the determination of the maximum flow rate of $H_2O_2$ (Equation 1) to constrain the PID control scheme from overdosing. This control scheme enabled $H_2O_2$ dosing based on observed DO levels and negated the need for an additional probe to measure $H_2O_2$ concentration, as had been done prior. In turn, this can reduce the weight of a portable bioreactor.

$$\frac{d[M_{H2O2}]_{max}}{dt} = k * [C_{H2O2}]_{max} * V$$

Figure 23:
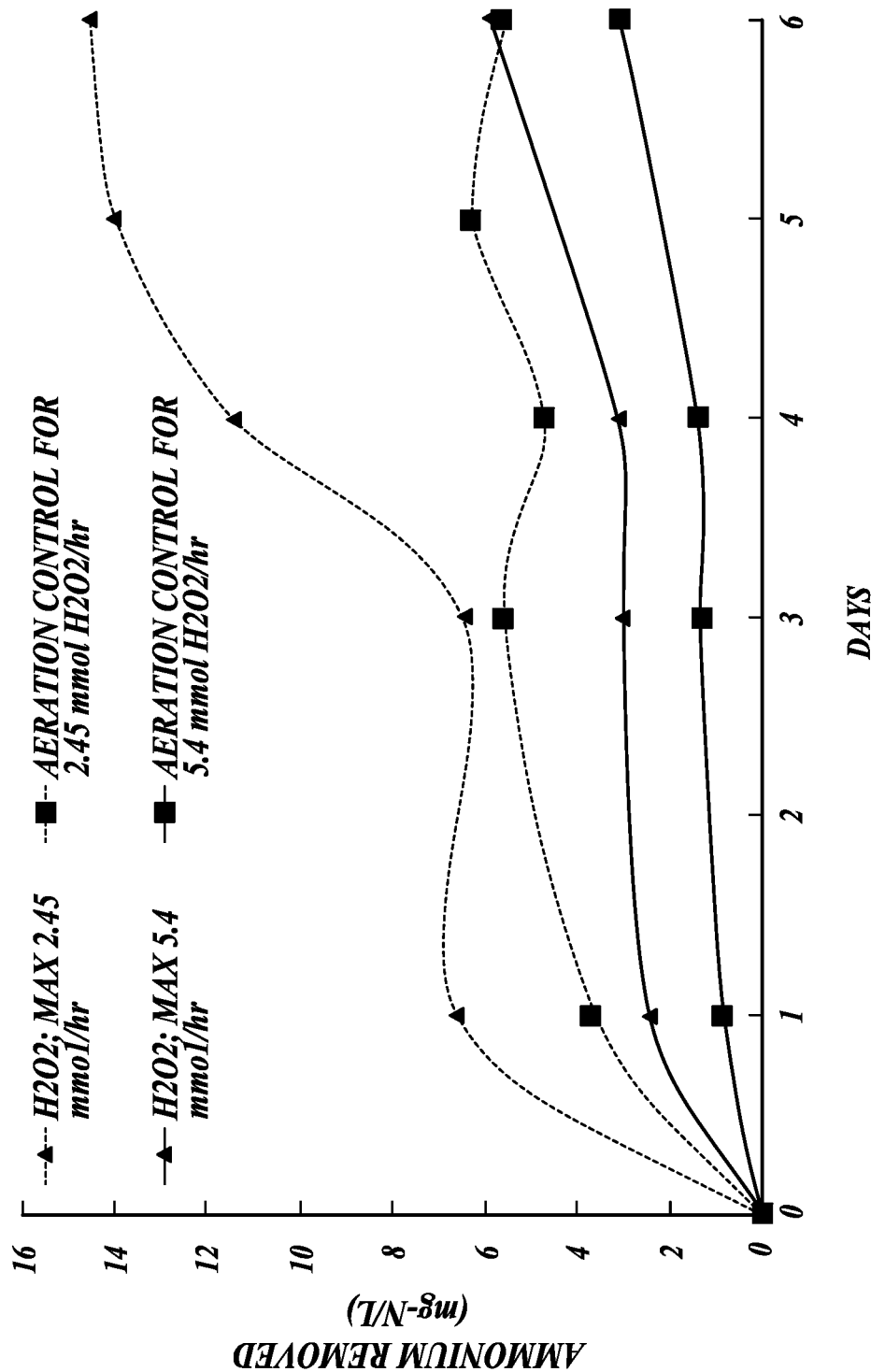
FIG. 23 is a graph of ammonia removal using hydrogen peroxide vs. aeration. Ammonium removal was performed by a catalase positive nitrifier immobilized in PVA-SA gel beads with suspended powdered platinum outside the beads catalyzing the conversion of hydrogen peroxide into dissolved oxygen. Dissolved oxygen was controlled at 3 mg $L^{-1}$, with a maximum hydrogen peroxide pumping rate (2.45 or 5.4 mmol/hr) set to limit potential toxicity. Each hydrogen peroxide pumping rate is compared to an aeration control on the same batch of beads with an immobilized nitrifier. The results indicate short-term dosing of hydrogen peroxide is similar to aeration-based ammonium oxidation.

The platinum-catalyzed control scheme was confirmed to not result in toxic effects when it performed comparable to the use of aeration. As seen in FIG. 23, hydrogen peroxide supplied trials had comparable or faster nitrification rates to aeration in the first six days. In FIG. 23, each pair of hydrogen peroxide and aeration trials are performed on a different batch of Comammox beads. Each batch of beads varied in quantity of Comammox; therefore, it could not be concluded that either pumping rate of hydrogen peroxide is superior for nitrification. Nonetheless, comparing hydrogen peroxide treatments to their aeration controls (same batch) showed nitrogen removal rates under hydrogen peroxide were comparable to aeration in the short-term treatments. Overall, the results presented here confirm the advantages of LPOS in the preceding literature and build on the prior work by demonstrating abiotic catalyst can enhance the reliability and control of LPOS.

The above described experimentation and modeling, as shown in Table 2 below, demonstrates that hydrogen peroxide, delivered via LPOS is the lowest weight options for oxygen supply. LPOS requires only 7.6 mg of added weight to the bioreactor and results in 92% oxygen utilization efficiency (oxygen dissolved/oxygen delivered as $H_2O_2$). In comparison, aeration with a theoretically produced blower which can achieve 60% efficiency requires 18.8 mg of battery to deliver a single mg of dissolved oxygen. Such a blower for small scale options does not yet exist on the market. Converting hydrogen peroxide to oxygen gas, then attempting to dissolve that gas through diffusion is far less efficient than LPOS in terms of oxygen transfer efficiency and therefore requires 40.7 mg of hydrogen peroxide (30% w/w) to deliver a single mg of dissolved oxygen. Therefore, LPOS is critical to making bioreactors light weight and more portable. In turn, platinum catalyzed LPOS protects biology when using LPOS by enabling reliable conversion to DO and tight control of dosing based on a DO feedback loop.

TABLE 2

Summary Comparison of Options to Supply Oxygen to a Comammox culture maintained at 37° C. and 3 mg $O_2$ $L^{-1}$. $dM/dM_{DO}$ represents the added weight to a bioreactor for supplying each mg of dissolved oxygen, accounting for barriers to diffusion of oxygen gas.

| Option | $dM/dM_{DO}$ at optimum conditions (mg added weight $mg^{-1}$ DO delivered) (Modeled based on experimentally determined values) | Oxygen Transfer efficiency (mg oxygen dissolved $mg^{-1}$ oxygen delivered) (Determined experimentally) |
|---|---|---|
| Aeration (at H = 110 mm) | | |
| Optimized blower (60% efficient) | 18.4 | 0.01 |
| Tetra Whisper 10 (2.2% efficient) | 369 | 0.01 |
| Electrolysis | 35.5 | NA |
| Dissolution of Oxygen Gas generated from Hydrogen Peroxide | 40.7 | 0.08 |
| Platinum Catalyzed LPOS via Hydrogen Peroxide (30% $H_2O_2$) | 7.6 | 0.92 |

In addition to portable bioreactors, there is a need for delivering oxygen to targeted areas within the body. Recent advances in delivering oxygen to topical wounds has demonstrated the predictable release of hydrogen peroxide on a wound is possible by entrapping the hydrogen peroxide in poly(methyl methacrylate) (PMMA) microcapsules, whereby the hydrogen peroxide diffuses out of the microcapsule. PMMA is already FDA approved for certain surgical applications. Hydrogen peroxide delivery into the human gut has also been proposed for enhancing cell growth to aid the attachment of synthetic epithelial linings. It is plausible hydrogen peroxide microcapsules could also be incorporated in a hydrogel bead for targeted aerobic bioprocesses within the digestive system. In these situations, the use of abiotic catalyst could also be embedded in the same hydrogel to ensure the rapid breakdown of diffused hydrogen peroxide to oxygen, thereby protecting the entrapped biology also within the hydrogel. If the hydrogel is stable, the abiotic catalyst will be excreted intact preventing the release of the catalyst into the gut. In this envisioned application the hydrogel would embed abiotic catalyst, microorganisms, and hydrogen peroxide microcapsules. If ingested, aerobic organisms could then operate in the low oxygen environment of the gut to consume toxins or amend the function of the microbiome in a targeted way. The abiotic catalyst would ensure a high concentration of cells could remain active by protecting the cells from the toxic effects of hydrogen peroxide.

Thus, provided and demonstrated herein is a method for entrapping abiotic catalysts within hydrogels, or in outer shell of a multilayered hydrogel bead, such that peroxide can be added to the bulk liquid to supply oxygen to aerobic organisms entrapped within the beads, or hydrogen peroxide reservoirs (e.g. microcapsules) can be embedded in the hydrogel for controlled diffusion outward toward the organisms. The abiotic catalysts can enhance the biological processing capacity by protecting the microorganisms from the toxic effects of peroxides, but also enabling high oxygen supply levels to ensure the microorganisms do not become oxygen limited by barriers such as the rate of dissolution of gases, competing consumption of oxygen within a highly active environment, or lack of access to other oxygen supply sources.

While illustrative embodiments have been illustrated and described, it will be appreciated that various changes can be made therein without departing from the spirit and scope of the invention.

The embodiments of the invention in which an exclusive property or privilege is claimed are defined as follows:

1. A composition for reducing the concentration of one or more contaminants in a fluid, comprising:
    a plurality of particles comprising a hydrogel core surrounded by a polymer shell, wherein the hydrogel core further comprises microorganisms,
    wherein the polymer shell is bound to the hydrogel core by covalent bonding, ionic bonding, or a combination thereof,
    wherein the hydrogel core comprises (a) alginate and a polymer of one or more acylate derivatives of polyethylene glycol (PEG); or (b) polyvinyl alcohol (PVA), alginate, and carboxymethyl cellulose (CMC).

2. The composition of claim 1, wherein the one or more colonies of microorganisms comprise active autotrophic microorganisms, active heterotrophic microorganisms, or a combination thereof.

3. The composition of claim 1, wherein the fluid is wastewater, urine, or metabolic function fluid.

4. The composition of claim 1, wherein the one or more contaminants comprise urea, sweat, or a combination thereof.

5. The composition of claim 1, wherein the microorganisms are bacteria or archaea.

6. The composition of claim 1, wherein the microorganisms comprise anaerobic microorganisms, aerobic microorganisms, or a combination thereof.

7. The composition of claim 1, wherein the microorganisms comprise ammonia-oxidizing bacteria.

8. The composition of claim 6, wherein the microorganisms are *Nitrosomonas europaea, Nitrososphaera vienensis*, commamox type *Nitrospira*, or a combination thereof.

9. The composition of claim 1, wherein the hydrogel is formed by polymerization of a mixture comprising one or more acrylate derivatives of polyethylene glycol (PEG) and alginate.

10. The composition of claim 9, wherein the one or more acrylate derivatives of polyethylene glycol (PEG) is PEG acrylate, PEG methacrylate, N-PEG acrylamide, N-PEG methacrylamide, PEG diacrylate (PEGDA), PEG dimethacrylate (PEGDMA) or a combination thereof.

11. The composition of claim 9, wherein the mixture further comprises a photoactivator.

12. The composition of claim 9, wherein the hydrogel is crosslinked.

13. The composition of claim 1, wherein the hydrogel comprises polyvinyl alcohol, sodium alginate, and carboxymethyl cellulose.

14. The composition of claim 1, wherein the shell comprises SBQ-PVA.

15. The composition of claim 1, wherein each of the core and the shell comprise microorganisms, wherein the microorganisms in the shell and the microorganisms in the core are the same or different.

16. The composition of claim 15, wherein the microorganisms in the core are anaerobic microorganisms and the microorganisms in the shell are aerobic microorganisms.

17. A method for removal of one or more contaminants from a fluid comprising contacting the fluid comprising one or more contaminants with the composition of claim 1.

18. A method for forming hydrogel particles as characterized in claim 1, the method comprising: forming a droplet of a first solution comprising alginate and one or more acrylate derivatives of polyethylene glycol (PEG) and one or more polymerization initiators and dropping the droplet into a second solution comprising calcium or barium ions.

* * * * *